(12) United States Patent
Dale et al.

(10) Patent No.: US 7,601,887 B2
(45) Date of Patent: Oct. 13, 2009

(54) BANANA RESISTANCE GENES AND USES THEREOF

(75) Inventors: James Langham Dale, Moggill (AU); Santy Peraza Echeverria, Merida (MX)

(73) Assignee: Queensland University of Technology, Brisbane, Queensland (AU)

( * ) Notice: Subject to any disclaimer, the term of this patent is extended or adjusted under 35 U.S.C. 154(b) by 66 days.

(21) Appl. No.: 10/573,372

(22) PCT Filed: Sep. 23, 2004

(86) PCT No.: PCT/AU2004/001300

§ 371 (c)(1),
(2), (4) Date: Oct. 31, 2006

(87) PCT Pub. No.: WO2005/028651

PCT Pub. Date: Mar. 31, 2005

(65) Prior Publication Data

US 2007/0204368 A1 Aug. 30, 2007

(30) Foreign Application Priority Data

Sep. 25, 2003 (AU) .............................. 2003905222

(51) Int. Cl.
*C12N 15/09* (2006.01)
*C12N 15/82* (2006.01)
*A01H 5/00* (2006.01)

(52) U.S. Cl. .................. 800/279; 800/278; 800/320; 800/317; 435/468; 435/419; 435/320.1; 435/430.1; 536/23.6

(58) Field of Classification Search ................ None
See application file for complete search history.

(56) References Cited

U.S. PATENT DOCUMENTS

2004/0237137 A1 * 11/2004 Osumi et al. ................. 800/279

FOREIGN PATENT DOCUMENTS

| EP | 1 024 196 A1 | 8/2000 |
|---|---|---|
| EP | 1 334 979 A1 | 8/2003 |
| WO | WO 96/32007 | 11/1996 |
| WO | WO 97/06259 | 2/1997 |
| WO | WO 97/06259 A2 | 2/1997 |

OTHER PUBLICATIONS

Parker et al. The Plant Cell (1996), vol. 8, pp. 2033-2046.*
Broun et al. Science, Nov. 13, 1998, vol. 282, pp. 1315-1317.*
Chakrabarti, et al., "MSI-99, a magainin analogue, imparts enhanced disease resistance in transgenic tobacco and banana," *Planta* 216(4):587-596 (2003).
European search report under Application No. EP 04 76 1335 dated Feb. 9, 2007.
Ferrier-Cana, et al., "Characterization of expressed NBS-LRR resistance gene candidates from common bean," *Theor. Appl. Genet.* 106:251-261 (2003).
Gimenez, et al., Database EMBL accession No. AF529036, XP002415634 (Aug. 29, 2002), (Abstract).
Javed, et al., "Study of resistance of *Musa acuminate* to *Fusarium oxysporum* using RAPD markers," *Biologia Plantarum* 48(4):93-99 (2004).
Ortiz-Vázquez, et al., "Construction and characterization of a plant transformation-competent BIBAC library of the black Sigatoka-resistant banana *Musa acuminate* cv. Tuu Gia (AA)," *Theor. Appl. Genet.* 110:706-713 (2005).
Vilarinhos, et al., "Construction and characterization of a bacterial artificial chromosome library of banana (*Musa acuminate Colla*)," *Theor. Appl. Genet.* 106:1102-1106 (2003).
Wiame, et al., "PCR-based cloning of candidate disease resistance genes from banana (*Musa acuminata*)," *Acta. Hort.* 521:51-57 (Proc. XXV IHC, Part 11) (2000).
EMBL Database Accession No. CAD58967. Disease Resistance Protein NBS-LRR type (*Musa acuminata*). Dec. 15, 2002.
Aarts et al. (1998). "Different requirements for EDS1 and NDR1 by disease resistance genes define at least two R gene-mediated signalling pathways in *Arabidopsis*." PNAS. 95: 10306-10311.
Aarts et al. (1998). "Identification of R-gene homologous DNA fragments genetically linked to disease resistance loci in *Arabidopsis thaliana*." Mol. Plant-Microbe Interact. 11: 251-258.
Anderson et al. (1997). "Inactivation of the flax rust resistance gene M associated with loss of a repeated unit within the leucine-rich repeated coding region." Plant Cell. 9: 641-651.
Aravind et al. (1999). "The domains of the death: evolution of the apoptosis machinery." Trends in Biochemical Science. 24: 47-53.
Asai et al. (2002). "MAP kinase signalling cascade in *Arabidopsis* innate immunity." Nature. 415: 977-983.
Baker et al. (1997). "Signaling in plant-microbe interactions." Science. 276: 726-733.
Ballvora et al. (2002). "The R1 gene for potato resistance to late blight (*Phytophthora infestas*) belongs to the leucine zipper/NBS/LRR class of plant resistance gene." The Plant Journal. 30: 361-371.
Becker et al. (2000). "Genetic transformation of Cavendish banana (Musaspp. AAA group) cv ' Grand Nain' via microprojectile bombardment." Plant Cell Reports. 19: 229-234.
Bendahmane et al. (1999). "The Rx gene from tomato controls separate virus resistance and cell death responses." Plant Cell. 11:781-791.
Bentley et al. (1998). "Genetic variation among vegetative compatibility groups of *Fusarium oxysporum* f. sp. cubense analysed by DNA fingerprinting." Phytopathology. 88: 1283-1293.

(Continued)

*Primary Examiner*—Medina A Ibrahim
(74) *Attorney, Agent, or Firm*—Knobbe Martens Olson & Bear LLP

(57) ABSTRACT

The present invention relates to two banana resistant genes, RGA5 and RGA2, and methods of producing transgenic plants having resistance to *fusarium* by transforming the plants with RGA5 or RGA2 polynucleotide sequences. The invention also relates to plants transformed with the RGA5 or RGA2 polynucleotide sequences, and methods of breeding plants for *fusarium* resistance by crossing transformed plants expressing RGA5 or RGA2 polypeptides with *fusarium* susceptible plants.

25 Claims, 5 Drawing Sheets

OTHER PUBLICATIONS

Bittner-Eddy et al. (2000). "RPP13 is a simple locus in *Arabidopsis thaliana* for alleles that specify downy mildew resistance to different avirulence determinants in *Peronospora parasitica*." The Plant Journal. 21: 177-188.

Bonas et al. (2002). "Plant disease resistance triggered by pathogen-derived molecules: refined models of specific recognition." Current Opinion in Microbiology. 5: 44-50.

Botella et al. (1998). "Three genes of the *Arabidopsis* RPP1 complex resistance locus recognize distinct *Peronospora parasitica* avirulence determinants." Plant Cell. 10: 1847-1860.

Brommonschenkel et al. (2000). "The broad-spectrum tospovirus resistance gene Sw-5 of tomato is a homolog of the root-knot nematode resistance gene Mi." Molecular Plant Microbe Interaction. 13: 1130-1138.

Brueggeman et al. (2002). "The barley steam rust-resistance gene Rpg1 is a novel disease-resistance gene with homology to receptor kinases." PNAS. 1-6.

Bryan et al. (2000). "A single amino acid difference distinguishes resistant and susceptible alleles of the rice blast resistance gene Pi-ta." Plant Cell. 12: 2033-2045.

Cai et al. (1997). "Positional cloning of a gene for nematode resistance in sugar beet." Science. 275: 832-834.

Cao et al. (1997). "The *Arabidopsis* NPR1 gene that controls systemic acquired resistance encodes a novel protein containing ankyrin repeats." Cell. 88:57-63.

Cao et al. (1998). "Generation of broad-spectrum disease resistance by overexpression of an essential regulator gene in systemic aquired resistance." PNAS. 95: 6531-6536.

Century et al. (1997). "NDR1, a pathogen-induced component required for *Arabidopsis* disease resistance." Science. 278: 1963-1965.

Chern et al. (2001). "Evidence for a disease- resistance pathway in rice similar to the NPR1-mediated signalling pathway in *Arabidopsis*." The Plant Journal. 27: 101-113.

Cohn et al. (2001). "Innate immunity in plants." Current Opinion in Immunology. 13:55-62.

Collins et al. (1999). "Molecular characterization of the Maize Rp1-D Rust resistance haplotype and its mutants." Plant Cell. 11: 1365-1376.

Despres et al. (2000). "The *Arabidopsis* NPR1/NIM1 protein enhances the DNA binding activity of a subgroup of the TGA family of bZIP transcription factors." Plant Cell. 12: 279-290.

Dixon et al. (1998). "The tomato Cf-5 disease resistance gene and six homologs show pronounced allelic variation in leucine-rich repeat copy number." Plant Cell. 10: 1915-1925.

Dodds et al. (2000). "Six amino acid changes confined to the Leucine-Rich repeat B-strand/B-turn motif determine the difference between the P and P2 rust resistance specificities in flax." Plant Cell. 13: 163-178.

Ellis et al. (1998). "Structure and function of proteins controlling strain-specific pathogen resistance in plants." Current Opinion in Plant Biology. 1: 288-293.

Ellis et al. (2000). "The generation of plant disease resistance gene specificities." Trends in Plant Science. 5: 373-379.

Endo et al. (1996). "Large-scale search for genes on which positive selection may operate." Molecular Biology Evolution. 13: 685-690.

Ernst et al. (2002). "The broad-spectrum potato cys nematode resistance gene (*Hero*) from tomato is the only member of a large gene family of NBS-LRR genes with and unusual amino acid repeat in the LRR region." Plant Journal. 31: 127-136.

Falk et al. (1999). "EDS1, an essential component of R gene-mediated disease resistance in *Arabidopsis* has homology to eukaryotic lipases." PNAS. 96: 3292-3297.

Gassmann et al. (1999). "The *Arabidopsis* RPS4 bacterial-resistance gene is a member of the TIR-NBS-LRR family of disease resistance genes." Plant Journal. 20: 265-277.

Glazebrook, J. (2001). "Genes controlling expression of defence responses in *Arabidopsis*." Curr. Opinion in Plant Biol. 4: 301-308.

Gomez-Gomez et al. (2000). "FLS2: An LRR receptor-like kinase involved in the perception of the bacterial elicitor flagellin in *Arabidopsis*." Mol. Cell. 5: 1003-1011.

Graham et al. (2000). "Expression and genome organization of resistance gene analogues in soybean." Genome. 43: 86-93.

Grant et al. (1995). "Structure of the *Arabidopsis* RPM1 enabling dual specifity disease resistance." Science. 269: 843-846.

Hammond-Kosack et al. (1997). "Plant resistance genes." Annu. Rev. Plant. Physiol. Plant Mol. Biol. 48: 575-607.

Hughes et al. (1988). "Pattern of nucleotide substitution at major histocompatibility complex class I loci reveals overdominant selection." Nature. 335: 167-170.

Hulbert et al. (2001). "Resistance gene complexes: evolution and utilization." Annu. Rev. Phytopathol. 39: 285-312.

Jia et al. (2000). "Direct interaction of resistance gene and avirulence gene products confers rice blast resistance." EMBO J. 19: 4004-4014.

Johal et al. (1992). "Reductase activity encoded by the HM1 disease resistance gene in maize." Science. 258: 985-987.

Kanazin et al. (1996). "Resistance gene analogs are conserved and clustered in soybean." PNAS. 93: 11746-11750.

Kawchuk et al. (2001). "Tomato Ve disease resistance genes encode cell surface-like receptors." PNAS. 98: 6511-6515.

Kinkema et al. (2000). "Nuclear localization of NPR1 is required for activation of PR gene expression." The Plant Cell. 12: 2339-2350.

Lagudah et al. (1997). "Map-based cloning of a resistance gene sequence encoding a nucleotide-binding domain and leucine rich region at the Cre3 nematode resistance locus of wheat." Genome. 40: 659-665.

Lawrence et al. (1995). "The L6 gene for flax rust resistance is related to the *Arabidopsis* bacterial resistance gene RPS2 and the tobacco viral resistance gene N." Plant Cell. 7: 1195-1206.

Leister et al. (1996). "A PCR-based approach for isolating pathogen resistance genes from potato with potential for wide application in plants." Nature Genetics. 14: 421-429.

Leister et al. (1998). "Rapid organization of resistance gene homologues in cereal genomes." PNAS. 95: 370-375.

May et al. (1995). "Generation of transgenic banana (*Musa acuminata*) plants via *Agrobacterium*-mediated transformation." Bio/Technology. 13: 486-492.

Mes et al. (2000). "Expression of the Fusarium resistance gene I-2 colocalizes with the site of fungal containment." The Plant Journal. 23: 183-193.

Meyers et al. (1998). "Receptor-like genes in the major resistance locus in lettuce are subject of divergent selection." Plant Cell. 11: 1833-1846.

Meyers et al. (1999). "Plant disease resistance genes encode members of an ancient and diverse protein family within the nucleotide-binding superfamily." The Plant Journal. 20: 317-332.

Milligan et al. (1998). "The root knot resistance gene Mi from tomato is a member of the leucine zipper, nucleotide binding site, leucine-rich repeat family of plant genes." The Plant Cell. 10: 1307-1319.

Mindrinos et al. (1994). "The A. thaliana disease resistance gene RPS2 encodes a protein containing a nucleotide-binding site and leucine-rich repeats." Cell. 78: 1089-1099.

Muskett et al. (2002). "*Arabidopsis* RAR1 exerts rate-limiting control of R genes-mediated defenses against multiple pathogens." The Plant Cell. 14: 979-992.

Pan et al. (2000). "Divergent evolution of plant NBS-LRR resistance gene homologues in dicot and cereal genomes." Journal of Molecular Evolution. 50: 203-213.

Parker et al. (1997). "The *Arabidopsis* downy mildew resistance gene RPP5 shares similarity to the toll interleukine-1 receptors with N and L6." The Plant Cell. 9: 879-894.

Parniske et al. (1997). "Novel disease resistance specificities result from sequence exchange between tandemly repeated genes at the Cf-4/9 locus of tomato." Cell. 91: 821-832.

Ploetz R (2000). "Panama disease: a classical and destructive disease of banana." Online. Plant Health Progress doi: 10. 1094/PHP-2000-1240-01-HM.

Richter et al. (2000). "The evolution of disease resistance genes." Plant Molecular Biology. 42: 195-204.

Rommens et al. (2000). "Exploiting the full potential of disease-resistance genes for agricultural use." Current Opinion in Biotechnology. 11: 120-125.

Ryals et al. (1997). "The *Arabidopsis* NIM1 protein shows homology to the mammalian transcription factor inhibitor IkB." The Plant Cell. 9: 425-439.

Sagi et al. (1995). "Genetic transformation of banana and plantain (*Musa* spp) via particle bombardment." Nature Biotechnology. 13: 481-485.

Saleron et al. (1996). "Tomato Prf is a member of a leucine-rich repeat class of plant disease resistance gene and lies embedded within the Pto kinase gene cluster." Cell. 86: 123-133.

Shen et al. (1998). "Resistance gene candidates identified by PCR with degenerate oligonucleotide primers Map to clusters of resistance genes in lettuce." Molecular Plant Pathogen Interaction. 11: 815-823.

Shirasu et al. (1999). "A novel class of eukaryotic zinc-binding proteins is required for disease resistance signalling in barley and the development in *C. elegans*." Cell. 99: 355-366.

Simons et al. (1998). "Dissection of the *Fusarium* 12 gene cluster in tomato reveals six homologs and one active gene copy." The Plant Cell. 10: 1055-1068.

Song et al. (1997). "Evolution of the rice Xa21 disease resistance gene family." Plant Cell 9: 1279-1287.

Song et al. (1998). "A receptor kinase-like protein encoded by the rice disease Xa21." Science. 270: 1804-1806.

Stuiver et al. (2002). "Engineering disease resistance in plants." Nature. 411: 865-868.

Tai et al. (1999). "Expression of the Bs2 pepper gene confers resistance to bacteria spot disease in tomato." PNAS. 96: 14153-14158.

The *Arabidopsis* Initiative (2000). "Analysis of the genome sequence of the flowering plant *Arabidopsis thaliana*." Nature. 408: 796-815.

Thomas et al. (1997). "Characterization of the tomato Cf-4 gene for resistance to *Cladosporium fulvum* identifies sequences that determine recognitional specificity in Cf-4 and Cf-9." Plant Cell. 9: 2209-2224.

Tornero et al. (2002). "RAR1 and NDR1 contribute quantitatively to disease resistance in *Arabidopsis*, and their relative contributions are dependent on the R gene assayed." Plant Cell. 14: 1005-1015.

Van Der Biezen et al. (1998). "Plant disease-resistance proteins and the gene-for-gene concept." Trend in Biochemistry Science. 23: 454-456.

Van der Hoorn et al. (2002). "Balancing selection favors guarding resistance proteins." Trends in Plant Science. 7: 67-71.

Van der Vossen et al. (2000). "Homologue of a single resistance-gene cluster in potato confer resistance to distinct pathogens: a virus and a nematode." Plant Journal. 23: 567-576.

Wang et al. (1998). "Xa21D encodes a receptor-like molecule with a leucine-rich repeat domain that determines race specific recognition and is subject to adaptive evolution." Plant Cell. 10: 1-15.

Warren et al. (1998). "A mutation within the leucine-rich repeat domain of the *Arabidopsis* disease resistance gene RPS5 partially suppresses multiple bacterial and downy mildew resistance genes." Plant Cell. 10: 1439-1452.

Wees et al. (2000). "Enhancement of induced disease resistance by simultaneous activation of salycilate-and jasmonate-dependent defense pathways in *Arabidopsis thaliana*." PNAS. 97: 8711-8716.

Whitham, S (1996). "The N gene of tobacco confers resistance to tobacco mosaic virus in transgenic tomato." PNAS. 93: 8776-8781.

Yoshimura et al. (1998). "Expression of Xa1, a bacterial blight-resistance gene in rice, is induced by bacterial inoculation." PNAS. 95: 1663-1668.

Yu et al. (1996). "Isolation of a superfamily of candidate disease-resistance genes in soybean based on a conserved nucleotide-binding site." PNAS. 93: 11751-11756.

Yu et al. (2001). "Evidence for an important role of WRKY DNA binding proteins in the regulation of NPRI gene expression." Plant Cell. 13: 1527-1540.

Zhang et al. (1999). "Interaction of NPR1 with basic leucine zipper protein transcription factors that bind sequences required for salysilic acid and induction of PR-1 gene." PNAS. 96: 6523-6528.

Zhou et al. (2000). "NPR1 differentially interacts with members of the TGA/OBF family of transcription factors that bind an element of the PR- 1 gene required for induction by salicylic acid." Mol Plant Microbe Interact. 13: 191-202.

Zou et al. (1997). "Apaf-1, a human protein homologous to *C. elegans* CED-4, participates in Cytochrome c-dependent activation of caspase-3." Cell. 90: 405-413.

Bent et al. (1996). "Plant Disease Resistance Genes: Function Meets Structure." Plant Cell. 8: 1757-1771.

Ellis et al. (1997). "Advances in the molecular genetic analysis of the flax-flax rust interaction." Annu. Rev. Phytopathol. 35: 271-291.

Gentzbittel et al. (1998). "Cloning of molecular markers for disease resistance in sunflower,*Helianthus annuus L*." Theor Appl Genet. 96: 519-525.

Kimura, M (1983). "The neutral theory of molecular evolution." Cambridge University Press.

Nimchuk et al. (2001). "Knowing the dancer from the dance: R-gene products and their interactions with other proteins from host and pathogen." Current Opinion in Plant Biology. 4: 288-294.

Ploetz et al. (2000). "Fungal disease of the root, corm and pseudosteam." In Diseases of banana, abaca and ensete. Jones, D. Ed. CABI.

Ortiz et al. (1995). "Banana and plantain breeding." Banana and Plantains. Gowen, S. Ed. Chapman and Hall London, pp. 110-146.

* cited by examiner

```
             10         20         30         40         50         60
         ....|....|....|....|....|....|....|....|....|....|....|....|
RGA5   1 MSTALVIGGWFAQSFIQTLLDKASNCATQQLARRRGLHDDLRRLRTSLLRIHAILDKAET  60
RGA2   1 -MADVTPQAAAVFSLVNEIFNRSINLIVAELRLQLNARAEINNLQRTLLRTHSLLEEAKA  59

70         80         90        100        110        120
         ....|....|....|....|....|....|....|....|....|....|....|....|
RGA5  61 RWNHKNTSLVELVRQLKDAAYDAELLEELEYQAAKQKVEHRGDQISDLFSESLSTASEW  120
RGA2  60 RR-MTDKSLVLWLMELKEWAYDADDILDEYEAAAIRLKVTR---S-----TEKRLIDHVI 110

130        140        150        160        170        180
         ....|....|....|....|....|....|....|....|....|....|....|....|
RGA5 121 LGADGDDAGTRLRELQGKLCNIAADMMDVMQLLAPDDGGRQFDWKVVRRETSSELTETVV 180
RGA2 111 INVP---LAHKVADIRKRINGVTLERELNIGALE---GSQPLDS-TKRGVTTSLLTESCI 163

190        200        210        220        230        240
         ....|....|....|....|....|....|....|....|....|....|....|....|
RGA5 181 FGRDQERBKVVELLLDSGSGNSSFSVLPLVGIGGVGKTTLAQLVYNDNRVGNYFHLKVWV 240
RGA2 164 VGRAQDKPNLIRLLLEPSDG--AVPVVPIVGLGGAGKTTLSQLIFNDKRVEEHFPLRMWV 221

250        260        270        280        290        300
         ....|....|....|....|....|....|....|....|....|....|....|....|
RGA5 241 CVSDNFNVKRLTKEIIESATKVEQSDKLNLDTLQQILKEKIASERFLLVLDDVWSFNRDD 300
RGA2 222 CVSDDEDVKRITREITEYATNGRFMDLTNLNMLQVNLKEEIRGTTFLLVLDDVWNEDPVK 281

310        320        330        340        350        360
         ....|....|....|....|....|....|....|....|....|....|....|....|
RGA5 301 WERLCAPLRFAARGSKVIVTTRDTKIASTIGTMKEISLDGLQDDAYWELFKKCAFGSVN- 359
RGA2 282 WESLLAPLDAGGRGSVVIVTTQSKNVADVTGTMEPYVLEEITEDDSWSLIESHSFREASC 341

370        380        390        400        410        420
         ....|....|....|....|....|....|....|....|....|....|....|....|
RGA5 360 PQEHLELEVIGRKIAGRLKGSPLAAKTLCSLLRLDVSQEHWRTIMESEVWQLPQAENEIL 419
RGA2 342 SSTNPRMEEIGRKIAKKISGLPYGATAMCRYLRSKHGESSWREVLETETMEMPPAASDVL 401

430        440        450        460        470        480
         ....|....|....|....|....|....|....|....|....|....|....|....|
RGA5 420 PVLWLSYQHLPGHLRQCFAFCAVFHKDYLFYKHELLQTWIAEGFIAHQGNKRMEDVGSSY 479
RGA2 402 SALRRSYDNLPPQLKLCFAFCALFTNGYRERKDTLIHMWIAQNLLQSTESKRSEDMAEEC 461

490        500        510        520        530        540
         ....|....|....|....|....|....|....|....|....|....|....|....|
RGA5 480 FHELVNRSFFQESRWRGRIVMHDLTILLAQFISVGECHRIDDKSKETPSTTRILSVALT 539
RGA2 462 FDDLVCRFFFRYS--WGNIVMNDSVHDLARWVSLDEYFRADEDSPLHISKPIRHLSWCSE 519

550        560        570        580        590        600
         ....|....|....|....|....|....|....|....|....|....|....|....|
RGA5 540 EQMKLVDFSGYN-KLRTLMINNQRNQYPYMTKVNSCLLPHSLFKRLKRIHVLVLQKCGMK 598
RGA2 520 RITNVLEDNNTGGDAVNPLSSLRTLLFLGQSEFRSYHLLDRMERMLSRIRVLDFSNQVIR 579
```

FIGURE 2-1

```
                 610        620        630        640        650        660
            ....|....|....|....|....|....|....|....|....|....|....|....|
RGA5  599   ELPDITGDLIQLRYLDISYNACIQRLPESLCDLYNKQALREWGCQLRSFPQGMSKLINLR   658
RGA2  580   NLPSSVGNLKHLRTLGLS-NTRIQRLPESVTRLCLLQTLLLEQCELCRLPRSMSRLVKLR   638

670        680        690        700        710        720
            ....|....|....|....|....|....|....|....|....|....|....|....|
RGA5  659   QLRVEDEITSKLYEVGKLISLQELSAFKVLNNHGNKLAELSGLTQLRSTLRITNLENVGS   718
RGA2  639   QLKANPDVIADIAKVGRLIELQELKAYNVDKKKGHGIAELSAMNQLHGDLSIRNLQNVEK   698

730        740        750        760        770        780
            ....|....|....|....|....|....|....|....|....|....|....|....|
RGA5  719   KELASKAKLHRKQYLEALELEWAAGQVSSLEHRLLVSEEVILGLQPHHFLKSLTIRGTSG   778
RGA2  699   TRESRKARLDEKQKLKLLDLRWADGRG---AGECDRDRKVIKGLRPIIPNLRELSIKYIGG   755

790        800        810        820        830        840
            ....|....|....|....|....|....|....|....|....|....|....|....|
RGA5  779   ATVPSWLDVKMLPNLGTLKLENCTRLEGLSYIGQLPHLKVLHMKRMPVVKQMSHELCGCT   838
RGA2  756   TSSPSWMTDQYLPNMETIRLRSCARLTELPCLGQLHILRHLHIDGMSQVRQINLQFYGTG   815

850        860        870        880        890        900
            ....|....|....|....|....|....|....|....|....|....|....|....|
RGA5  839   KSKLFPRLEELVLEDMFTLKEFPNLAQLPCLKIIHMKNMFAVKHIGRELYGDIESNCFLS   898
RGA2  816   EVSGFPLLELLNIRRMFSLEEWS--------------------------------EP     840

910        920        930        940        950        960
            ....|....|....|....|....|....|....|....|....|....|....|....|
RGA5  899   LEELVLQDMLTLEELPNLGQLPHLKVIHMKNMSALKLIGRELCDSREKIWFPRLEVLVLK   958
RGA2  840   ------------------------R-----------------RNCCYFPR--------   849

970        980        990       1000       1010       1020
            ....|....|....|....|....|....|....|....|....|....|....|....|
RGA5  959   NMLALEELPSLDNFRVSRFFASSVEVGHGLFSATRNKWFPRLEELEIKGMLTFEELHSLE  1018
RGA2  849   -----LH-----------------------------------------------------  851

1030       1040       1050       1060       1070       1080
            ....|....|....|....|....|....|....|....|....|....|....|....|
RGA5 1019   KLPCLKVFRIKGLPAVKKIGHGLFDSTCQRECFPRLEDLVLSDMPAWEEWSWAEREELFS  1078
RGA2  851   ------------------------------------------------------------  851

1090       1100       1110       1120       1130       1140
            ....|....|....|....|....|....|....|....|....|....|....|....|
RGA5 1079   CLCRLKTEQCPKLKCLLPIPHSLIKLELWQVGLTGLPGLCKGIGGSSTRTASLSLLHLI   1138
RGA2  851   ---KLLIFDCPRLRNLPSLPPTLEELRISRTGLVDLPG-FH--GNGDVTTNVSLSSLHVS   905

1150       1160       1170       1180       1190       1200
            ....|....|....|....|....|....|....|....|....|....|....|....|
RGA5 1139   KCPNLRNIGEGLLSNHIPHINAIRIWECAELLWLPVKRFREFTTLENLSTRNCPKLMSMT  1198
RGA2  906   ECRELRSLSEGLLQHNLVALKTAAFTDCDSLEFLPAEGFRTAISLESLIMTNCP--LPCS   963
```

FIGURE 2-2

```
            1210       1220       1230       1240       1250       1260
           ....|....|....|....|....|....|....|....|....|....|....|....|
RGA5  1199 QCEENDLLLPPLIKALELGDCG---NLGKSLPGCLHNLSSLTQLALSNCPYMVSLREVM 1255
RGA2   963 ------FLLPSSLEHLKLQPCLYPNNEDSLSTCFENLTSLSFLDIKDCPNLSSFPPGPL 1017

1270       1280       1290       1300       1310       1320
           ....|....|....|....|....|....|....|....|....|....|....|....|
RGA5  1256 LHLKELGTVRLENCDGLGSIEGLQVLKSLKRLALIGCPRLLNE-------GDEQGEVLS 1308
RGA2  1018 CQLSALQHLSLVNCQRLQSIG-FQALTSLESLTIQNCPRLTMSHSLVEVNNSSDTGLAFN 1076

1330       1340       1350       1360       1370       1380
           ....|....|....|....|....:....|....|....|....|....|....|....|
RGA5  1309 LLELSVDKT---ALLKLSLIKN---------TLPFIHSLRIIWSPQKVMEDLEEQELVHS 1356
RGA2  1077 ITRWMRRRTGDDGLMLRHRAQNDSFFGGLLQHLTFLQFLKICQCPDLVTFTGEEEEKWRN 1136

1390       1400       1410       1420       1430       1440
           ....|....|....|....|....|....|....|....|....|....|....|....|
RGA5  1357 ITALRRLEFFRCKNLQSLPTELHTLPSLHALVVSDCPQLQSLPEKGLPTLLTDLGFDHCH 1416
RGA2  1137 ITSLQILHIVDCPNLEVLPANLQSLCSLSTLYLVRCPRLHAFPPGCVSMSLAHLVIHECP 1196

1450       1460       1470
           ....|....|....|....|....|....|.
RGA5  1417 PVLT------AQLEKHLAEMK--SSGRFIPVYA--- 1441
RGA2  1197 QLCQRCDPPGGDDWPLIANVPRICLGRTIPCRCSTT 1232
```

BANANA RESISTANCE GENES AND USES THEREOF

CROSS-REFERENCE TO RELATED APPLICATIONS

This application is the U.S. National Phase filing under 35 U.S.C. §371 of PCT/AU2004/001300, filed Sep. 23, 2004, which designated the United States and was published in English, which claims priority under 35 U.S.C. §119(a)-(d) to Australian Patent Application No. 2003905222, filed Sep. 25, 2003. The content of this application is incorporated herein by reference in its entirety.

FIELD OF THE INVENTION

THIS INVENTION relates generally to pathogenic resistance. More particularly, the present invention relates to polynucleotide and polypeptide sequences involved in the resistance mechanism of plants to pathogens, especially fungal pathogens. The present invention also relates to the use of these sequences for modulating plant resistance and for producing genetically modified plants having modified pathogen resistance characteristics.

Bibliographic details of certain publications referred to by author in this specification are collected at the end of the description.

BACKGROUND OF THE INVENTION

Banana is one of the world's most important fruit crops with a world production of approximately 98 million tons annually (FAO, 2001). However, as with many monocultures, a range of fungal, viral, bacterial and nematode diseases affects banana, which cause severe economical losses every year.

*Fusarium* wilt is one of the most destructive and notorious diseases of banana. It is also known as Panama disease, in recognition of the extensive damage it caused in export plantations in this Central American country. By 1960, *Fusarium* wilt had destroyed an estimated 40,000 ha of 'Gros Michel' (AAA), causing the export industry to convert to cultivars in the Cavendish subgroup (AAA) (Ploetz and Pegg, 2000). *Fusarium* wilt is caused by the soilborne hyphomycete, *Fusarium oxysporum* Schlect. f sp. *cubense*. It is one of more than 120 formae speciales (special forms) of *F. oxysporum* that cause vascular wilts of flowering plants. This pathogen affects species of *Musa* and *Heliconia*, and strains have been classified into four physiological races based on pathogenicity to host cultivars in the field (race 1, 'Gros Michel'; race 2, 'Bluggoe'; race 3, *Heliconia* spp.; and race 4, Cavendish cultivars and all cultivars susceptible to race 1 and 2). Until recently, race 4 had only been recorded to cause serious losses in the subtropical regions of Australia, South Africa, the Canary Islands, and Taiwan. If this race were to become established in the Americas, the world export industries would be severely affected, as there is no widely accepted replacement for Cavendish cultivars (Bentley et al., 1998).

In general, effective chemical control measures do not exist. In work conducted in South Africa, methyl bromide significantly reduced disease incidence, but was effective for only three years due to recolonisation of the fumigated areas by the pathogen. Studies on the biological and cultural control of this disease have begun only recently. *Arbuscular mycorrhizal* fungi have been shown to reduce disease severity in short-term green house studies, but results from long term field studies have not been reported (Ortiz et al., 1995). Tissue-culture plantlets are free of pathogens and should be used to establish new plantings whenever possible. However the expense of plantlets may make their use in subsistence agriculture impractical. Genetic resistance offers the greatest opportunity for managing this disease in infested soils (Ortiz et al., 1995).

Plants recognise and resist many invading pathogens by inducing a rapid defense response, termed the hypersensitive response (HR). The HR results in localised cell and tissue death at the site of infection, which constrains further spread of the infection. This local response often triggers non-specific resistance throughout the plant, a phenomenon known as systemic acquired resistance (SAR). Once triggered, SAR provides resistance to a wide range of pathogens for days. The HR and SAR depend on interaction between a dominant or semidominant resistance gene (R) product in the plant and a corresponding dominant phytopathogen avirulence gene (Avr) product (Baker et al., 1997). A loss or alteration to either the plant R gene or the pathogen Avr gene leads to disease (compatibility) (Hammond-Kosack and Jones, 1997).

The R proteins provide resistance to pathogens as diverse as fungi, bacteria, viruses, nematodes and insects. Eight classes of R genes have been defined according to the structural characteristics of their predicted protein: (1) cytoplasmic toxin reductase enzymes; (2) intracellular protein kinases; (3) receptor kinase-like protein with two tandem protein kinase domain; (4) receptor-like protein kinases with an extracellular leucine-rich repeat (LRR) domain; (5) intracellular LRR proteins with a nucleotide binding site (NBS) and leucine zipper (LZ) motif; (6) intracellular NBS-LRR proteins with a region with similarity to the Toll and interleukin-1 receptor (TIR) proteins; (7) LRR proteins that encode membrane-bound extracellular proteins; and (8) LZ proteins that encode membrane-bound intracellular proteins (FIG. 1). With a few exceptions, all R genes have been cloned by a map-based cloning approach.

The NBS-LRR class is by far the largest group of resistance proteins with more than 30 cloned genes to date. Two subgroups within the NBS-LRR class have been recognised by the presence or absence of ah amino N-terminal region (TIR domain) with amino acid sequence similarity to the cytoplasmic signalling domains of the Toll and interleukin-1 receptors (Meyer et al., 1999; Pan et al., 2000).

The N-terminal of some NBS-LRR proteins is similar to the cytoplasmic effector domain of the *Drosophila melanogaster* and human TOLL and interleukin-1 receptors (the TIR domain)(Hammond-kosack and Jones, 1997). Other NIBS-LRR proteins have different N-terminal domains, which often contain putative leucine-zipper (LZ) motifs. Mutational analysis in *Arabidopsis* revealed that TIR-NBS-LRR and LZ-NBS-LRR proteins employ different signalling pathways. Proteins in the TIR effector domain signal via a pathway that includes EDS1, a predicted lipase, whereas most LZ-NBS-LRR proteins examined employ the membrane-associated NDR1 protein (Aarts et al., 1998). There is no apparent correlation between pathogen type and the NBS-LRR subclass used by plants to detect these pathogens (Ellis and Jones 1998). All this evidence is consistent with the hypothesis of Aarts et al., (1998), who suggested that there may be two downstream pathways triggered by R genes, with the structure of the R protein determining which downstream factors are required. Other recent results have shown that the situation may not be this simple. Two R genes from *Arabidopsis*, RPP8 and RPP13 (both LZ-NBS-LRR proteins), require neither EDS1 nor NDR1, suggesting that there is at least a third pathway for the transduction of R-gene signals (Glazebrook, 2001). Although many studies on different R genes have suggested that the R-protein LRR domain makes the major contribution to the unique recognition capacity of individual R genes, recent analyses of the L allelic series has shown that the TIR domain can also contribute to this capacity. Thus, it is possible that the LRR are necessary but not sufficient for the specific recognition of Avr proteins and that LRR and amino-terminal domains have co-evolved to function in a coordinate manner. (Zachary, 2001).

The central NBS domain comprises three motifs predicted to bind ATP or GTP, and several conserved motifs whose functions are not known (Hammond-Kosack and Jones, 1997). This region has homology to two activators of apoptosis in animal cells: APAF-1 and CED. By analogy to these well-characterised regulators of programmed cell death, the corresponding domain in NBS-LRR proteins might operate as an intramolecular signal transducer (Van der Biezen and Jones, 1998; Aravind et al., 1999). Domain swaps involving several flax L alleles reveal a requirement for intramolecular interactions and, thus, NBS-LRR proteins might serve as adaptor molecules that link recognition and signal delivery. For example, Avr signals perceived by the LRR might initiate nucleotide hydrolysis at the NBS domain. This might provide the energy necessary for a confrontational change in the NBS-LRR protein, exposing its N-terminal effector portion, to trigger a defense response (Van der Biezen and Jones, 1998).

LRR domain is thought to be involved in ligand-binding and pathogen recognition. LRR contain leucines or other hydrophobic residues at regular intervals and can also contain regularly spaced prolines and asparagines (Bent, 1996). Comparative analyses of the LRR domain show hypervariability, suggesting diversification due to selection pressures. This indicates that recognition specificity resides in this part of the LRR. By analyses of in vivo and in vitro generated recombinants between different flax L alleles, Ellis et al. (1997) confirmed experimentally that the LRR constitute the principal determinant of specificity for Avr products. Differential specificities of R proteins are often associated with duplications, deletions and sequence exchanges within the regions that encode the LRR. Recently, the LRR-like domain of the rice resistance protein Pita was shown to be required for interaction with Avr-Pita in the yeast two-hybrid system. Furthermore, mutation in either Avr-Pita Pita that abolished resistance also abolished the interaction in vitro. This is the first demonstrated interaction between an LRR-containing R protein and its cognate Avr protein (Jia et al., 2000).

Some of the resistance genes isolated to date have been transferred to susceptible cultivars of the same species or different species with successful results. For example, the N gene for resistance to Tobacco mosaic virus (TMV) has been transferred to tomato and gives resistance in this species to TMV (Whitham et al., 1996). The Bs2 gene, which encodes *Xanthomonas* resistance in pepper, has been cloned and transferred to tomato, a crop species in which the number of useful resistance genes to this pathogen is limited (Tai et al., 1999). However, the RPS2 gene from *Arabidopsis* is non-functional in transgenic tomato and this phenomenon has been referred to as 'restricted taxonomic functionality' (Tai et al., 1999). These data suggest that there may be difficulties in wide, cross-species resistance-gene transfer, in certain instances, due to R gene specificity Ellis et al., 2000).

The ability to isolate and transfer R genes eliminates the issue of retention of unwanted and genetically linked germoplasm, an important problem associated with classical breeding. Although disease-resistance transgenic plants are no yet available commercially, future product development seems likely as our current level of understanding of pathogenesis and plant defense improves (Stuiver and Custers 2002).

Despite the progress in R gene biology, however, no resistance genes have been isolated to date, which can confer resistance to destructive banana diseases in susceptible cultivars.

In work leading up to the present invention, four genotypes of banana were investigated to identify candidate R genes that would confer resistance to race 4 of *Fusarium oxysporum* fsp *cubense*. These genotypes were as follows: Cavendish, which is resistant to race 1 but susceptible to race 4; Calcutta 4, which is resistant to race 1 and race 4; three progeny of *Musa acuminata* spp *malaccensis*, which are susceptible to race 4; and three progeny of *Musa acuminata* spp *malaccensis*, which are resistant to race 4. Five families of R genes were identified from this investigation, all of which were present in the genomes of each of the genotypes but which had slightly different sequences. Surprisingly, two of these families (RGA2 and RGA5) were found to share some sequence similarity with the I2 R gene, which confers resistance to *Fusarium* wilt in tomatoes. In addition RGA2 was shown to be transcribed in the three resistant *Musa acuminata* spp *malaccensis* progeny but not in the three susceptible progeny. These discoveries have been reduced to practice in compositions and methods for modulating disease resistance, especially fungal resistance, in plants including banana and in plants and plant parts, especially genetically modified plants, plant cells, tissues and seeds, having modified disease resistance, as described hereafter.

SUMMARY OF THE INVENTION

Accordingly, in one aspect, the present invention provides isolated polynucleotides, which in some embodiments, confer disease resistance to a plant, especially resistance to diseases caused by fungal pathogens. These polynucleotides are generally selected from: (a) a polynucleotide comprising a nucleotide sequence that encodes a polypeptide conferring disease resistance to a plant, the sequence sharing at least 30% (and at least 31% to at least 99% and all integer percentages in between) sequence identity with the sequence set forth in SEQ ID NO: 1 or 3, or a complement thereof; (b) a polynucleotide comprising a portion at least 300 contiguous nucleotides in length of the sequence set forth in SEQ ID NO: 1 or 3 or of a complement of that sequence, wherein the portion encodes a polypeptide that confers disease resistance to a plant; (c) a polynucleotide comprising a nucleotide sequence that encodes a polypeptide comprising the amino acid sequence set forth in SEQ ID NO: 2 or 4; (d) a polynucleotide comprising a nucleotide sequence that encodes a portion at least 100 contiguous amino acid residues in length of the amino acid sequence set forth in SEQ ID NO: 2 or 4, wherein the portion confers disease resistance to a plant; (e) a polynucleotide comprising a nucleotide sequence that encodes a polypeptide that shares at least 50% (and at least 51% to at least 99% and all integer percentages in between) sequence similarity with at least a portion at least 300 contiguous amino acid residues in length of the sequence set forth in SEQ ID NO: 2 or 4, wherein the polypeptide confers disease resistance to a plant; (f) a polynucleotide comprising a nucleotide sequence that encodes a polypeptide that confers disease resistance to a plant, wherein the polynucleotide hybridises to the sequence of (a), (b), (c), (d), (e) or to a complement thereof, under at least low, medium or high stringency conditions; and (g) a polynucleotide comprising a portion at least 15 contiguous nucleotides in length of the sequence set forth in SEQ ID NO: 1 or 3, or of a complement of that sequence, wherein the portion hybridises to a sequence of (a), (b), (c), (d), (e) or to a complement thereof, under at least low, medium or high stringency conditions.

In another aspect, the present invention provides nucleic acid constructs for conferring disease resistance to a plant. These constructs generally comprise a polynucleotide as broadly described operably connected to a regulatory element, which is operable in the plant. In certain embodiments, the construct is in the form of a vector, especially an expression vector.

In yet another aspect, the present invention provides isolated host cells containing a nucleic acid construct as broadly described above. In certain advantageous embodiments, the host cells are plant cells. In some embodiments, the plant cells have the nucleic acid construct incorporated into their nucleome, especially stably incorporated into their genome.

In still another aspect, the present invention provides plants containing cells comprising a nucleic acid construct as broadly described above. In certain desirable embodiments, the plants have the nucleic acid construct stably incorporated into the nucleome, especially, the genome of their cells.

In a further aspect, the present invention provides probes for interrogating nucleic acid for the presence of a disease resistance-conferring polynucleotide or portion thereof. These probes generally comprise a nucleotide sequence that hybridises under at least low, medium or high stringency conditions to a polynucleotide as broadly described above. In some embodiments, the probes consist essentially of a nucleic acid sequence which corresponds or is complementary to at least a portion of a nucleotide sequence encoding the amino acid sequence set forth in SEQ ID NO: 2 or 4, wherein the portion is at least 15 nucleotides in length. In other embodiments, the probes comprise a nucleotide sequence that is capable of hybridising to at least a portion of a nucleotide sequence encoding the amino acid sequence set forth in SEQ ID NO: 2 or 4 under at least low, medium or high stringency conditions, wherein the portion is at least 15 nucleotides in length. In still other embodiments, the probes comprise a nucleotide sequence that is capable of hybridising to at least a portion of SEQ ID NO: 1 or 3 under at least low, medium or high stringency conditions, wherein the portion is at least 15 nucleotides in length.

Another aspect of the present invention provides methods for modulating, especially stimulating or enhancing, disease resistance in a plant. These methods generally comprise introducing a construct as broadly described above into the nucleome of the plant and regenerating stably transformed plants. In some embodiments, the construct is introduced into regenerable plant cells so as to yield transformed plant cells, which are suitably identified and selected, and which are subsequently used for regenerating differentiated plants. Typically, a transformed plant cell line is selected from the transformed plant cells for the differentiation of a genetically modified or transgenic plant. In some embodiments, the regenerable cells are regenerable dicotyledonous plant cells. In other embodiments, the regenerable cells are regenerable monocotyledonous plant cells such as regenerable graminaceous monocotyledonous plant cells and especially regenerable non-graminaceous monocotyledonous plant cells. In one example, the regenerable plant cells are regenerable banana cells. In certain advantageous embodiments, the expression of the polynucleotide that is operably linked to the regulatory element in the nucleic acid construct renders the differentiated transgenic plant with enhanced resistance to disease particularly diseases caused by fungal pathogens, especially soil borne fungi such as *Fusarium* species. Desirably, the nucleic acid construct is transmitted through a complete cycle of the differentiated transgenic plant to its progeny so that it is expressed by the progeny plants. Thus, the invention also provides seed, plant parts, tissue, and progeny plants derived from the differentiated transgenic plant.

In still another aspect, the invention contemplates conventional plant breeding methods to transfer genetic material corresponding to a polynucleotide as broadly described above via crossing and backcrossing to other plants, especially plants that are susceptible to a pathogenic disease, especially a disease caused by fungal pathogens such as species of *Fusarium*. In some embodiments, the genetic material will comprise naturally-occurring DNA that corresponds to a polynucleotide as broadly described above. Typically, these methods will comprise the steps of: (1) sexually crossing a plant containing that genetic material with a plant from a pathogen susceptible taxon; (2) recovering reproductive material from the progeny of the cross; and (3) growing plants with enhanced resistance to the disease from the reproductive material. In some embodiments, the methods will further comprise prior to step (1): identifying a plant that is resistant to the pathogenic disease by detecting expression in the plant of a polynucleotide as broadly described above. In certain advantageous embodiments, these methods will further comprise the steps of repetitively: (a) backcrossing the disease resistant progeny with disease susceptible plants from the susceptible taxon; and (b) selecting for expression of a nucleic acid sequence corresponding to a polynucleotide as broadly described above (or an associated marker gene) among the progeny of the backcross, until the desired characteristics of the susceptible taxon are present in the progeny along with the gene or genes imparting the pathogen resistance.

In another aspect of the invention, there is provided isolated polypeptides, which in some embodiments, confer disease resistance to a plant. These polypeptides are generally selected from: (i) a polypeptide comprising an amino acid sequence that shares at least 50% (and at least 51% to at least 99% and all integer percentages in between) similarity with the sequence set forth in SEQ ID NO: 2 or 4; (ii) a polypeptide comprising a portion at least 100 contiguous amino acid residues in length of the sequence set forth in SEQ ID NO: 2 or 4, wherein the polypeptide confers disease resistance to a plant; (iii) a polypeptide comprising an amino acid sequence that shares at least 30% (and at least 31% to at least 99% and all integer percentages in between) similarity with at least a portion of the sequence set forth in SEQ ID NO: 2 or 4, wherein the portion is at least 100 contiguous amino acid residues in length; and (iv) a polypeptide comprising at least a portion of the sequence set forth in SEQ ID NO: 2 or 4, wherein the portion is at least 5 contiguous amino acid residues in length and is immuno-interactive with an antigen-binding molecule that is immuno-interactive with a sequence selected from (i), (ii) or (iii).

In some embodiments, the polypeptide includes one or more and in some cases all of the following domains (the numbering refers to the consensus numbering in FIG. 2):

a domain which corresponds to residues 1-167 of FIG. 2. This domain may be structurally similar to a coiled coil. In some embodiments, this domain can have at least 60, 70, 80, 90, 95, or 98% (and all integer percentages in between) sequence similarity with, or have at least 30, 40, 50, 60, 70 or 80% (and all integer percentages in between) sequence identity to, or differ at no more than 1, 2, 3, 4, 5, 10, 15, 20, 25, 30 or 40 (and all integers in between) amino acid residues from, the corresponding domain of any of the sequences presented in FIG. 2;

a domain which corresponds to residues 168-536 of FIG. 2. This domain may be functionally analogous to a nuclear-binding site (NBS) domain. In some embodiments, this domain can have at least 70, 80, 90, 95, or 98% (and all integer percentages in between) sequence similarity with, or have at least 50, 60, 70, 80 or 90% (and all integer percentages in between) sequence identity to, or differ at no more than 1, 2, 3, 4, 5, 10, 15, 20, 25, 30 or 40 (and all integers in between) amino acid residues from, the corresponding domain of any of the sequences presented in FIG. 2; and a domain which corresponds to residues 537-1476 of FIG. 2. This domain may be functionally analogous to a leucine-rich repeat (LRR) domain. In some embodiments, this domain can have at least 60, 70, 80, 90, 95, or 98% (and all integer percentages in between) sequence similarity with, or have at least 30, 40, 50, 60, 70, 80 or 90% (and all integer percentages in between) sequence identity to, or differ at no more than 1, 2, 3, 4, 5, 10, 15, 20, 25, 30 or 40 (and all integers in between) amino acid residues from, the corresponding domain of any of the sequences presented in FIG. 2.

In some embodiments, it may be desirable to conserve one or more of the residues in the above regions, which residues are conserved between the sequences presented in FIG. 2, wherein the conserved amino acid residues correspond to identical residues or to residues belonging to the same class or subclass of amino acid residues.

In some embodiments, the domain corresponding to residues 1-167 of FIG. 2 comprises a sequence according to Formula (I): (SEQ ID NO: 05):

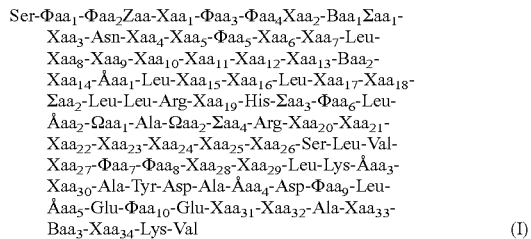

Ser-$\Phi aa_1$-$\Phi aa_2$-Zaa-$Xaa_1$-$\Phi aa_3$-$\Phi aa_4$-$Xaa_2$-$Baa_1$-$\Sigma aa_1$-$Xaa_3$-Asn-$Xaa_4$-$Xaa_5$-$\Phi aa_5$-$Xaa_6$-$Xaa_7$-Leu-$Xaa_8$-$Xaa_9$-$Xaa_{10}$-$Xaa_{11}$-$Xaa_{12}$-$Xaa_{13}$-$Baa_2$-$Xaa_{14}$-$Åaa_1$-Leu-$Xaa_{15}$-$Xaa_{16}$-Leu-$Xaa_{17}$-$Xaa_{18}$-$\Sigma aa_2$-Leu-Leu-Arg-$Xaa_{19}$-His-$\Sigma aa_3$-$\Phi aa_6$-Leu-$Åaa_2$-$\Omega aa_1$-Ala-$\Omega aa_2$-$\Sigma aa_4$-Arg-$Xaa_{20}$-$Xaa_{21}$-$Xaa_{22}$-$Xaa_{23}$-$Xaa_{24}$-$Xaa_{25}$-$Xaa_{26}$-Ser-Leu-Val-$Xaa_{27}$-$\Phi aa_7$-$\Phi aa_8$-$Xaa_{28}$-$Xaa_{29}$-Leu-Lys-$Åaa_3$-$Xaa_{30}$-Ala-Tyr-Asp-Ala-$Åaa_4$-Asp-$\Phi aa_9$-Leu-$Åaa_5$-Glu-$\Phi aa_{10}$-Glu-$Xaa_{31}$-$Xaa_{32}$-Ala-$Xaa_{33}$-$Baa_3$-$Xaa_{34}$-Lys-Val (I)

Wherein:

each of $\Phi_{1-10}$ is independently selected from any hydrophobic amino acid residue, Zaa is a neutral/polar amino acid residue, each of $\Sigma aa_{1-4}$ is independently selected from any small amino acid residue, each of $Baa_{1-3}$ is independently selected from any basic amino acid residue, each of $Åaa_{1-5}$ is independently selected from any acidic amino acid residue, each of $\Omega aa_{1-2}$ is independently selected from any charged amino acid residue, and $Xaa_{1-33}$ are each independently selected from any amino acid residue.

In some embodiments, Zaa is selected from Gln or Asn.

In some embodiments, $\Phi aa_1$ is selected from Phe or Leu. In some embodiments, $\Phi aa_2$ is selected from Ile or Val. In some embodiments, $\Phi aa_3$ is selected from Leu or Ile. In some embodiments, $\Phi aa_4$ is selected from Leu or Phe. In some embodiments, $\Phi aa_5$ is selected from Ile or Val. In some embodiments, $\Phi aa_6$ is selected from Ile or Leu. In some embodiments, $\Phi aa_7$ is selected from Leu or Trp. In some embodiments, $\Phi aa_8$ is selected from Val or Leu. In some embodiments, $\Phi aa_9$ is selected from Leu or Ile. In some embodiments, $\Phi aa_{10}$ is selected from Leu or Trp.

In some embodiments, $\Sigma aa_1$ is selected from Ala Ser. In some embodiments, $\Sigma aa_2$ is selected from Ser or Thr. In some embodiments, $\Sigma aa_3$ is selected from Ala Ser. In some embodiments, $\Sigma aa_4$ is selected from Thr or Ala.

In some embodiments, $Baa_1$ is selected from Lys or Arg. In some embodiments, $Baa_2$ is selected from H is or Arg. In some embodiments, $Baa_3$ is selected from Lys or Arg.

In some embodiments, each of $Åaa_{1-5}$ is independently selected from Asp or Glu.

In some embodiments, $\Omega aa_1$ is selected from Lys or Glu. In some embodiments, $\Omega aa_2$ is selected from Glu or Lys.

In some embodiments $Xaa_1$ is a small or acidic amino acid residue, e.g., $Xaa_1$ is selected from Thr or Glu. In some embodiments, $Xaa_2$ is an acidic or neutral/polar amino acid residue, e.g., $Xaa_2$ is selected from Asp or Asn. In some embodiments, $Xaa_3$ is a small or hydrophobic amino acid residue, e.g., $Xaa_3$ is selected from Ser or Ile. In some embodiments, $Xaa_4$ is a neutral/polar or hydrophobic amino acid residue, e.g., $Xaa_4$ is selected from Cys or Leu. In some embodiments, $Xaa_5$ is a small or hydrophobic amino acid residue, e.g., $Xaa_5$ is selected from Ala Ile. In some embodiments, $Xaa_6$ is a neutral/polar or small amino acid residue, e.g., $Xaa_6$ is selected from Gln or Ala. In some embodiments, $Xaa_7$ is a neutral/polar or acidic amino acid residue, e.g., $Xaa_7$ is selected from Gln or Glu. In some embodiments, $Xaa_8$ is a small or basic amino acid residue, e.g., $Xaa_8$ is selected from Ala Arg. In some embodiments, $Xaa_9$ is a basic or hydrophobic amino acid residue, e.g., $Xaa_9$ is selected from Arg or Leu.

In some embodiments, $Xaa_{10}$ is a basic or neutral/polar amino acid residue, e.g., $Xaa_{10}$ is selected from Arg or Gln. In some embodiments, $Xaa_{11}$ is a basic or hydrophobic amino acid residue, e.g., $Xaa_{11}$ is selected from Arg or Leu. In some embodiments, $Xaa_{12}$ is a small or neutral/polar amino acid residue, e.g., $Xaa_{12}$ is selected from Arg or Gln. In some embodiments, $Xaa_{13}$ is a hydrophobic or small amino acid residue, e.g., $Xaa_{13}$ is selected from Leu or Ala. In some embodiments, $Xaa_{14}$ is an acid or small amino acid residue, e.g., $Xaa_{14}$ is selected from Asp or Ala. In some embodiments, $Xaa_{15}$ is a basic or neutral/polar amino acid residue, e.g., $Xaa_{15}$ is selected from Arg or Asn. In some embodiments, $Xaa_{16}$ is a basic or neutral/polar amino acid residue, e.g., $Xaa_{16}$ is selected from Arg or Asn. In some embodiments, $Xaa_{17}$ is a basic or neutral/polar amino acid residue, e.g., $Xaa_{17}$ is selected from Arg or Gln. In some embodiments, $Xaa_{18}$ is a small or basic amino acid residue, e.g., $Xaa_{18}$ is selected from Thr or Arg. In some embodiments, $Xaa_{19}$ is a hydrophobic or small amino acid residue, e.g., $Xaa_{19}$ is selected from Ile or Thr.

In some embodiments, $Xaa_{20}$ is a hydrophobic or basic amino acid residue, e.g., $Xaa_{20}$ is selected from Trp or Arg. In some embodiments, $Xaa_{21}$ is absent or is a neutral/polar amino acid residue, e.g., Asn. In some embodiments, $Xaa_{22}$ is a basic or hydrophobic amino acid residue, e.g., $Xaa_{22}$ is selected from H is or Met. In some embodiments, $Xaa_{23}$ is a basic or small amino acid residue, e.g., $Xaa_{23}$ is selected from Lys or Thr. In some embodiments, $Xaa_{24}$ is a neutral/polar or acidic amino acid residue, e.g., $Xaa_{24}$ is selected from Asn or Asp. In some embodiments, $Xaa_{25}$ is a small or basic amino acid residue, e.g., $Xaa_{25}$ is selected from Thr or Lys. In some embodiments, $Xaa_{26}$ is an acidic or hydrophobic amino acid residue, e.g., $Xaa_{26}$ is selected from Glu or Leu. In some embodiments, $X_{27}$ is a basic or hydrophobic or amino acid residue, e.g., $Xaa_{27}$ is selected from Arg or Met. In some embodiments, $Xaa_{28}$ is a neutral/polar or acidic amino acid residue, e.g., $Xaa_{28}$ is selected from Gln or Glu. In some embodiments, $Xaa_{29}$ is a small or hydrophobic amino acid residue, e.g., $Xaa_{29}$ is selected from Ala Trp.

In some embodiments, $Xaa_{30}$ is a hydrophobic or small amino acid residue, e.g., $Xaa_{30}$ is selected from Tyr or Ala. In some embodiments, $Xaa_{31}$ is a neutral/polar or small amino acid residue, e.g., $Xaa_{31}$ is selected from Gln or Ala. In some embodiments, $Xaa_{32}$ is a small or hydrophobic amino acid residue, e.g., $Xaa_{32}$ is selected from Ala Ile. In some embodiments, $Xaa_{33}$ is a neutral/polar or hydrophobic amino acid residue, e.g., $Xaa_{33}$ is selected from Gln or Leu.

In some embodiments, the domain corresponding to residues 168-536 of FIG. 2 comprises a sequence according to Formula (II): (SEQ ID NO: 06):

Arg-$Xaa_1$-$Xaa_2$-Thr-$\Sigma aa_1$-Ser-$\Phi aa_1$-Leu-Thr-Glu-$\Sigma aa_2$-$Xaa_3$-$\Phi aa_2$-$\Phi aa_3$-Gly-Arg-$Xaa_4$-Gln-$Åaa_1$-$Baa_1$-Glu-$Xaa_5$-$\Phi aa_4$-$\Phi aa_5$-$\Omega aa_1$-Leu-Leu-Leu-$Åaa_2$-$\Sigma aa_3$-$\Sigma aa_4$-$Xaa_6$-Gly-$Xaa_7$-$Xaa_8$-$\Sigma aa_5$-Phe-$\Sigma aa_6$-Val-$\Phi aa_6$-Pro-$\Phi aa_7$-Val-Gly-$\Phi aa_8$-Gly-Gly-$Xaa_9$-Gly-Lys-Thr-Thr-Leu-$\Sigma aa_7$-Gln-Leu-$\Phi aa_9$-$\Phi aa_{10}$-Asn-Asp-$Xaa_{10}$-Arg-Val-$Xaa_{11}$-$Xaa_{12}$-$Xaa_{13}$-Phe-$Xaa_{14}$-Leu-$Baa_2$-$\Phi aa_{11}$-Trp-Val-Cys-Val-Ser-Asp-$Xaa_{15}$-Phe-$Xaa_{16}$-Val-Lys-Arg-$\Phi aa_{12}$-Thr-$Baa_3$-Glu-Ile-$Xaa_{17}$-Glu-$Xaa_{18}$-Ala-Thr-$Xaa_{19}$-$Xaa_{20}$-$\Omega aa_2$-$Xaa_{21}$-$Xaa_{22}$-Asp-$Xaa_{23}$-$Xaa_{24}$-Asn-Leu-$Xaa_{25}$-$Xaa_{26}$-Leu-Gln-$Xaa_{27}$-$Xaa_{28}$-Leu-Lys-Glu-$\Omega aa_3$-Ile-$Xaa_{29}$-$\Sigma aa_8$-$Xaa_{30}$-$Xaa_{31}$-Phe-Leu-Leu-Val-Leu-Asp-Asp-Val-Trp-$Xaa_{32}$-Glu-$Xaa_{33}$-$Xaa_{34}$-$Xaa_{35}$-$\Omega aa_4$-Trp-Glu-$Xaa_{36}$-Leu-$Xaa_{37}$-Ala-Pro-Leu-$\Omega aa_5$-$Xaa_{38}$-$\Sigma aa_9$-$\Sigma aa_{10}$-Arg-Gly-Ser-$Xaa_{39}$-Val-Ile-Val-Thr-Thr-$Xaa_{40}$-$Xaa_{41}$-$Xaa_{42}$-Lys-$\Phi aa_{13}$-Ala-$Xaa_{43}$-$\Phi aa_{14}$-$Xaa_{44}$-Gly-Thr-Met-$\Omega aa_6$-$Xaa_{45}$-$\Phi aa_{15}$-$Xaa_{46}$-Leu-$Åaa_3$-$Xaa_{47}$-Leu-$Xaa_{48}$-$Å_4$-Asp-$Xaa_{49}$-$Xaa_{50}$-Trp-$Xaa_{51}$-Leu-$\Phi aa_{16}$-$\omega aa_7$-$Xaa_{52}$-$Xaa_{53}$-$\Sigma aa_{11}$-Phe-$Xaa_{54}$-$Xaa_{55}$-$Xaa_{56}$-$Xaa_{57}$-$Xaa_{58}$-$\Sigma aa_{12}$-$Xaa_{59}$-$Xaa_{60}$-$Xaa_{61}$-$Xaa_{62}$-$\Omega aa_8$-$\Phi aa_{17}$-Glu-$Xaa_{63}$-Ile-Gly-Arg-Lys-Ile-Ala-$Xaa_{64}$-Lys-$\Phi aa_{18}$-$Xaa_{65}$-Gly-$Xaa_{66}$-Pro-$\Phi aa_{19}$-$\Sigma aa_{13}$-Ala-$Xaa_{67}$-$\Sigma aa_{14}$-$\Phi aa_{20}$-Gly-$Xaa_{68}$-$\Phi aa_{21}$-Leu-Arg-$Xaa_{69}$-$\Omega aa_9$-$Xaa_{70}$-$\Sigma aa_{15}$-$Xaa_{71}$-$Xaa_{72}$-$Xaa_{73}$-Trp-Arg-$Xaa_{74}$-$\Phi aa_{22}$-$\Phi aa_{23}$-Glu-$\Sigma aa_{16}$-Glu-$Xaa_{75}$-Trp-$Xaa_{76}$-$\Phi aa_{24}$-Pro-$Xaa_{77}$-Ala-$Xaa_{78}$-$Xaa_{79}$-$Åaa_5$-$\Phi_{25}$-Lue-$\Sigma aa_{17}$-$Xaa_{80}$-Leu-$Xaa_{81}$-$Xaa_{82}$-Ser-Tyr-$Xaa_{83}$-$Xaa_{84}$-Leu-Pro-$\Sigma aa_{18}$-$Xaa_{85}$-Leu-$Baa_4$-$Xaa_{86}$-Cys-Phe-Ala-Phe-Cys-Ala-$\Phi aa_{26}$-Phe-$Xaa_{87}$-Lys-$Xaa_{88}$-Tyr-$Xaa_{89}$-Phe-$Xaa_{90}$-Lys-$\Omega aa_{10}$-$Xaa_{91}$-Leu-Ile-$Xaa_{92}$-$Xaa_{93}$-Trp-Ile-Ala-$Xaa_{94}$-$Xaa_{95}$-$\Phi aa_{27}$-Ile    (II)

wherein:

each of $\Phi_{1-27}$ is independently selected from any hydrophobic amino acid residue, each of $\Sigma aa_{1-18}$ is independently selected from any small amino acid residue, each of $Baa_{1-4}$ is independently selected from any basic amino acid residue, each of $Åaa_{1-5}$ is independently selected from any acidic amino acid residue, each of $\Omega aa_{1-10}$ is independently selected from any charged amino acid residue, and $Xaa_{1-95}$ are each independently selected from any amino acid residue.

In some embodiments, $\Sigma aa_1$ is selected from Ser or Thr. In some embodiments, $\Sigma aa_2$ is selected from Thr or Ser. In some embodiments, $\Sigma aa_3$ is selected from Ser or Pro. In some embodiments, $\Sigma aa_4$ is selected from Gly or Ser. In some embodiments, $\Sigma aa_5$ is selected from Ser or Ala. In some embodiments, $\Sigma aa_6$ is selected from Ser or Pro. In some embodiments, $\Sigma aa_7$ is selected from Ala or Ser. In some embodiments, $\Sigma aa_8$ is selected from Ser or Gly. In some embodiments, $\Sigma aa_9$ is selected from Ala or Gly.

In some embodiments, $\Sigma aa_{10}$ is selected from Ala or Gly. In some embodiments, $\Sigma aa_{11}$ is selected from Ala or Ser. In some embodiments, $\Sigma aa_{12}$ is selected from Pro or Ser. In some embodiments, $\Sigma aa_{13}$ is selected from Ala or Gly. In some embodiments, $\Sigma aa_{14}$ is selected from Thr or Ala. In some embodiments, $\Sigma aa_{15}$ is selected from Ser or Gly. In some embodiments, $\Sigma aa_{16}$ is selected from Ser or Thr. In some embodiments, $\Sigma aa_{17}$ is selected from Pro or Ser. In some embodiments, $\Sigma aa_{18}$ is selected from Gly or Pro.

In some embodiments, $\Phi aa_{10}$ is selected from Phe or Leu. In some embodiments, $\Phi aa_2$ is selected from Val or Ile. In some embodiments, $\Phi aa_3$ is selected from Phe or Val. In some embodiments, $\Phi aa_4$ is selected from Val or Leu. In some embodiments, $\Phi aa_5$ is selected from Val or Ile. In some embodiments, $\Phi aa_6$ is selected from Leu or Val. In some embodiments, $\Phi aa_7$ is selected from Leu or Ile. In some embodiments, $\Phi aa_8$ is selected from Ile or Val. In some embodiments, $\Phi aa_9$ is selected from Val or Ile.

In some embodiments, $\Phi aa_{10}$ is selected from Tyr or Phe. In some embodiments, $\Phi aa_{11}$ is selected from Val or Met. In some embodiments, $\Phi aa_{12}$ is selected from Leu or Ile. In some embodiments, $\Phi aa_{13}$ is selected from Ile or Val. In some embodiments, $\Phi aa_{14}$ is selected from Ile or Val. In some embodiments, $\Phi aa_{15}$ is selected from Ile or Tyr. In some embodiments, $\Phi aa_{16}$ is selected from Phe or Ile. In some embodiments, $\Phi aa_{17}$ is selected from Leu or Met. In some embodiments, $\Phi aa_{18}$ is selected from Leu or Ile. In some embodiments, $\Phi aa_{19}$ is selected from Leu or Tyr.

In some embodiments, $\Phi aa_{20}$ is selected from Leu or Met. In some embodiments, $\Phi aa_{21}$ is selected from Leu or Tyr. In some embodiments, $\Phi aa_{22}$ is selected from Ile or Val. In some embodiments, $\Phi aa_{23}$ is selected from Met or Leu. In some embodiments, $\Phi aa_{24}$ is selected from Leu or Met. In some embodiments, $\Phi aa_{25}$ is selected from Ile or Val. In some embodiments, $\Phi aa_{26}$ is selected from Val or Leu. In some embodiments, $\Phi aa_{27}$ is selected from Phe or Leu.

In some embodiments, $Baa_{1-4}$ are each independently selected from Arg or Lys.

In some embodiments, each of $Åaa_{1-5}$ is independently selected from Asp or Glu.

In some embodiments, $\Omega aa_1$ is selected from Glu or Arg. In some embodiments, $\Omega aa_2$ is selected from Glu or Arg. In some embodiments, $\Omega aa_3$ is selected from Lys or Glu. In some embodiments, $\Omega aa_4$ is selected from Asp or Lys. In some embodiments, $\Omega aa_5$ is selected from Arg or Asp. In some embodiments, $\Omega aa_6$ is selected from Lys or Glu. In some embodiments, $\Omega aa_7$ is selected from Lys or Glu. In some embodiments, $\Omega aa_8$ is selected from Glu or Arg. In some embodiments, $\Omega aa_9$ is selected from Asp or Lys. In some embodiments, $\Omega aa_{10}$ is selected from H is or Asp.

In some embodiments $Xaa_1$ is a basic or small amino acid residue, e.g., $Xaa_1$ is selected from Arg or Gly. In some embodiments, $Xaa_2$ is an acidic or hydrophobic amino acid residue, e.g., $Xaa_2$ is selected from Glu or Val. In some embodiments, $Xaa_3$ is a hydrophobic or neutral/polar amino acid residue, e.g., $Xaa_3$ is selected from Val or Cys. In some embodiments, $Xaa_4$ is an acidic or small amino acid residue, e.g., $Xaa_4$ is selected from Asp or Ala. In some embodiments, $Xaa_5$ is a basic or neutral/polar amino acid residue, e.g., $Xaa_5$ is selected from Lys or Asn. In some embodiments, $Xaa_6$ is a small or acidic amino acid residue, e.g., $Xaa_6$ is selected from Ser or Asp. In some embodiments, $Xaa_7$ is absent or is a neutral/polar amino acid residue, e.g., Asn. In some embodiments, $Xaa_8$ is absent or is a small amino acid residue, e.g., Ser. In some embodiments, $Xaa_9$ is a hydrophobic or small amino acid residue, e.g., $Xaa_9$ is selected from Val or Ala.

In some embodiments, $Xaa_{10}$ is a neutral/polar or basic amino acid residue, e.g., $Xaa_{10}$ is selected from Asn or Lys. In some embodiments, $Xaa_{11}$ is a small or acidic amino acid residue, e.g., $Xaa_{11}$ is selected from Gly or Glu. In some embodiments, $Xaa_{12}$ is a neutral/polar or acidic amino acid residue, e.g., $Xaa_{12}$ is selected from Asn or Glu. In some embodiments, $Xaa_{13}$ is a hydrophobic or basic amino acid residue, e.g., $Xaa_{13}$ is selected from Tyr or His. In some embodiments, $Xaa_{14}$ is a basic or small amino acid residue, e.g., $Xaa_{14}$ is selected from His or Pro. In some embodiments, $Xaa_{15}$ is a neutral/polar or acidic amino acid residue, e.g., $Xaa_{15}$ is selected from Asn or Asp. In some embodiments, $Xaa_{16}$ is a neutral/polar or acidic amino acid residue, e.g., $Xaa_{16}$ is selected from Asn or Asp. In some embodiments, $Xaa_{17}$ is a hydrophobic or small amino acid residue, e.g., $Xaa_{17}$ is selected from Ile or Thr. In some embodiments, $Xaa_{18}$ is a small or hydrophobic amino acid residue, e.g., $Xaa_{18}$ is selected from Ser or Tyr. In some embodiments, $Xaa_{19}$ is a basic or neutral/polar amino acid residue, e.g., $Xaa_{19}$ is selected from Lys or Asn.

In some embodiments, $Xaa_{20}$ is a hydrophobic or small amino acid residue, e.g., $Xaa_{20}$ is selected from Val or Gly. In some embodiments, $Xaa_{21}$ is a neutral/polar or hydrophobic amino acid residue, e.g., $Xaa_{21}$ is selected from Gln or Phe. In some embodiments, $Xaa_{22}$ is a small or hydrophobic amino acid residue, e.g., $Xaa_{22}$ is selected from Ser or Met. In some embodiments, $Xaa_{23}$ is a basic or hydrophobic amino acid residue, e.g., $Xaa_{23}$ is selected from Lys or Leu. In some embodiments, $Xaa_{24}$ is a hydrophobic or small amino acid residue, e.g., $Xaa_{24}$ is selected from Leu or Thr. In some embodiments, $Xaa_{2}$ is an acidic or neutral/polar amino acid residue, e.g., $Xaa_{25}$ is selected from Asp or Asn. In some embodiments, $Xaa_{26}$ is a small or hydrophobic amino acid residue, e.g., $Xaa_{26}$ is selected from Thr or Met. In some embodiments, $Xaa_{27}$ is a neutral/polar or hydrophobic amino acid residue, e.g., $Xaa_{27}$ is selected from Gln or Val. In some embodiments, $Xaa_{28}$ is a hydrophobic or neutral/polar amino acid residue, e.g., $Xaa_{29}$ is selected from Ile or Asn. In some embodiments, $Xaa_{29}$ is a small or basic amino acid residue, e.g., $Xaa_{29}$ is selected from Ala or Arg.

In some embodiments, $Xaa_{30}$ is an acidic or small amino acid residue, e.g., $Xaa_{30}$ is selected from Glu or Thr. In some embodiments, $X_{31}$ is a basic or small amino acid residue, e.g., $Xaa_{31}$ is selected from Arg or Thr. In some embodiments, $Xaa_{32}$ is a small or neutral/polar amino acid residue, e.g., $Xaa_{32}$ is selected from Ser or Asn. In some embodiments, $Xaa_{33}$ is a neutral/polar or acidic amino acid residue, e.g., $Xaa_{33}$ is selected from Asn or Asp. In some embodiments, $Xaa_{34}$ is a basic or small amino acid residue, e.g., $Xaa_{34}$ is selected from Arg or Pro. In some embodiments, $Xaa_{35}$ is an acidic or hydrophobic amino acid residue, e.g., $Xaa_{35}$ is selected from Asp or Val. In some embodiments, $Xaa_{36}$ is a basic or small amino acid residue, e.g., $Xaa_{36}$ is selected from Arg or Ser. In some embodiments, $Xaa_{37}$ is a neutral/polar or hydrophobic amino acid residue, e.g., $Xaa_{37}$ is selected from Cys or Leu. In some embodiments, $Xaa_{38}$ is a hydrophobic or small amino acid residue, e.g., $Xaa_{38}$ is selected from Phe or Ala. In some embodiments, $Xaa_{39}$ is a basic or hydrophobic amino acid residue, e.g., $Xaa_{39}$ is selected from Lys or Val.

In some embodiments, $Xaa_{40}$ is a basic or neutral/polar amino acid residue, e.g., $Xaa_{40}$ is selected from Arg or Gln. In some embodiments, $X_{41}$ is an acidic or small amino acid residue, e.g., $Xaa_{41}$, is selected from Asp or Ser. In some embodiments, $Xaa_{42}$ is a small or basic amino acid residue, e.g., $Xaa_{42}$ is selected from Thr or Lys. In some embodiments, $Xaa_{43}$ is a small or acidic amino acid residue, e.g., $Xaa_{43}$ is selected from Ser or Asp. In some embodiments, $Xaa_{44}$ is a hydrophobic or small amino acid residue, e.g., $Xaa_{44}$ is selected from Ile or Thr. In some embodiments, $Xaa_{45}$ is an acidic or small amino acid residue, e.g., $Xaa_{45}$ is selected from Glu or Pro. In some embodiments, $Xaa_{46}$ is a small or hydrophobic amino acid residue, e.g., $Xaa_{46}$ is selected from Ser or Val. In some embodiments, $Xaa_{47}$ is a small or acidic amino acid residue, e.g., $Xaa_{47}$ is selected from Gly or Glu. In some embodiments, $Xaa_{48}$ is a neutral/polar or small amino acid residue, e.g., $Xaa_{48}$ is selected from Gln or Thr. In some embodiments, $Xaa_{49}$ is a small or acidic amino acid residue, e.g., $Xaa_{49}$ is selected from Ala or Asp.

In some embodiments, $Xaa_{50}$ is a hydrophobic or small amino acid residue, e.g., $Xaa_{50}$ is selected from Tyr or Ser. In some embodiments, $X_{51}$ is an acidic or small amino acid residue, e.g., $Xaa_{51}$ is selected from Glu or Ser. In some embodiments, $Xaa_{52}$ is a basic or small amino acid residue, e.g., $Xaa_{52}$ is selected from Lys or Ser. In some embodiments, $Xaa_{53}$ is a neutral/polar or basic amino acid residue, e.g., $Xaa_{53}$ is selected from Cys or His. In some embodiments, $Xaa_{54}$ is a small or basic amino acid residue, e.g., $Xaa_{54}$ is selected from Gly or Arg. In some embodiments, $Xaa_{55}$ is a small or acidic amino acid residue, e.g., $Xaa_{55}$ is selected from Ser or Glu. In some embodiments, $Xaa_{56}$ is a hydrophobic or small amino acid residue, e.g., $Xaa_{56}$ is selected from Val or Ala. In some embodiments, $Xaa_{57}$ is a neutral/polar or small amino acid residue, e.g., $Xaa_{57}$ is selected from Asn or Ser. In some embodiments, $Xaa_{58}$ is absent or is a neutral/polar amino acid residue, e.g., Cys. In some embodiments, $Xaa_{59}$ is a neutral/polar or small amino acid residue, e.g., $Xaa_{59}$ is selected from Gln or Ser.

In some embodiments, $Xaa_{60}$ is an acidic or small amino acid residue, e.g., $Xaa_{60}$ is selected from Glu or Pro. In some embodiments, $X_{61}$ is a basic or neutral/polar amino acid residue, e.g., $Xaa_{61}$ is selected from His or Asn. In some embodiments, $Xaa_{62}$ is a hydrophobic or small amino acid residue, e.g., $Xaa_{62}$ is selected from Leu or Pro. In some embodiments, $Xaa_{63}$ is a hydrophobic or acidic amino acid residue, e.g., $Xaa_{63}$ is selected from Val or Glu. In some embodiments, $Xaa_{64}$ is a small or basic amino acid residue, e.g., $Xaa_{64}$ is selected from Gly or Lys. In some embodiments, $Xaa_{65}$ is a basic or small amino acid residue, e.g., $Xaa_{65}$ is selected from Lys or Ser. In some embodiments, $Xaa_{66}$ is a small or hydrophobic amino acid residue, e.g., $Xaa_{66}$ is selected from Ser or Leu. In some embodiments, $Xaa_{67}$ is a basic or small amino acid residue, e.g., $Xaa_{67}$ is selected from Lys or Thr. In some embodiments, $Xaa_{68}$ is a small or basic amino acid residue, e.g., $Xaa_{68}$ is selected from Ser or Arg. In some embodiments, $Xaa_{69}$ is a hydrophobic or small amino acid residue, e.g., $Xaa_{69}$ is selected from Leu or Ser.

In some embodiments, $Xaa_{70}$ is a hydrophobic or basic amino acid residue, e.g., $Xaa_{70}$ is selected from Val or His. In some embodiments, $X_{71}$ is a neutral/polar or acidic amino acid residue, e.g., $Xaa_{71}$ is selected from Gln or Glu. In some embodiments, $Xaa_{72}$ is an acidic or small amino acid residue, e.g., $Xaa_{72}$ is selected from Glu or Ser. In some embodiments, $Xaa_{73}$ is a basic or small amino acid residue, e.g., $Xaa_{73}$ is selected from his or Ser. In some embodiments, $Xaa_{74}$ is a small or acidic amino acid residue, e.g., $Xaa_{74}$ is selected from Thr or Glu. In some embodiments, $Xaa_{75}$ is a hydrophobic or small amino acid residue, e.g., $Xaa_{75}$ is selected from Val or Thr. In some embodiments, $Xaa_{76}$ is a neutral/polar or acidic amino acid residue, e.g., $Xaa_{76}$ is selected from Gln or Glu. In some embodiments, $Xaa_{77}$ is a neural/polar or small amino acid residue, e.g., $Xaa_{77}$ is selected from Gln or Pro. In some embodiments, $Xaa_{78}$ is an acidic or small amino acid residue, e.g., $Xaa_{78}$ is selected from Glu or Ala. In some embodiments, $Xaa_{79}$ is a neutral/polar or small amino acid residue, e.g., $Xaa_{79}$ is selected from Asn or Ser. In some embodiments, $Xaa_{80}$ is a hydrophobic or small amino acid residue, e.g., $Xaa_{80}$ is selected from Val or Ala. In some embodiments, $X_{81}$ is a hydrophobic or basic amino acid residue, e.g., $Xaa_{81}$ is selected from Trp or Arg. In some embodiments, $Xaa_{82}$ is a hydrophobic or basic amino acid residue, e.g., $Xaa_{82}$ is selected from Leu or Arg. In some embodiments, $Xaa_{83}$ is a neutral/polar or acidic amino acid residue, e.g., $Xaa_{83}$ is selected from Gln or Asp. In some embodiments, $Xaa_{84}$ is a basic or neutral/polar amino acid residue, e.g., $Xaa_{84}$ is selected from H is or Asn. In some embodiments, $Xaa_{85}$ is a basic or neutral/polar amino acid residue, e.g., $Xaa_{85}$ is selected from H is or Gln. In some embodiments, $Xaa_{86}$ is a neutral/polar or hydrophobic amino acid residue, e.g., $Xaa_{86}$ is selected from Gln or Leu. In some embodiments, $Xaa_{87}$ is a basic or small amino acid residue, e.g., $Xaa_{87}$ is selected from H is or Thr. In some embodiments, $Xaa_{88}$ is an acidic or small amino acid residue, e.g., $Xaa_{88}$ is selected from Asp or Gly. In some embodiments, $Xaa_{89}$ is a hydrophobic or basic amino acid residue, e.g., $Xaa_{89}$ is selected from Leu or Arg.

In some embodiments, $Xaa_{90}$ is a hydrophobic or basic amino acid residue, e.g., $Xaa_{90}$ is selected from Tyr or Arg. In some embodiments, $Xaa_{91}$ is an acidic or small amino acid residue, e.g., $Xaa_{91}$ is selected from Glu or Thr. In some embodiments, $Xaa_{92}$ is a neutral/polar or basic amino acid residue, e.g., $Xaa_{92}$ is selected from Gln or His. In some embodiments, $Xaa_{93}$ is a small or hydrophobic amino acid residue, e.g., $Xaa_{93}$ is selected from Thr or Met. In some embodiments, $Xaa_{94}$ is an acidic or neutral/polar amino acid residue, e.g., $Xaa_{94}$ is selected from Glu or Gln. In some embodiments, $Xaa_{95}$ is a small or neutral/polar amino acid residue, e.g., $Xaa_{95}$ is selected from Gly or Asn.

In some embodiments, the domain corresponding to residues 537-1476 of FIG. 2 comprises a sequence according to Formula (III): (SEQ ID NO: 07):

Leu-$Xaa_1$-$\Omega aa_1$-$Xaa_2$-$\Omega aa_1$-Phe-$Baa_1$-$Xaa_3$-Leu-$Xaa_4$-Arg-Ile-$Baa_2$-Val-Leu-$Xaa_5$-$\Phi aa_2$-$Xaa_6$-$Xaa_7$-Cys-$Xaa_8$-$\Phi aa_3$-$Baa_3$-$Xaa_9$-Leu-Pro-$Xaa_{10}$-$Xaa_{11}$-$\Phi aa_4$-Gly-$Xaa_{12}$-Leu-$Xaa_{13}$-$Xaa_{14}$-Leu-Arg-Tyr-Leu-$Xaa_{15}$-$\Phi aa_5$-Ser-$Xaa_{16}$-Asn-$\Sigma aa_1$-$Xaa_{17}$-Ile-Gln-Arg-Leu-Pro-Glu-Ser-$\Phi aa_6$-$Xaa_{18}$-$\Omega aa_2$-Leu-$Xaa_{19}$-$Xaa_{20}$-Leu-Gln-$\Sigma aa_2$-Leu-$Xaa_{21}$-Leu-$Xaa_{22}$-Gly-Cys-$Xaa_{23}$-Leu-$Xaa_{24}$-$Xaa_{25}$-$\Phi aa_7$-Pro-$Xaa_{26}$-$\Sigma aa_3$-Met-Ser-$Baa_4$-Leu-$\Phi aa_8$-$Xaa_{27}$-Leu-Arg-Gln-Leu-$Baa_5$-$Xaa_{28}$-$Xaa_{29}$-$Xaa_{30}$-$\mathring{A}aa_1$-$\Phi aa_9$-Ile-$\Sigma aa_4$-$\Omega aa_3$-Ile-$Xaa_{31}$-$\Omega aa_4$-Val-Gly-$Baa_6$-Leu-Ile-$Xaa_{32}$-Leu-Gln-Glu-Leu-$Xaa_{33}$-Ala-$\Phi aa_{10}$-$Xaa_{34}$-Val-$Xaa_{35}$-$Xaa_{36}$-$Baa_7$-$Xaa_{37}$Gly-$Xaa_{38}$-$Xaa_{39}$-$\Phi aa_{11}$-Ala-Glu-Leu-Ser-$\Sigma aa_5$-$\Phi aa_{12}$-$Xaa_{40}$-Gln-Leu-$Baa_8$-$\Sigma aa_6$-$Xaa_{41}$-Leu-$Xaa_{42}$-Ile-$Xaa_{43}$-Asn-Leu-$Xaa_{44}$-Asn-Val-$Xaa_{45}$-$Xaa_{46}$-$Xaa_{47}$-$\Omega aa_5$-Glu-$\Sigma aa_7$-$Xaa_{48}$-Lys-Ala-$Baa_9$-Leu-$\Omega aa_6$-$\Omega aa_7$-Lys-Gln-$Xaa_{49}$-Leu-$\Omega aa_8$-$Xaa_{50}$-Leu-$\mathring{A}aa_2$-Leu-$\Omega aa_9$-Trp-Ala-$Xaa_{51}$-Gly-$Xaa_{52}$-$Xaa_{53}$-$Xaa_{54}$-$Xaa_{55}$-$Xaa_{56}$-$Xaa_{57}$-$Xaa_{58}$-Glu-$Xaa_{59}$-$Xaa_{60}$-$Xaa_{61}$-$Xaa_{62}$-$\Omega aa_{10}$-$\Omega_{11}$-Val-Leu-$Xaa_{64}$-Pro-His-$Xaa_{65}$-$Xaa_{66}$-Leu-$Baa_{10}$-$Xaa_{67}$-Leu-$\Sigma aa_8$-Ile-$Baa_{11}$-$Xaa_{68}$-Tyr-$\Sigma aa_9$-Gly-$\Sigma aa_{10}$-$\Sigma aa_{11}$-$Xaa_{69}$-Pro-Ser-Trp-$\Phi aa_{13}$-$Xaa_{70}$-$Xaa_{71}$-$Xaa_{72}$-$\Phi aa_{14}$-Leu-Pro-Asn-$\Phi aa_{15}$-$Xaa_{73}$-Thr-$\Phi aa_{16}$-$Baa_{12}$-Leu-$\Omega aa_{12}$-$Xaa_{74}$-Cys-$\Sigma aa_{12}$-Arg-Leu-$Xaa_{75}$-$Xaa_{76}$-Leu-$\Sigma aa_{13}$-$Xaa_{77}$-$\Phi aa_{17}$-Gly-Gln-Leu-$Xaa_{78}$-$Xaa_{79}$-Leu-$Baa_{13}$-$Xaa_{80}$-Leu-His-$\Phi aa_{18}$-$\Omega aa_{13}$-$Xaa_{81}$-Met-$\Sigma aa_{14}$-$Xaa_{82}$-Val-$Baa_{14}$-Gln-$\Phi aa_{19}$-$Xaa_{83}$-$Xaa_{84}$-$Xaa_{85}$-$\Phi aa_{20}$-$Xaa_{86}$-Gly-$Xaa_{87}$-$\Sigma aa_{15}$-$\Omega aa_{14}$-$Xaa_{88}$-$Xaa_{89}$-$Xaa_{90}$-Phe-Pro-$Xaa_{91}$-Leu-Glu-$X_{92}$-Leu-$Xaa_{93}$-$\Phi aa_{21}$-$\Omega aa_{15}$-$\Omega aa_{16}$-Met-Pro-$\Sigma aa_{16}$-Leu-$\Omega aa_{17}$-Glu-$\Phi aa_{22}$     (III)

wherein:

each of $\Phi_{1-22}$ is independently selected from any hydrophobic amino acid residue, each of $\Sigma aa_{1-16}$ is independently selected from any small amino acid residue, each of $Baa_{1-14}$ is independently selected from any basic amino acid residue, each of $\mathring{A}aa_{1-2}$ is independently selected from any acidic amino acid residue, each of $\Omega aa_{1-16}$ is independently selected from any charged amino acid residue, and $Xaa_{1-93}$ are each independently selected from any amino acid residue.

In some embodiments, $\Omega aa_1$ is selected from H is or Asp. In some embodiments, $\Omega aa_2$ is selected from Asp or Arg. In some embodiments, $\Omega aa_3$ is selected from Lys or Asp. In some embodiments, $\Omega aa_4$ is selected from Glu or Lys. In some embodiments, $\Omega aa_5$ is selected from Glu or Arg. In some embodiments, $\Omega aa_6$ is selected from H is or Asp. In some embodiments, $\Omega aa_7$ is selected from Arg or Glu. In some embodiments, $\Omega aa_8$ is selected from Glu or Lys. In some embodiments, $\Omega aa_9$ is selected from Glu or Arg.

In some embodiments, $\Omega aa_{10}$ is selected from Glu or Arg. In some embodiments, $\Omega aa_{11}$ is selected from Glu or Lys. In some embodiments, $\Omega aa_{12}$ is selected from Lys or Asp. In some embodiments, $\Omega aa_{13}$ is selected from Lys or Glu. In some embodiments, $\Omega aa_{14}$ is selected from Lys or Glu. In some embodiments, $\Omega aa_{15}$ is selected from Glu or Arg. In some embodiments, $\Omega aa_{16}$ is selected from Asp or Arg.

In some embodiments, $\Phi aa_1$ is selected from Leu or Met. In some embodiments, $\Phi aa_2$ is selected from Leu or Phe. In some embodiments, $\Phi aa_3$ is selected from Met or Ile. In some embodiments, $\Phi aa_4$ is selected from Ile or Val. In some embodiments, $\Phi aa_5$ is selected from Ile or Leu. In some embodiments, $\Phi aa_6$ is selected from Leu or Val. In some embodiments, $\Phi aa_7$ is selected from Phe or Leu. In some embodiments, $\Phi aa_8$ is selected from Ile or Leu. In some embodiments, $\Phi aa_9$ is selected from Ile or Val.

In some embodiments, $\Phi aa_{10}$ is selected from Phe or Tyr. In some embodiments, $\Phi aa_{11}$ is selected from Leu or Ile. In some embodiments, $\Phi aa_{12}$ is selected from Leu or Met. In some embodiments, $\Phi aa_{13}$ is selected from Leu or Met. In some embodiments, $\Phi aa_{14}$ is, selected from Met or Tyr. In some embodiments, $\Phi aa_{15}$ is selected from Leu or Met. In some embodiments, $\Phi aa_{16}$ is selected from Leu or Ile. In some embodiments, $\Phi aa_{17}$ is selected from Ile or Leu. In some embodiments, $\Phi aa_{18}$ is selected from Met or Ile. In some embodiments, $\Phi aa_{19}$ is selected from Met or Ile.

In some embodiments, $\Phi aa_{20}$ is selected from Leu or Phe. In some embodiments, $\Phi aa_{21}$ is selected from Leu or Ile. In some embodiments, $\Phi aa_{22}$ is selected from Phe or Trp.

In some embodiments, $Baa_1$, $Baa_{3-6}$ and $Baa_{9-14}$ are each independently selected from Arg or Lys. In some embodiments, $Baa_2$ and $Baa_8$ are each independently selected from H is or Arg. In some embodiments, $Baa_2$ is selected from H is or Lys.

In some embodiments, $\Sigma aa_1$ is selected from Ala or Thr. In some embodiments, $\Sigma aa_2$ is selected from Ala or Thr. In some embodiments, $\Sigma aa_3$ is selected from Gly or Ser. In some embodiments, $\Sigma aa_4$ is selected from Ser or Ala. In some embodiments, $\Sigma aa_5$ is selected from Gly or Ala. In some embodiments, $\Sigma aa_6$ is selected from Gly or Ser. In some embodiments, $\tau aa_7$ is selected from Ala or Ser. In some embodiments, $\Sigma aa_8$ is selected from Thr or Ser. In some embodiments, $\Sigma aa_9$ is selected from Ser or Gly.

In some embodiments, $\Sigma aa_{10}$ is selected from Ala or Thr. In some embodiments, $\Sigma aa_{11}$ is selected from Thr or Ser. In some embodiments, $\Sigma aa_{12}$ is selected from Thr or Ala. In some embodiments, $\Sigma aa_{13}$ is selected from Ser or Pro. In some embodiments, $Zaa_{14}$ is selected from Pro or Ser. In some embodiments, $\Sigma aa_{15}$ is selected from Thr or Gly. In some embodiments, $\Sigma aa_{16}$ is selected from Thr or Ser.

In some embodiments, each of $\mathring{A}aa_{1-2}$ is independently selected from Asp or Glu.

In some embodiments $Xaa_1$ is a small or hydrophobic amino acid residue, e.g., $Xaa_1$ is selected from Pro or Leu. In some embodiments, $Xaa_2$ is an small or basic amino acid residue, e.g., $Xaa_2$ is selected from Ser or Arg. In some embodiments, $Xaa_3$ is a basic or hydrophobic amino acid residue, e.g., $Xaa_3$ is selected from Arg or Met. In some embodiments, $Xaa_4$ is an basic or small amino acid residue, e.g., $Xaa_4$ is selected from Lys or Ser. In some embodiments, $Xaa_5$ is a hydrophobic or acidic amino acid residue, e.g., $Xaa_5$ is selected from Val or Asp. In some embodiments, $Xaa_5$ is a neutral/polar or small amino acid residue, e.g., $Xaa_6$ is selected from Gln or Ser. In some embodiments, $Xaa_7$ is a basic or neutral/polar amino acid residue, e.g., $Xaa_7$ is selected from Lys or Asn. In some embodiments, $Xaa_8$ is a small or hydrophobic amino acid residue, e.g., $Xaa_8$ is selected from Gly or Val. In some embodiments, $Xaa_9$ is an acidic or neutral/polar amino acid residue, e.g., $Xaa_9$ is selected from Glu or Asn.

In some embodiments, $Xaa_{10}$ is an acidic or small amino acid residue, e.g., $Xaa_{10}$ is selected from Asp or Ser. In some embodiments, $Xaa_{11}$ is a hydrophobic or small amino acid residue, e.g., $Xaa_{11}$ is selected from Ile or Ser. In some embodiments, $Xaa_{12}$ is an acidic or neutral/polar amino acid residue, e.g., $Xaa_{12}$ is selected from Asp or Asn. In some embodiments, $Xaa_{13}$ is a hydrophobic or basic amino acid residue, e.g., $Xaa_{13}$ is selected from Ile or Lys. In some embodiments, $Xaa_{14}$ is a neutral/polar or basic amino acid residue, e.g., $Xaa_{14}$ is selected from Gln or His. In some embodiments, $Xaa_{15}$ is acidic or small amino acid residue, e.g., $Xaa_{15}$ is selected from Asp or Gly. In some embodiments, $Xaa_{16}$ is absent or is a hydrophobic amino acid residue, e.g., Tyr. In some embodiments, $Xaa_{17}$ is a neutral/polar or basic amino acid residue, e.g., $Xaa_{17}$ is selected from Cys or Arg. In some embodiments, $Xaa_{18}$ is a neutral/polar or small amino acid residue, e.g., $Xaa_{18}$ is selected from Cys or Thr. In some embodiments, $Xaa_{19}$ is a hydrophobic or neutral/polar amino acid residue, e.g., $Xaa_{19}$ is selected from Tyr or Cys.

In some embodiments, $Xaa_{20}$ is a neutral/polar or hydrophobic amino acid residue, e.g., $Xaa_{20}$ is selected from Asn or Leu. In some embodiments, $Xaa_{21}$ is a basic or hydrophobic amino acid residue, e.g., $Xaa_{21}$ is selected from Arg or Leu. In some embodiments, $Xaa_{22}$ is a hydrophobic or acidic amino acid residue, e.g., $Xaa_{22}$ is selected from Trp or Glu. In some embodiments, $Xaa_{23}$ is a neutral/polar or acidic amino acid residue, e.g., $Xaa_{23}$ is selected from Gln or Glu. In some embodiments, $Xaa_{24}$ is a basic or neutral/polar amino acid residue, e.g., $Xaa_{24}$ is selected from Arg or Cys. In some embodiments, $Xaa_{25}$ is a small or basic amino acid residue, e.g., $Xaa_{25}$ is selected from Ser or Arg. In some embodiments, $Xaa_{26}$ is a neutral/polar or basic amino acid residue, e.g., $Xaa_{26}$ is selected from Gln or Arg. In some embodiments, $Xaa_{27}$ is a neutral/polar or basic amino acid residue, e.g., $Xaa_{27}$ is selected from Asn or Lys. In some embodiments, $Xaa_{28}$ is a hydrophobic or small amino acid residue, e.g., $Xaa_{28}$ is selected from Val or Ala. In some embodiments, $Xaa_{29}$ is an acidic or neutral/polar amino acid residue, e.g., $Xaa_{29}$ is selected from Glu or Asn.

In some embodiments, $Xaa_{30}$ is an acidic or small amino acid residue, e.g., $Xaa_{30}$ is selected from Asp or Pro. In some embodiments, $X_{31}$ is a hydrophobic or small amino acid residue, e.g., $Xaa_{31}$ is selected from Tyr or Ala. In some embodiments, $Xaa_{32}$ is a small or acidic amino acid residue, e.g., $Xaa_{32}$ is selected from Ser or Glu. In some embodiments, $Xaa_{33}$ is a small or basic amino acid residue, e.g., $Xaa_{33}$ is selected from Ser or Lys. In some embodiments, $Xaa_{34}$ is a basic or neutral/polar amino acid residue, e.g., $Xaa_{34}$ is selected from Lys or Asn. In some embodiments, $Xaa_{35}$ is an hydrophobic or acidic amino acid residue, e.g., $Xaa_{35}$ is selected from Leu or Asp. In some embodiments, $Xaa_{36}$ is a neutral/polar or basic amino acid residue, e.g., $Xaa_{36}$ is selected from Asn or His. In some embodiments, $Xaa_{37}$ is a neutral/polar or basic amino acid residue, e.g., $Xaa_{37}$ is selected from Asn or Lys. In some embodiments, $Xaa_{38}$ is a neutral/polar or basic amino acid residue, e.g., $Xaa_{38}$ is selected from Asn or Lys. In some embodiments, $Xaa_{39}$ is a basic or small amino acid residue, e.g., $Xaa_{39}$ is selected from Lys or Gly.

In some embodiments, $Xaa_{40}$ is a small or neutral/polar amino acid residue, e.g., $Xaa_{40}$ is selected from. Thr or Asp. In some embodiments, $X_{41}$ is an small or acidic amino acid residue, e.g., $Xaa_{41}$ is selected from Thr or Asp. In some embodiments, $Xaa_{42}$ is a basic or small amino acid residue, e.g., $Xaa_{42}$ is selected from Arg or Ser. In some embodiments, $Xaa_{43}$ is a small or basic amino acid residue, e.g., $Xaa_{43}$ is selected from Thr or Arg. In some embodiments, $Xaa_{44}$ is an acidic or neutral/polar amino acid residue, e.g., $Xaa_{44}$ is selected from Glu or Gln. In some embodiments, $Xaa_{45}$ is a small or acidic amino acid residue, e.g., $Xaa_{45}$ is selected from Gly or Glu. In some embodiments, $Xaa_{46}$ is a small or basic amino acid residue, e.g., $Xaa_{46}$ is selected from Ser or Lys. In some embodiments, $Xaa_{47}$ is a basic or small amino acid residue, e.g., $Xaa_{47}$ is selected from Lys or Thr. In some embodiments, $Xaa_{48}$ is a small or basic amino acid residue, e.g., $Xaa_{48}$ is selected from Ser or Arg. In some embodiments, $Xaa_{49}$ is a hydrophobic or basic amino acid residue, e.g., $Xaa_{49}$ is selected from Tyr or Lys.

In some embodiments, $Xaa_{50}$ is a small or hydrophobic amino acid residue, e.g., $Xaa_{50}$ is selected from Ala or Leu. In some embodiments, $X_{51}$ is a hydrophobic or acidic amino acid residue, e.g., $Xaa_{51}$ is selected from Ala or Asp. In some embodiments, $Xaa_{52}$ is a neutral/polar or basic amino acid residue, e.g., $Xaa_{52}$ is selected from Gln or Arg. In some embodiments, $Xaa_{53}$ is a hydrophobic or small amino acid residue, e.g., $Xaa_{53}$ is selected from Val or Gly. In some embodiments, $Xaa_{54}$ is absent or is a small amino acid residue, e.g., Ser. In some embodiments, $Xaa_{55}$ is absent or is a small amino acid residue, e.g., Ser. In some embodiments, $Xaa_{56}$ is absent or is a hydrophobic amino acid residue, e.g., Leu. In some embodiments, $Xaa_{57}$ is an acidic or hydrophobic amino acid residue, e.g., $Xaa_{57}$ is selected from Glu or Ala. In some embodiments, $Xaa_{58}$ is a basic or small amino acid residue, e.g., $Xaa_{58}$ is selected from H is or Gly. In some embodiments, $Xaa_{59}$ is a hydrophobic or neutral/polar amino acid residue, e.g., $Xaa_{59}$ is selected from Leu or Cys.

In some embodiments, $Xaa_{60}$ is a hydrophobic or acidic amino acid residue, e.g., $Xaa_{60}$ is selected from Leu or Asp. In some embodiments, $X_{61}$ is a hydrophobic or basic amino acid residue, e.g., $Xaa_{61}$ is selected from Val or Arg. In some embodiments, $Xaa_{62}$ is a small or acidic amino acid residue, e.g., $Xaa_{62}$ is selected from Ser or Asp. In some embodiments, $Xaa_{63}$ is a hydrophobic or basic amino acid residue, e.g., $Xaa_{63}$ is selected from Leu or Lys. In some embodiments, $Xaa_{64}$ is a neutral/polar or basic amino acid residue, e.g., $Xaa_{64}$ is selected from Gln or Arg. In some embodiments, $Xaa_{65}$ is a basic or small amino acid residue, e.g., $Xaa_{65}$ is selected from H is or Pro. In some embodiments, $Xaa_{66}$ is a hydrophobic or neutral/polar amino acid residue, e.g., $Xaa_{66}$ is selected from Phe or Asn. In some embodiments, $Xaa_{67}$ is a small or acidic amino acid residue, e.g., $Xaa_{67}$ is selected from Ser or Glu. In some embodiments, $Xaa_{68}$ is a small or hydrophobic amino acid residue, e.g., $Xaa_6$ is selected from Gly or Tyr. In some embodiments, $Xaa_{69}$ is a hydrophobic or small amino acid residue, e.g., $Xaa_{69}$ is selected from Val or Ser.

In some embodiments, $Xaa_{70}$ is an acidic or small amino acid residue, e.g., $Xaa_{70}$ is selected from Asp or Thr. In some embodiments, $X_{71}$ is a hydrophobic or acidic amino acid residue, e.g., $Xaa_{71}$ is selected from Val or Asp. In some embodiments, $Xaa_{72}$ is a basic or neutral/polar amino acid residue, e.g., $Xaa_{72}$ is selected from Lys or Gln. In some embodiments, $Xaa_{73}$ is a small or acidic amino acid residue, e.g., $Xaa_{73}$ is selected from Gly or Glu. In some embodiments, $Xaa_{74}$ is a neutral/polar or small amino acid residue, e.g., $Xaa_{74}$ is selected from Asn or Ser. In some embodiments, $Xaa_{75}$ is an acidic or small amino acid residue, e.g., $Xaa_{75}$ is selected from Glu or Thr. In some embodiments, $Xaa_{76}$ is a small or acidic amino acid residue, e.g., $Xaa_{76}$ is selected from Gly or Glu. In some embodiments, $Xaa_{77}$ is a hydrophobic or neutral/polar amino acid residue, e.g., $Xaa_{77}$ is selected from Tyr or Cys. In some embodiments, $Xaa_{78}$ is a hydrophobic or basic amino acid residue, e.g., $Xaa_{78}$ is selected from Phe or His. In some embodiments, $Xaa_{79}$ is a basic or hydrophobic amino acid residue, e.g., $Xaa_{79}$ is selected from His or Ile.

In some embodiments, $Xaa_{80}$ is a hydrophobic or basic amino acid residue, e.g., $Xaa_{80}$ is selected from Val or His. In some embodiments, $X_{81}$ is a small or hydrophobic amino acid residue, e.g., $Xaa_{81}$ is selected from Arg or Gly. In some embodiments, $Xaa_{82}$ is a hydrophobic or neutral/polar amino acid residue, e.g., $Xaa_{82}$ is selected from Val or Gln. In some embodiments, $Xaa_{83}$ is a small or neutral/polar amino acid residue, e.g., $Xaa_{83}$ is selected from Ser or Asn. In some embodiments, $Xaa_{84}$ is a basic or hydrophobic amino acid residue, e.g., $Xaa_{84}$ is selected from His or Leu. In some embodiments, $Xaa_{85}$ is a neutral/polar or acidic amino acid residue, e.g., $Xaa_{85}$ is selected from Gln or Glu. In some embodiments, $Xaa_{86}$ is a neutral/polar or hydrophobic amino acid residue, e.g., $Xaa_{86}$ is selected from Cys or Tyr. In some embodiments, $Xaa_{87}$ is a neutral/polar or small amino acid residue, e.g., $Xaa_{87}$ is selected from Cys or Thr. In some embodiments, $Xaa_{88}$ is a small or hydrophobic amino acid residue, e.g., $Xaa_{88}$ is selected from Ser or Val. In some embodiments, $Xaa_{89}$ is a basic or small amino acid residue, e.g., $Xaa_{89}$ is selected from Lys or Ser.

In some embodiments, $Xaa_{90}$ is a hydrophobic or small amino acid residue, e.g., $Xaa_{90}$ is selected from Leu or Gly. In some embodiments, $Xaa_{91}$ is a basic or hydrophobic amino acid residue, e.g., $Xaa_{91}$ is selected from Arg or Leu. In some embodiments, $Xaa_{92}$ is and acidic or hydrophobic amino acid residue, e.g., $Xaa_{92}$ is selected from Glu or Leu. In some embodiments, $Xaa_{93}$ is a hydrophobic or neutral/polar amino acid residue, e.g., $Xaa_{93}$ is selected from Val or Asn.

In yet another aspect, the invention provides isolated polynucleotides comprising a nucleotide sequence encoding at least one domain as broadly described above.

In still another aspect, the invention provides antigen-binding molecules that are specifically immuno-interactive with a polypeptide or portion as broadly described above.

BRIEF DESCRIPTION OF THE DRAWINGS

FIG. 2 is a diagrammatic representation showing an alignment of the amino acid sequences set forth in SEQ ID NO: 2 and 4 using ClustalW multiple alignment and the PAM250 similarity matrix as disclosed for example by Dayhoff et al. (1978) A model of evolutionary change in proteins. Matrices for determining distance relationships In M. O. Dayhoff, (ed.), Atlas of protein sequence and structure, Vol. 5, pp. 345-358, National Biomedical Research Foundation, Washington D.C.; and by Gonnet et al., 1992, *Science* 256(5062): 144301445.

TABLE A

BRIEF DESCRIPTION OF THE SEQUENCES

Figure 1:
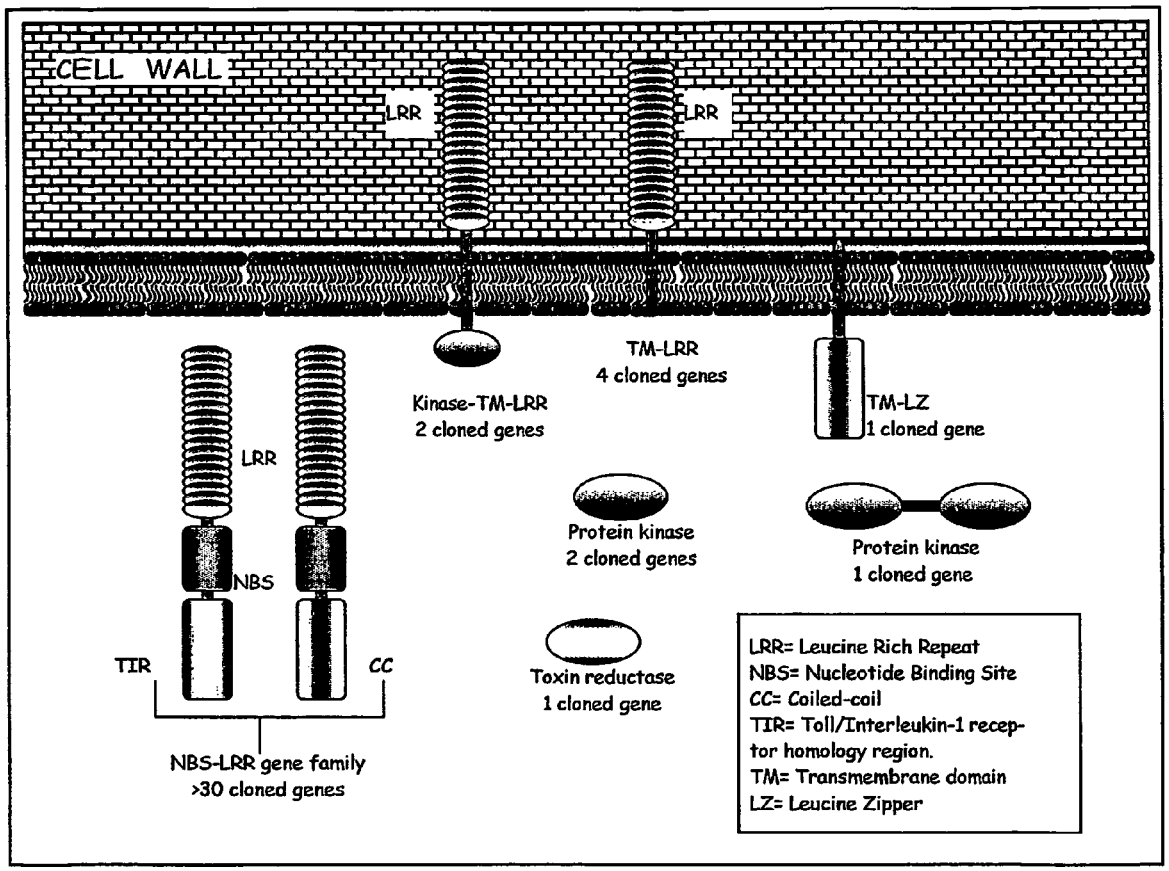
FIG. 1 is a schematic representation of the location and structure of the eight main classes of plant disease resistance proteins.

| SEQUENCE ID NUMBER | SEQUENCE | LENGTH |
| --- | --- | --- |
| SEQ ID NO: 1 | Nucleotide sequence of RGA5 obtained from Calcutta 4 | 4380 nts |
| SEQ ID NO: 2 | Deduced amino acid sequence encoded by SEQ ID NO: 1 | 1441 aa |
| SEQ ID NO: 3 | Nucleotide sequence of RGA2 obtained from *Musa acuminata* spp *malaccensis* | 3699 nts |
| SEQ ID NO: 4 | Deduced amino acid sequence encoded by SEQ ID NO: 1 | 1232 aa |

DETAILED DESCRIPTION OF THE INVENTION

1. Definitions

Unless stated otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. The following terms are defined below. These definitions are for illustrative purposes and are not intended to limit the common meaning in the art of the defined terms.

The articles "a" and "an" are used herein to refer to one or to more than one (i.e., to at least one) of the grammatical object of the article. By way of example, "an element" means one element or more than one element.

By "about" is meant a quantity, level, value, frequency, percentage, dimension, size, amount, weight or length that varies by as much as 30, 25, 20, 25, 10, 9, 8, 7, 6, 5, 4, 3, 2 or 1% to a reference quantity, level, value, frequency, percentage, dimension, size, amount, weight or length.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

As used herein, the term "binds specifically," "specifically immuno-interactive" and the like refers to antigen-binding molecules that bind or a immuno-interactive with the polypeptide or polypeptide portions of the invention but do not significantly bind to homologous prior art polypeptides.

By "biologically active portion" is meant a portion of a full-length parent peptide or polypeptide which portion retains an activity of the parent molecule. For example, a biologically active portion of polypeptide of the invention will retain the ability to confer disease resistance, especially resistance to fungal pathogens such as *Fusarium*. As used herein, the term "biologically active portion" includes deletion mutants and peptides, for example of at least about 8, 9, 10, 11, 12, 13, 14, 15, 16, 17, 18, 19, 20, 21, 22, 23, 24, 25, 30, 40, 50, 60, 70, 80, 90, 100, 120, 150, 300, 400, 500, 600, 700, 800, 900 or 1000 contiguous amino acids, which comprise an activity of a parent molecule. Portions of this type may be obtained through the application of standard recombinant nucleic acid techniques or synthesised using conventional liquid or solid phase synthesis techniques. For example, reference may be made to solution synthesis or solid phase synthesis as described, for example, in Chapter 9 entitled "*Peptide Synthesis*" by Atherton and Shephard which is included in a publication entitled "*Synthetic Vaccines*" edited by Nicholson and published by Blackwell Scientific Publications. Alternatively, peptides can be produced by digestion of a peptide or polypeptide of the invention with proteinases such as endoLys-C, endoArg-C, endoGlu-C and *staphylococcus* V8-protease. The digested fragments can be purified by, for example, high performance liquid chromatographic (HPLC) techniques. Recombinant nucleic acid techniques can also be used to produce such portions.

As used herein, the term "cis-acting sequence," "cis-acting element" or "cis-regulatory region" or "regulatory region" or similar term shall be taken to mean any sequence of nucleotides, which when positioned appropriately relative to an expressible genetic sequence, is capable of regulating, at least in part, the expression of the genetic sequence. Those skilled in the art will be aware that a cis-regulatory region may be capable of activating, silencing, enhancing, repressing or otherwise altering the level of expression and/or cell-type-specificity and/or developmental specificity of a gene sequence at the transcriptional or post-transcriptional level. In certain embodiments of the present invention, the cis-acting sequence is an activator sequence that enhances or stimulates the expression of an expressible genetic sequence.

Throughout this specification, unless the context requires otherwise, the words "comprise," "comprises" and "comprising" will be understood to imply the inclusion of a stated step or element or group of steps or elements but not the exclusion of any other step or element or group of steps or elements.

By "corresponds to" or "corresponding to" is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein.

As used herein, the terms "culturing", "culture" and the like refer to the set of procedures used in vitro where a population of cells (or a single cell) is incubated under conditions which have been shown to support the growth or maintenance of the cells in vitro. The art recognises a wide number of formats, media, temperature ranges, gas concentrations etc. which need to be defined in a culture system. The parameters will vary based on the format selected and the specific needs of the individual who practices the methods herein disclosed. However, it is recognised that the determination of culture parameters is routine in nature.

By "disease resistance" is intended that plants avoid or suppress the disease symptoms that are the outcome of plant-pathogen interaction. That is, pathogens are prevented from causing plant diseases and the associated disease symptoms. The methods of the invention can be utilised to protect plan from disease, particularly those diseases that are caused by plant pathogens, such as *Fusarium* wilt.

By "expression vector" is meant any autonomous genetic element capable of directing the transcription of a polynucleotide contained within the vector and suitably the synthesis of a peptide or polypeptide encoded by the polynucleotide. Such expression vectors are known to practitioners in the art.

The term "gene" as used herein refers to any and all discrete coding regions of the cell's genome, as well as associated non-coding and regulatory regions. The gene is also intended to mean the open reading frame encoding specific polypeptides, introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. The DNA sequences may be cDNA or genomic DNA or a fragment thereof. The gene may be introduced into an appropriate vector for extrachromosomal maintenance or for integration into the host.

The terms "growing" or "regeneration" as used herein mean growing a whole, differentiated plant from a plant cell, a group of plant cells, a plant part (including seeds), or a plant piece (e.g., from a protoplast, callus, or tissue part).

"Hybridisation" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridisation potential of paired nucleotides in complementary nucleic acid strands. Matched nucleotides hybridise efficiently, such as the classical A-T and G-C base pair mentioned above. Mismatches are other combinations of nucleotides that do not hybridise efficiently.

Reference herein to "immuno-interactive" includes reference to any interaction, reaction, or other form of association between molecules and in particular where one of the molecules is, or mimics, a component of the immune system.

By "isolated" is meant material that is substantially or essentially free from components that normally accompany it in its native state. For example, an "isolated polynucleotide", as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell, i.e., it is not associated with in vivo substances.

By "marker gene" is meant a gene that imparts a distinct phenotype to cells expressing the marker gene and thus allows such transformed cells to be distinguished from cells that do not have the marker. A selectable marker gene confers a trait for which one can 'select' based on resistance to a selective agent (e.g., a herbicide, antibiotic, radiation, heat, or other treatment damaging to untransformed cells). A screenable marker gene (or reporter gene) confers a trait that one can identify through observation or testing, i.e., by 'screening' (e.g., β-glucuronidase, luciferase, or other enzyme activity not present in untransformed cells).

As used herein, a "naturally-occurring" nucleic acid molecule refers to an RNA or DNA molecule having a nucleotide sequence that occurs in nature. For example a naturally-occurring nucleic acid molecule can encode a natural protein.

By "obtained from" is meant that a sample such as, for example, a nucleic acid extract or polypeptide extract is isolated from, or derived from, a particular source. For example, the extract may be isolated directly from plants, especially monocotyledonous plants and more especially non-graminaceous monocotyledonous plants such as banana.

The term "oligonucleotide" as used herein refers to a polymer composed of a multiplicity of nucleotide residues (deoxyribonucleotides or ribonucleotides, or related structural variants or synthetic analogues thereof, including nucleotides with modified or substituted sugar groups and the like) linked via phosphodiester bonds (or related structural variants or synthetic analogues thereof). Thus, while the term "oligonucleotide" typically refers to a nucleotide polymer in which the nucleotide residues and linkages between them are naturally-occurring, it will be understood that the term also includes within its scope various analogues including, but not restricted to, peptide nucleic acids (PNAs), phosphorothioate, phosphorodithioate, phosphoroselenoate, phosphorodiselenoate, phosphoroanilothioate, phosphoraniladate, phosphoroamidate, methyl phosphonates, 2-O-methyl ribonucleic acids, and the like. The exact size of the molecule can vary depending on the particular application. Oligonucleotides are a polynucleotide subset with 200 bases or fewer in length. Preferably, oligonucleotides are 10 to 60 bases in length and most preferably 12, 13, 14, 15, 16, 17, 18, 19, or 20 to 40 bases in length. Oligonucleotides are usually single stranded, e.g., for probes; although oligonucleotides may be double stranded, e.g., for use in the construction of a variant nucleic acid sequence. Oligonucleotides of the invention can be either sense or antisense oligonucleotides.

The term "operably connected" or "operably linked" as used herein means placing a structural gene under the regulatory control of a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the genes from which it is derived.

The term "pathogen" is used herein in its broadest sense to refer to an organism or an infectious agent whose infection of cells of viable plant tissue elicits a disease response.

The term "polynucleotide" or "nucleic acid" as used herein designates mRNA, RNA, cRNA, cDNA or DNA. The term typically refers polymeric form of nucleotides of at least 10 bases in length, either ribonucleotides or deoxynucleotides or a modified form of either type of nucleotide. The term includes single and double stranded forms of DNA.

The terms "polynucleotide variant" and "variant" refer to polynucleotides displaying substantial sequence identity with a reference polynucleotide sequence or polynucleotides that hybridise with a reference sequence under stringent conditions that are defined hereinafter. These terms also encompass polynucleotides that vary from a reference polynucleotide by addition, deletion or substitution of at least one nucleotide. In this regard, it is well understood in the art, for example, that certain alterations inclusive of mutations, additions, deletions and substitutions can be made to a reference polynucleotide whereby the altered polynucleotide retains a biological function or activity of the reference polynucleotide. The terms "polynucleotide variant" and "variant" also include naturally-occurring allelic variants.

"Polypeptide," "peptide" and "protein" are used interchangeably herein to refer to a polymer of amino acid residues and to variants and synthetic analogues of the same. Thus, these terms apply to amino acid polymers in which one or more amino acid residues is a synthetic non-naturally-occurring amino acid, such as a chemical analogue of a corresponding naturally-occurring amino acid, as well as to naturally-occurring amino acid polymers.

The term "polypeptide variant" refers to polypeptides which are distinguished from a reference polypeptide by the addition, deletion or substitution of at least one amino acid residue. In certain embodiments, one or more amino acid residues of a reference polypeptide are replaced by different amino acids. It is well understood in the art that some amino acids may be changed to others with broadly similar properties without changing the nature of the activity of the polypeptide (conservative substitutions) as described hereinafter.

By "primer" is meant an oligonucleotide which, when paired with a strand of DNA, is capable of initiating the synthesis of a primer extension product in the presence of a suitable polymerising agent. The primer is preferably single-stranded for maximum efficiency in amplification but can alternatively be double-stranded. A primer must be sufficiently long to prime the synthesis of extension products in the presence of the polymerisation agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotide residues, although it can contain fewer nucleotide residues. Primers can be large polynucleotides, such as from about 35 nucleotides to several kilobases or more. Primers can be selected to be "substantially complementary" to the sequence on the template to which it is designed to hybridise and serve as a site for the initiation of synthesis. By "substantially complementary", it is meant that the primer is sufficiently complementary to hybridise with a target polynucleotide. Desirably, the primer contains no mismatches with the template to which it is designed to hybridise but this is not essential. For example, non-complementary nucleotide residues can be attached to the 5' end of the primer, with the remainder of the primer sequence being complementary to the template. Alternatively, non-complementary nucleotide residues or a stretch of non-complementary nucleotide residues can be interspersed into a primer, provided that the primer sequence has sufficient complementarity with the sequence of the template to hybridise therewith and thereby form a template for synthesis of the extension product of the primer.

"Probe" refers to a molecule that binds to a specific sequence or sub-sequence or other moiety of another molecule. Unless otherwise indicated, the term "probe" typically refers to a polynucleotide probe that binds to another polynucleotide, often called the "target polynucleotide", through complementary base pairing. Probes can bind target polynucleotides lacking complete sequence complementarity with the probe, depending on the stringency of the hybridisation conditions. Probes can be labelled directly or indirectly.

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "recombinant polypeptide" is meant a polypeptide made using recombinant techniques, i.e., through the expression of a recombinant or synthetic polynucleotide.

By "regulatory element" or "regulatory element" is meant nucleic acid sequences (e.g., DNA) necessary for expression of an operably linked coding sequence in a particular host cell. The regulatory sequences that are suitable for prokaryotic cells for example, include a promoter, and optionally a cis-acting sequence such as an operator sequence and a ribosome binding site. Control sequences that are suitable for eukaryotic cells include promoters, polyadenylation signals, transcriptional enhancers, translational enhancers, leader or trailing sequences that modulate mRNA stability, as well as targeting sequences that target a product encoded by a transcribed polynucleotide to an intracellular compartment within a cell or to the extracellular environment.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, H is, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software.

"Similarity" refers to the percentage number of amino acids that are identical or constitute conservative substitutions as defined in Table B infra. Similarity may be determined using sequence comparison programs such as GAP (Deveraux et al. 1984, *Nucleic Acids Research* 12, 387-395). In this way, sequences of a similar or substantially different length to those cited herein might be compared by insertion of gaps into the alignment, such gaps being determined, for example, by the comparison algorithm used by GAP.

Terms used to describe sequence relationships between two or more polynucleotides or polypeptides include "reference sequence," "comparison window," "sequence identity," "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerised implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology", John Wiley & Sons Inc, 1994-1998, Chapter 15.

By the term "taxon" herein is meant a unit of botanical classification. It thus includes, genus, species, cultivars, varieties, variants and other minor taxonomic groups which lack a consistent nomenclature.

The term "transformation" means alteration of the genotype of an organism, for example a bacterium, yeast or plant, by the introduction of a foreign or endogenous nucleic acid.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector can also include a selection marker such as an antibiotic resistance gene that can be used for selection of suitable transformants. Examples of such resistance genes are known to those of skill in the art.

2. Modulation of Disease Resistance

The invention is drawn to polynucleotides, polypeptides and methods for modulating disease resistance: especially for stimulating or enhancing disease resistance in plants, caused by pathogens. Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include:

Soybeans: *Phytophthora megasperma* fsp. *glycinea*, *Macrophomina phaseolina*, *Rhizoctonia solani*, *Scierotinia scle-* rotiorum, Fusarium oxysporum, Diaporthe phaseolorum var. sojae (Phomopsis sojae), Diaporthe phaseolorum var. caulivora, Sclerotium rolfsii, Cercospora kikuchii, Cercospora sojina, Peronospora manshurica, Colletotrichum dematium (Colletotichum truncatum), Corynespora cassiicola, Septoria glycines, Phyllosticta sojicola, Alternaria alternata, Pseudomonas syringae p.v. glycinea, Xanthomonas campestris p.v. phaseoli, Microsphaera diffusa, Fusarium semitectum, Phialophora gregata, Soybean mosaic virus, Glomerella glycines, Tobacco Ring spot virus, Tobacco Streak virus, Phakopsorapachyrhizi, Pythium aphamidennatuin, Pythium ultimum, Pythium debaryanum, Tomato spotted wilt virus, Heterodera glycines Fusarium solani;

Canola: Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata;

Alfalfa: Clavibater michiganese subsp. insidiosum, Pythium ultimum, Pythium irregulare, Pythium splendens, Pythium debaryanum, Pythium aphamidernatum, Phytophthora megasperma, Peronospora trifoliorum, Phoma medicaginis var. medicaginis, Cercospora medicaginis, Pseudopeziza medicaginis, Leptotrochila medicaginis, Fusarium, Xanthomonas campestris p.v. alfalfae, Aphanomyces euteiches, Stemphylium herbarum, Stemphylium alfalfae;

Wheat: Pseudomonas syringae p.v. atrofaciens, Urocystis agropyri, Xanthomonas campestris p.v. translucens, Pseudomonas syringae p.v. syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis f.sp. tritici, Puccinia graminis f.sp. tritici, Puccinia recondita fsp. tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis var. tritici, Pythium aphamidermatum, Pythium arrhenomanes, Pythium ultimum, Bipolaris sorokiniana, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, Claviceps purpurea, Tilletia tritici, Tilletia laevis, Ustilago tritici, Tilletia indica, Rhizoctonia solani, Pythium arrhenomannes, Pythium gramicola, Pythium aphamidermatum, High Plains Virus, European wheat striate virus;

Sunflower: Plasmophora halstedii, Sclerotinia sclerotiorum, Aster Yellows, Septoria helianthi, Phomopsis helianthi, Alternaria helianthi, Alternaria zinniae, Botiytis cinerea, Phoma macdonaidii, Macrophonmina phaseolina, Eiysiphe cichoracearuni, Rhizopus oryzae, Rhizopus arrhizus, Rhizopus stolonifer, Puccinia helianthi, Verticillium dahliae, Erwinia carotovorum pv. carotovora, Cephalosporium acremorium, Phytophthora cryptogea, Albugo tragopogonis;

Corn: Fusarium moniliforme var. subglutinans, Erwinia stewartii, Fusarium moniliforme, Gibberella zeae (Fusarium graminearum), Stenocarpella maydi (Diplodia maydis), Pythium irregulare, Pythium debaryanum, Pythium graminicola, Pythium splendens, Pythium ultimum, Pythium aphamidermatum, Aspergillus flavus, Bipolaris maydis O, T (Cochliobolus heterostrophus), Helminthosporiun carbonum I, II & III (Cochliobolus carbonum), Exserohilum turcicum I, II & II, Helminthosporium pedicellatum, Physodenna maydis, Phyllosticta maydis, Kabatiella-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense subsp. nebraskense, Trichoderma viride, Maize Dwarf Mosaic Virus A & B, Wheat Streak Mosaic Virus, Maize Chlorotic Dwarf Virus, Claviceps sorghi, Pseudonomas avenae, Erwinia chrysanthemi pv. zea, Erwinia carotovora, Corn stunt spiroplasma, Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium, Maize Chlorotic Mottle Virus, High Plains Virus, Maize Mosaic Virus, Maize Rayado Fino Virus, Maize Streak Virus, Maize Stripe Virus, Maize Rough Dwarf Virus;

Sorghum: Exserohilum turcicum, Colletotrichum graminicola (Glomerella graminicola), Cercospora sorghi, Gloeocercospora sorghi, Ascochyta sorghina, Pseudomonas syringae p.v. syringae, Xanthomonas campestris p.v. holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi, Sugarcane mosaic H, Maize Dwarf Mosaic Virus A & B, Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola, etc.

Nematodes include parasitic nematodes such as root-knot, cyst, lesion, and reniform nematodes, etc Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include:

Maize: Ostrinia nubilalis, European corn borer; Agrotis ipsilon, black cutworm; Helicoverpa zea, corn earworm; Spodoptera frugiperda, fall armyworm; Diatraea grandiosella, southwestern corn borer; Elasmopalpus lignosellus, lesser cornstalk borer, Diatraea saccharalis, sugarcane borer, Diabrotica virgifera, western corn rootworm; Diabrotica lonigicornis barberi, northern corn rootworm; Diabrotica undecimpunctata howardi, southern corn rootworm; Melanotus spp., wireworms; Cyclocephala borealis, northern masked chafer (white grub); Cyclocephala iminaculata, southern masked chafer (white grub); Popillia japonica, Japanese beetle; Chaetocinema pulicaria, corn flea beetle; Sphenophorus maidis, maize billbug; Rhopalosiphun maidis, corn leaf aphid; Anuraphis maidiradicis, corn root aphid; Blissus leucopterus leucopterus, chinch bug; Melanoplusfemurrubrum, redlegged grasshopper, Melanoplus sanguinipes, migratory grasshopper; Hylemya platura, seedcorn maggot; Agromyza parvicornis, corn blot leafminer; Anaphothrips obscrurus, grass thrips; Solenopsis milesta, thief ant; Tetranychus urticae, twospotted spider mite;

Sorghum: Chilo partellus, sorghum borer; Spodoptera fugiperda, fall armyworm; Helicoverpa zea, corn earworm; Elasmopalpus lignosellus, lesser cornstalk borer, Feltia subterranea, granulate cutworm; Phyllophaga crinita, white grub; Eleodes, Conoderus, and Aeolus spp., wireworms; Oulema melanopus, cereal leaf beetle; Chaetocnema pulicaria, corn flea beetle; Sphenophorus maidis, maize billbug; Rhopalosiphum maidis; corn leaf aphid; Sipha flava, yellow sugarcane aphid; Blissus leucopterus leucopterus, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid, *Melanoplus femurrubrum*, redlegged grasshopper; *Melanoplus differentialis*, differential grasshopper, *Melanoplus sanguinipes*, migratory grasshopper, *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplusfemurrubrum*, redlegged grasshopper, *Melanoplus differentialis*, differential grasshopper, *Thrips tabaci*, onion thrips; *Franklinkiella fusca*, tobacco thrips; *Tetranychus cinnabarinus*, carmine spider mite; *Tetranychus urticae*, twospotted spider mite;

Rice: *Diatraea saccharalis* sugarcane borer; *Spodoptera frugiperda*, fall armyworm; *Helicoverpa zea*, corn earworm; *Colaspis brunnea*, grape *colaspis; Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug;

Soybean: *Pseudoplusia includens*, soybean looper; *Anticarsia gemmatalis*, velvetbean caterpillar, *Plathypena scabra*, green cloverworm; *Ostyinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplusl femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite;

Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servos*, brown stink bug; *Delia platura*, seedcorn maggot; *Mayetiola destructor*, Hessian fly, *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

In certain embodiments, the plant pathogen is selected from fungi, especially soil borne fungi such as *Fusarium oxysporum*, *Verticillium dahliae*, *Cladosporium* and *Ralstona Solanaceum*.

3. Polynucleotides of the Invention

The present invention is predicated, in part, on the isolation of two novel R genes from banana, one from *Musa acuminata* Calcutta 4 and the other from *Musa acuminata* spp *malaccensis*. The Calcutta 4 gene designated RGA5 is 4380 nts long and comprises a single open reading frame of 4321 nts that encodes a 1441-aa putative polypeptide product. The nucleotide sequence of this gene and its deduced polypeptide sequence are presented in SEQ ID NO: 1 and 2, respectively. The *Musa acuminata* spp *malaccensis* gene designated RGA2 comprises a single open reading frame of 3699 nts, which encodes a putative polypeptide product of 1232 aa. The nucleotide sequence of the RGA2 gene and its deduced polypeptide sequence are presented in SEQ ID NO: 3 and 4, respectively.

In accordance with the present invention, the novel R genes will be useful for facilitating the construction of crop plants that are resistant to pathogenic disease, especially disease caused by fungal pathogens, viruses, nematodes, insects and the like. The R genes of the present invention can also be used as markers in genetic mapping as well as in assessing disease resistance in a plant of interest. Thus, the sequences can be used in breeding programs. See, for example, Gentzbittel et al. (1998, *Theor. Appl. Genet.* 96:519-523). Additional uses for the sequences of the invention include using the sequences as bait to isolate other signalling components on defense/resistance pathways and to isolate the corresponding promoter sequences. The sequences may also be used to modulate plant development processes, such as pollen development, regulation of organ shape, differentiation of aleurone and shoot epidermis, embryogenic competence, and cell/cell interactions. See, generally, Sambrook et al. (1989) Molecular Cloning: A Laboratory Manual (2nd ed., Cold Spring Harbor Laboratory Press, Plainview, N.Y.). The sequences of the present invention can also be used to generate variants (e.g., by 'domain swapping') for the generation of new resistance specificities.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified polynucleotide or polypeptide is substantially free of other cellular material, or culture medium when produced by recombinant techniques, or substantially free of chemical precursors or other chemicals when chemically synthesised. Suitably, an "isolated" polynucleotide is free of sequences (especially protein encoding sequences) that naturally flank the polynucleotide (i.e., sequences located at the 5' and 3' ends of the polynucleotide) in the genomic DNA of the organism from which the polynucleotide was derived. For example, in various embodiments, the isolated polynucleotide can contain less than about 5 kb, 4 kb, 3 kb, 2 kb, 1 kb, 0.5 kb, or 0.1 kb of nucleotide sequences that naturally flank the polynucleotide in genomic DNA of the cell from which the polynucleotide was derived. A polypeptide that is substantially free of cellular material includes preparations of protein having less than about 30%, 20%, 10%, 5%, (by dry weight) of contaminating protein. When the protein of the invention or biologically active portion thereof is recombinantly produced, culture medium suitably represents less than about 30%, 20%, 10%, or 5% (by dry weight) of chemical precursors or non-protein-of-interest chemicals.

The present invention also encompasses portions of the disclosed nucleotide sequences. Portions of a nucleotide sequence may encode polypeptide portions or segments that retain the biological activity of the native polypeptide and hence modulate or regulate disease resistance. Alternatively, portions of a nucleotide sequence that are useful as hybridisation probes generally do not encode amino acid sequences retaining such biological activity. Thus, portions of a nucleotide sequence may range from at least about 15, 16, 17, 18, 19, 20, 21, 22, 23, 24, 25, 26, 27, 28, 29, 30, 40, 50, 60, 80, 90, 100 nucleotides, or almost up to the full-length nucleotide sequence encoding the polypeptides of the invention.

A portion of an R nucleotide sequence that encodes a biologically active portion of an R polypeptide of the invention will encode at least about 5, 6, 7, 8, 9, 10, 11, 12, 13, 14, 15, 16, 17, 18, 19, 20, 21, 22, 23, 24, 25, 30, 40, 50, 60, 70, 80, 90, 100, 120, 150, 300, 400, 500, 600, 700, 800, 900 or 1000 contiguous amino acid residues, or almost up to the total number of amino acids present in a full-length R polypeptide of the invention (for example, 1440 or 1330 amino acid residues for SEQ ID NO: 2 or 4, respectively). Portions of an R nucleotide sequence that are useful as hybridisation probes or PCR primers generally need not encode a biologically active portion of an R polypeptide.

Thus, a portion of an R nucleotide sequence may encode a biologically active portion of an R polypeptide, or it may be a fragment that can be used as a hybridisation probe or PCR primer using standard methods known in the art. A biologically active portion of an R polypeptide can be prepared by isolating a portion of one of the R nucleotide sequences of the invention, expressing the encoded portion of the R polypeptide (e.g., by recombinant expression in vitro), and assessing the activity of the encoded portion of the R polypeptide. Nucleic acid molecules that are portions of an R nucleotide sequence comprise at least about 15, 16, 17, 18, 19, 20, 25, 30, 50, 75, 100, 150, 200, 250, 300, 350, 400, 450, 500, 550, 600, or 650 nucleotides, or almost up to the number of nucleotides present in a full-length R nucleotide sequence disclosed herein (for example, 4375 or 3690 nucleotides for SEQ ID NO: 1 or 14, respectively).

The invention also contemplates variants of the disclosed nucleotide sequences. Nucleic acid variants can be naturally occurring, such as allelic variants (same locus), homologues (different locus), and orthologues (different organism) or can be non naturally occurring. Naturally occurring variants such as these can be identified with the use of well-known molecular biology techniques, as, for example, with polymerase chain reaction (PCR) and hybridisation techniques as known in the art. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product). For nucleotide sequences, conservative variants include those sequences that, because of the degeneracy of the genetic code, encode the amino acid sequence of one of the R polypeptides of the invention. Variant nucleotide sequences also include synthetically derived nucleotide sequences, such as those generated, for example, by using site-directed mutagenesis but which still encode an R polypeptide of the invention. Generally, variants of a particular nucleotide sequence of the invention will have at least about 30%, 40% 50%, 55%, 60%, 65%, 70%, generally at least about 75%, 80%, 85%, desirably about 90% to 95% or more, and more suitably about 98% or more sequence identity to that particular nucleotide sequence as determined by sequence alignment programs described elsewhere herein using default parameters.

The nucleotide sequences of the invention can be used to isolate corresponding sequences from other organisms, particularly other plants. Methods are readily available in the art for the hybridisation of nucleic acid sequences. Coding sequences from other plants may be isolated according to well known techniques based on their sequence identity with the coding sequences set forth-herein. In these techniques all or part of the known coding sequence is used as a probe which selectively hybridises to other R coding sequences present in a population of cloned genomic DNA fragments or cDNA fragments (i.e., genomic or cDNA libraries) from a chosen organism. Accordingly, the present invention also contemplates polynucleotides that hybridise to the R gene nucleotide sequences, or to their complements, under stringency conditions described below. As used herein, the term "hybridises under low stringency, medium stringency, high stringency, or very high stringency conditions" describes conditions for hybridisation and washing. Guidance for performing hybridisation reactions can be found in Ausubel et al., (1998, supra), Sections 6.3.1-6.3.6. Aqueous and non-aqueous methods are described in that reference and either can be used. Reference herein to low stringency conditions include and encompass from at least about 1% v/v to at least about 15% v/v formamide and from at least about 1 M to at least about 2 M salt for hybridisation at 42° C., and at least about 1 M to at least about 2 M salt for washing at 42° C. Low stringency conditions also may include 1% Bovine Serum Albumin (BSA), 1 mM EDTA, 0.5 M NaHPO$_4$ (pH 7.2), 7% SDS for hybridisation at 65° C., and (i) 2×SSC, 0.1% SDS; or (ii) 0.5% BSA, 1 mM EDTA, 40 mM NaHPO$_4$ (pH 7.2), 5% SDS for washing at room temperature. One embodiment of low stringency conditions includes hybridisation in 6× sodium chloride/sodium citrate (SSC) at about 45° C., followed by two washes in 0.2×SSC, 0.1% SDS at least at 50° C. (the temperature of the washes can be increased to, 55° C. for low stringency conditions). Medium stringency conditions include and encompass from at least about 16% v/v to at least about 30% v/v formamide and from at least about 0.5 M to at least about 0.9 M salt for hybridisation at 42° C., and at least about 0.1 M to at least about 0.2 M salt for washing at 55° C. Medium stringency conditions also may include 1% Bovine Serum Albumin (BSA), 1 mM EDTA, 0.5 M NaHPO$_4$ (pH 7.2), 7% SDS for hybridisation at 65° C., and (i) 2×SSC, 0.1% SDS; or (ii) 0.5% BSA, 1 mM EDTA, 40 mM NaHO$_4$ (pH 7.2), 5% SDS for washing at 60-65° C. One embodiment of medium stringency conditions includes hybridising in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridisation at 42° C., and about 0.01 M to about 0.02 M salt for washing at 55° C. High stringency conditions also may include 1% BSA, 1 mM EDTA, 0.5 M NaHPO$_4$ (pH 7.2), 7% SDS for hybridisation at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridising in 6×SSC at about 45° C., followed by one or more washes in 0.2×SSC, 0.1% SDS at 65° C.

In certain embodiments, an isolated nucleic acid molecule of the invention hybridises under very high stringency conditions. One embodiment of very high stringency conditions includes hybridising 0.5M sodium phosphate, 7% SDS at 65° C., followed by one or more washes at 0.2×SSC, 1% SDS at 65° C.

Other stringency conditions are well known in the art and a skilled addressee will recognise that various factors can be manipulated to optimise the specificity of the hybridisation. Optimisation of the stringency of the final washes can serve to ensure a high degree of hybridisation. For detailed examples, see Ausubel et al., supra at pages 2.10.1 to 2.10.16 and Sambrook et al. (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridisation rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8). In general, the $T_m$ of a perfectly matched duplex of DNA may be predicted as an approximation by the formula:

$$T_m = 81.5 + 16.6 \,(\log_{10} M) + 0.41 \,(\% \, G+C) - 0.63 \,(\% \text{ formamide}) - (600/\text{length})$$

wherein: M is the concentration of Na$^+$, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m - 15°$ C. for high stringency, or $T_m - 30°$ C. for moderate stringency.

In one example of a hybridisation procedure, a membrane (e.g., a nitrocellulose membrane or a nylon membrane) containing immobilised DNA is hybridised overnight at 42° C. in a hybridisation buffer (50% deionised formamide, 5×SSC, 5× Denhardt's solution (0.1% ficoll, 0.1% polyvinylpyrollidone and 0.1% bovine serum albumin), 0.1% SDS and 200 mg/mL denatured salmon sperm DNA) containing labelled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2× SSC and 0.1% SDS solution for 12 min at 65-68° C.

Variant nucleotide sequences also encompass sequences derived from a mutagenic or recombinant procedures such as 'DNA shuffling' which can be used for swapping domains in a polypeptide of interest with domains of other polypeptides. With DNA shuffling, one or more different R coding sequences can be manipulated to create a new R sequence possessing desired properties. In this procedure, libraries of recombinant polynucleotides are generated from a population of related polynucleotides comprising sequence regions that have substantial sequence identity and can be homologously recombined in vitro or in vivo. For example, using this approach, sequence motifs encoding a domain of interest (e.g., the coiled coil domain, the NBS domain and/or the LRR domain of the polypeptides of the invention) may be shuffled between the R gene of the invention and other known R genes to obtain a new gene coding for a protein with an improved property of interest, such broadening spectrum of disease resistance. Illustrative resistance R genes that could be employed for this purpose are listed in Table B below.

TABLE B

PLANT DISEASE RESISTANCE GENES CLONED FROM 1994 TO 2003.

| PLANT-PATHOGEN INTERACTION | | PLANT (R) PROTEIN STRUCTURE | R PROTEIN NAME | REFERENCE |
| --- | --- | --- | --- | --- |
| Flax | *Melampsora lini* | TIR-NBS-LRR | L | Lawrence et al., 1995 |
| Tobacco | Tobacco mosaic virus | TIR-NBS-LRR | N | Whitman et al., 1996 |
| Flax | *Melampsora lini* | TIR-NBS-LRR | M | Anderson et al., 1997 |
| Arabidopsis | *Peronospora parasitica* | TIR-NBS-LRR | RPP 5 | Parker et al., 1997 |
| Arabidopsis | *Pseudomonas* | TIR-NBS-LRR | RPS4 | Gassmann et al., 1999 |
| Flax | *Melampsora lini* | TIR-NBS-LRR | P | Dodds et al., 2000 |
| Arbidopsis | *Pseudomonas syringae* | NBS-LRR | RPS2 | Mindrinos et al., 1994 |
| Tomato | *Pseudomonas syringae* | NBS-LRR | Prf | Salmeron et al., 1996 |
| Arbidopsis | *Pseudomonas syringae* | NBS-LRR | RPM1 | Grant et al., 1996 |
| Wheat | *Heterodera avenae* | NBS-LRR | Cre3 | Lagudah et al., 1997 |
| Tomato | *Fusarium oxysporum* | NBS-LRR | 12 | Simons et al., 1998 |
| Tomato | *Meloidogyne sp* | NBS-LRR | Mi | Milligan et al., 1998 |
| Tomato | *Macrosiphum euphorbie* | NBS-LRR | Mi | Milligan et al., 1998 |
| Arabidopsis | *Peronospora parasitica* | NBS-LRR | RPP1 | Botella et al., 1998 |
| Lettuce | *Bremia lactucae* | NBS-LRR | Dm3 | Meyers et al., 1998 |
| Rice | *Xanthomonas* | NBS-LRR | Xa1 | Yoshimura et al., 1998 |
| Arabidopsis | *Pseudomonas* | NBS-LRR | RPS5 | Warren et al., 1998 |
| Maize | *Puccinia sorghi* | NBS-LRR | Rp1-D | Collins et al, 1999 |
| Pepper | *Xanthomonas campestris* | NBS-LRR | Bs2 | Thai et al., 1999 |
| Potato | PVX | NBS-LRR | Rx2 | Bendahmane et al., 1999 |
| Rice | *Magnaporthe* | NBS-LRR | Pi-ta | Bryan et al., 2000 |
| Barley | *Blumeria graminis* | NBS-LRR | Mla | Zhou et al., 2000 |
| Arabidopsis | *Peronospora parasitica* | NBS-LRR | RPP 13 | Bittner-Eddy et al., 2000 |

TABLE B-continued

PLANT DISEASE RESISTANCE GENES CLONED FROM 1994 TO 2003.

| PLANT-PATHOGEN INTERACTION | | PLANT (R) PROTEIN STRUCTURE | R PROTEIN NAME | REFERENCE |
|---|---|---|---|---|
| Tomato | Tospovirus | NBS-LRR | Sw-5 | Brommonschenkel et al., 2000 |
| Potato | *Globodera pallida* | NBS-LRR | Gpa 2 | Van der Vossen et al, 2000 |
| Potato | *Phytophtora infestans* | NBS-LRR | R1 | Ballvora et al., 2002 |
| Tomato | *Globodera rostochiensis* | NBS-LRR | Hero | Ernst et al., 2002 |
| Potato | *Phytophthora infestans* | NBS-LRR | RB | Song et al., 2003 |

Strategies for DNA shuffling are known in the art. See, for example: Stemmer (1994, *Proc. Natl. Acad. Sci. USA* 91:10747-10751; 1994, *Nature* 370:389-391); Crameri et al. (1997, *Nature Biotech.* 15:436-438); Moore et al. (1997, *J. Mol. Biol.* 272:336-347); Zlang et al. (1997 *Proc. Natl. Acad. Sci. USA* 94:450-44509); Crameri et al. (1998, *Nature* 391: 288-291); and U.S. Pat. Nos. 5,605,793 and 5,837,458.

4. Polypeptides of the Invention

The present invention provides polypeptides and biologically active portions thereof that confer resistance to disease, especially resistance to pathogenic disease including disease caused by fungal pathogen, viruses, nematodes, insects and the like. Biologically active portions of the R polypeptides of the invention include portions with immuno-interactive activity of at least about 6, 8, 10, 12, 14, 16, 18, 20, 25, 30, 40, 50, 60 amino acid residues in length. For example, immuno-interactive fragments contemplated by the present invention are at least 6 and desirably at least 8 amino acid residues in length, which can elicit an immune response in an animal for the production of antigen-binding molecules that are immuno-interactive with the R polypeptides of the invention. Such antigen-binding molecules can be used to screen organisms, especially plants, for structurally and/or functionally related R polypeptides. Typically, portions of the disclosed R polypeptides may participate in an interaction, e.g., an intramolecular or an inter-molecular interaction. An inter-molecular interaction can be a specific binding interaction or an enzymatic interaction (e.g., the interaction can be transient and a covalent bond is formed or broken). An inter-molecular interaction can be between an R polypeptide and a pathogen elicitor protein. Biologically active portions of an R polypeptide include peptides comprising amino acid sequences sufficiently similar to or derived from the amino acid sequences of the disclosed R polypeptides, e.g., the amino acid sequences shown in SEQ ID NO: 2 or 4, which include less amino acids than the full-length R polypeptide, and exhibit at least one activity of an R polypeptide. Typically, biologically active portions comprise a domain or motif with at least one activity of the R polypeptide, e.g., the ability to bind to a pathogen elicitor protein or to confer disease resistance. A biologically active portion of an R polypeptide can be a polypeptide which is, for example, 5, 6, 7, 8, 9, 10, 11, 12, 13, 14, 15, 16, 17, 18, 19, 20, 21, 22, 23, 24, 25, 30, 40, 50, 60, 70, 80, 90, 100, 120, 150, 300, 400, 500, 600, 700, 800, 900 or 1000 or more amino acids in length. Suitably, the portion is a "biologically-active portion" having no less than about 1%, 10%, 25% 50% of the pathogen elicitor protein-binding activity or the resistance-conferring activity of the full-length polypeptide.

The present invention also contemplates variant R polypeptides. 'Variant' polypeptides include proteins derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, modulating disease resistance or interacting with a pathogen elicitor protein. Such variants may result from, for example, genetic polymorphism or from human manipulation. Biologically active variants of a native R protein of the invention will have at least 40%, 50%, 60%, 70%, generally at least 75%, 80%, 85%, preferably about 90% to 95% or more, and more preferably about 98% or more sequence similarity with the amino acid sequence for the native protein as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the R proteins can be prepared by mutations in the DNA. Methods for mutagenesis and nucleotide sequence alterations are well known in the art. See, for example, Kunkel (1985, *Proc. Natl. Acad. Sci. USA* 82:488-492), Kunkel et al. (1987, *Methods in Enzymol.* 154:367-382), U.S. Pat. No. 4,873,192, Watson, J. D. et al. ("Molecular Biology of the Gene", Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.). Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of R polypeptides. Recursive ensemble mutagenesis (REM), a new technique which enhances the frequency of functional mutants in the libraries, can be used in combination with the screening assays to identify R polypeptide variants (Arkin and Yourvan (1992) *Proc. Natl. Acad. Sci. USA* 89:7811-7815; Delgrave et al. (1993) *Protein Engineering* 6:327-331). Conservative substitutions, such as exchanging one amino acid with another having similar properties, may be desirable as discussed in more detail below.

Variant polypeptides may contain conservative amino acid substitutions at various locations along their sequence, as compared to the R polypeptide amino acid sequences of the invention. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterises certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the carbon. Several amino acid similarity matrices (e.g., PAM120 matrix and PAM250 matrix as disclosed for example by Dayhoff et al. (1978) A model of evolutionary change in proteins. Matrices for determining distance relationships In M. O. Dayhoff, (ed.), Atlas of protein sequence and structure, Vol. 5, pp. 345-358, National Biomedical Research Foundation, Washington D.C.; and by Gonnet et al., 1992, Science 256(5062): 144301445), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behaviour.

Amino acid residues can be further sub-classified as cyclic or noncyclic, and aromatic or nonaromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always nonaromatic. Dependent on their structural properties, amino acid residues may fall in two or more classes. For the naturally-occurring protein amino acids, sub-classification according to the this scheme is presented in the Table C.

TABLE C

AMINO ACID SUB-CLASSIFICATION

| SUB-CLASSES | AMINO ACID |
| --- | --- |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Accordingly, the present invention also contemplates variants of the naturally occurring or parent R polypeptide sequences or their biologically-active fragments, wherein the variants are distinguished from the parent sequences by the addition, deletion, or substitution of one or more amino acids. In general, variants display at least about 30, 40, 50, 55, 60, 65, 70, 75, 80, 85, 90, 91, 92, 93, 94, 95, 96, 97, 98, 99% similarity to a parent R polypeptide sequence as for example set forth in SEQ ID NO: 2 or 4. Desirably, variants will have at least 30, 40, 50, 55, 60, 65, 70, 75, 80, 85, 90, 91, 92, 93, 94, 95, 96, 97, 98, 99% sequence identity to a parent R polypeptide sequence as set forth in SEQ ID NO:2 or 4. Moreover, sequences differing from the native or parent sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100, 150, 200, 300, 500 or more amino acids but which retain the disease-resistance-conferring or pathogen elicitor-binding properties are contemplated. Polypeptides of the invention include polypeptides that are encoded by polynucleotides that hybridise under stringency conditions as defined herein, especially high stringency conditions, to the polynucleotide sequences of the invention, or the non-coding strand thereof, as described above.

In one embodiment, variant polypeptides differ from the disclosed sequences by at least one but by less than 50, 40, 30, 20, 15, 10, 8, 6, 5, 4, 3, 2 or 1 amino acid residue(s). In another, variant polypeptides differ from the corresponding sequence in SEQ ID NO: 2 or 4 by at least 1% but less than 20%, 15%, 10% or 5% of the residues. (If this comparison requires alignment the sequences should be aligned for maximum similarity. "Looped" out sequences from deletions or insertions, or mismatches, are considered differences.) The differences are, suitably, differences or changes at a non-essential residue or a conservative substitution.

A "non-essential" amino acid residue is a residue that can be altered from the wild-type sequence of an R polypeptide without abolishing or substantially altering one or more of its activities (e.g., disease-resistance or pathogen elicitor-binding properties). Suitably, the alteration does not substantially alter one of these activities, e.g., the activity is at least 20%, 40%, 60%, 70% or 80% of wild-type. An "essential" amino acid residue is a residue that, when altered from the wild-type sequence of an R polypeptide of the invention, results in abolition of disease-resistance or pathogen elicitor-binding properties such that less than 20% of the wild-type activity is present. For example, conserved amino acid residues between the R polypeptides shown in FIG. 2 may be unamenable to alteration.

Desirable variant R polypeptides are those having conserved amino acid substitutions. Examples of conservative substitutions include the following: aspartic-glutamic as acidic amino acids; lysine/arginine/histidine as basic amino acids; serine/glycine/alanine/threonine as small amino acids, leucine/isoleucine, methionine/valine, alanine/valine as hydrophobic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional R polypeptide can readily be determined by assaying its disease resistance-conferring activity or its pathogen-elicitor-binding activity. Conservative substitutions are shown in Table D below under the heading of exemplary substitutions. More preferred substitutions are shown under the heading of preferred substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE D

EXEMPLARY AND PREFERRED AMINO ACID SUBSTITUTIONS

| ORIGINAL RESIDUE | EXEMPLARY SUBSTITUTIONS | PREFERRED SUBSTITUTIONS |
|---|---|---|
| Ala | Val, Leu, Ile | Val |
| Arg | Lys, Gln, Asn | Lys |
| Asn | Gln, His, Lys, Arg | Gln |
| Asp | Glu | Glu |

TABLE D-continued

EXEMPLARY AND PREFERRED AMINO ACID SUBSTITUTIONS

| ORIGINAL RESIDUE | EXEMPLARY SUBSTITUTIONS | PREFERRED SUBSTITUTIONS |
|---|---|---|
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, Wm.C. Brown Publishers (1993).

Thus, a predicted non-essential amino acid residue in an R polypeptide is typically replaced with another amino acid residue from the same side chain family. Alternatively, mutations can be introduced randomly along all or part of an R gene coding sequence, such as by saturation mutagenesis, and the resultant mutants can be screened for disease resistance-conferring activity or pathogen-elicitor-binding activity to identify mutants that retain activity. Following mutagenesis of the coding sequences, the encoded peptide can be expressed recombinantly and the activity of the peptide can be determined.

In other embodiments, variant R polypeptides include an amino acid sequence having at least about 50%, 55%, 60%, 65%, 70%, 75%, 80%, 85%, 90%, 91%, 92%, 93%, 94% 95%, 96%, 97%, 98% or more similarity to a corresponding sequence of SEQ ID NO: 2 or 4, and has disease resistance-conferring activity or pathogen-elicitor-binding activity.

The R polypeptides of the present invention contain a significant number of structural characteristics in common with each other as for example depicted in FIG. 2. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally-occurring and can be from either the same or different species. Members of a family can also have common functional characteristics.

5. Anti-R Polypeptide Antigen-Binding Molecules

The invention also provides an antigen-binding molecule that is specifically immuno-interactive with an R polypeptide of the invention. In one embodiment, the antigen-binding molecule comprise whole polyclonal antibodies. Such antibodies may be prepared, for example, by injecting a polypeptide, portion or variant of the invention into a production species, which may include mice or rabbits, to obtain polyclonal antisera. Methods of producing polyclonal antibodies are well known to those skilled in the art. Exemplary protocols which may be used are described for example in Coligan et al., CURRENT PROTOCOLS IN IMMUNOLOGY, (John Wiley & Sons, Inc, 1991), and Ausubel et al., (1994-1998, supra), in particular Section III of Chapter 11.

In lieu of polyclonal antisera obtained in a production species, monoclonal antibodies may be produced using the standard method as described, for example, by Köhler and Milstein (1975, *Nature* 256, 495-497), or by more recent modifications thereof as described, for example, in Coligan et al., (1991, supra) by immortalising spleen or other antibody producing cells derived from a production species which has been inoculated with one or more of the polypeptides, fragments, variants or derivatives of the invention.

The invention also contemplates as antigen-binding molecules Fv, Fab, Fab' and F(ab')$_2$ immunoglobulin fragments. Alternatively, the antigen-binding molecule may comprise a synthetic stabilised Fv fragment. Exemplary fragments of this type include single chain Fv fragments (sFv, frequently termed scFv) in which a peptide linker is used to bridge the N terminus or C terminus of a $V_H$ domain with the C terminus or N-terminus, respectively, of a $V_L$ domain. ScFv lack all constant parts of whole antibodies and are not able to activate complement. ScFvs may be prepared, for example, in accordance with methods outlined in Kreber et al. (Kreber et al. 1997, *J. Immunol. Methods;* 201(1): 35-55). Alternatively, they may be prepared by methods described in U.S. Pat. No. 5,091,513, European Patent No 239,400 or the articles by Winter and Milstein (1991, *Nature* 349:293) and Plückthun et al. (1996, In *Antibody engineering: A practical approach.* 203-252). In another embodiment, the synthetic stabilised Fv fragment comprises a disulphide stabilised Fv (dsFv) in which cysteine residues are introduced into the $V_H$ and $V_L$ domains such that in the fully folded Fv molecule the two residues will form a disulphide bond therebetween. Suitable methods of producing dsFv are described for example in (Glockscuther et al. *Biochem.* 29: 1363-1367; Reiter et al. 1994, *J. Biol. Chem.* 269: 18327-18331; Reiter et al. 1994, *Biochem.* 33: 5451-5459; Reiter et al. 1994. *Cancer Res.* 54: 2714-2718; Webber et al. 1995, *Mol. Immunol.* 32: 249-258).

Phage display and combinatorial methods for generating R polypeptide antigen-binding molecules are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J.* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 2:1373-1377; Hoogenboom et al. (1991) *Nuc Acid Res* 19:4133-4137; and Barbas et al. (1991) *PNAS* 88:7978-7982). The antigen-binding molecules can be used to screen expression libraries for variant R polypeptides. They can also be used to detect and/or isolate the R polypeptides of the invention. Thus, the invention also contemplates the use of antigen-binding molecules to isolate R polypeptides using, for example, any suitable immunoaffinity based method including, but not limited to, immunochromatography and immunoprecipitation. A suitable method utilises solid phase adsorption in which anti-R polypeptide antigen-binding molecules are attached to a suitable resin, the resin is contacted with a sample suspected of containing a R polypeptide, and the R polypeptide, if any, is subsequently eluted from the resin. Illustrative resins include: Sepharose® (Pharmacia), Poros® resins (Roche Molecular Biochemicals, Indianapolis), Actigel Superflow™ resins (Sterogene Bio-separations Inc., Carlsbad Calif.), and Dynabeads™ (Dynal Inc., Lake Success, N.Y.).

The antigen-binding molecule can be coupled to a compound, e.g., a label such as a radioactive nucleus, or imaging agent, e.g., a radioactive, enzymatic, or other, e.g., imaging agent, e.g., a NMR contrast agent. Labels which produce detectable radioactive emissions or fluorescence are preferred. An anti-R polypeptide antigen-binding molecule (e.g., monoclonal antibody) can be used to detect R polypeptides (e.g., in a cellular lysate or cell supernatant) in order to evaluate the abundance and pattern of expression of the protein. Anti-R polypeptides antigen-binding molecules can be used diagnostically to monitor R polypeptides levels in tissue as part of an agronomic testing procedure. Detection can be facilitated by coupling (i.e., physically lining) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and acquorin, and examples of suitable radioactive material include $^{125}I$, $^{131}I$, $^{35}S$ or $^3H$. The label may be selected from a group including a chromogen, a catalyst, an enzyme, a fluorophore, a chemiluminescent molecule, a lanthanide ion such as Europium ($Eu^{34}$), a radioisotope and a direct visual label. In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes useful as labels is disclosed in United States Patent Specifications U.S. Pat. Nos. 4,366,241, 4,843,000, and 4,849,338. Enzyme labels useful in the present invention include alkaline phosphatase, horseradish peroxidase, luciferase, β-galactosidase, glucose oxidase, lysozyme, malate dehydrogenase and the like. The enzyme label may be used alone or in combination with a second enzyme in solution.

6. Nucleic Acid Constructs 6.1 Prokaryotic Expression

The present invention further relates to a nucleic acid construct designed for genetic transformation of prokaryotic cells, comprising a polynucleotide, portion or variant according to the invention operably linked to a regulatory sequence, which will typically comprise a transcriptional control element or promoter. Suitably, the chimeric construct is operable in a Gram-negative prokaryotic cell. A variety of prokaryotic expression vectors, which may be used as a basis for constructing the chimeric nucleic acid construct, may be utilised to express a polynucleotide, portion or variant according to the invention. These include but are not limited to a chromosomal vector (e.g., a bacteriophage such as bacteriophage λ), an extrachromosomal vector (e.g., a plasmid or a cosmid expression vector). The expression vector will also typically contain an origin of replication, which allows autonomous replication of the vector, and one or more genes that allow phenotypic selection of the transformed cells. Any of a number of suitable promoter sequences, including constitutive and inducible promoter sequences, may be used in the expression vector (see e.g., Bitter, et al., 1987, *Methods in Enzymology* 153: 516-544). For example, inducible promoters such as pL of bacteriophage γ, plac, ptrp, ptac ptrp-lac hybrid promoter and the like may be used. The nucleic acid construct may then be used to transform the desired prokaryotic host cell to produce a recombinant prokaryotic host cell, e.g., for producing a recombinant R polypeptide.

6.2 Eukaryotic Expression

The invention also contemplates a nucleic acid construct designed for expressing a polynucleotide, portion or variant of the invention in a eukaryotic host cell. A variety of eukaryotic host-expression vector systems may be utilised in this regard. These include, but are not limited to, yeast transformed with recombinant yeast expression vectors; insect cell systems infected with recombinant virus expression vectors (e.g., baculovirus); or animal cell systems infected with recombinant virus expression vectors (e.g., retroviruses, adenovirus, Vaccinia virus), or transformed animal cell systems engineered for stable expression. In certain advantageous embodiments, the chimeric nucleic acid construct is designed for genetic transformation of plants as described hereinafter.

6.3 Plant Expression

In accordance with the present invention, it is proposed that the R gene polynucleotides, portions and variants of the invention will be useful for facilitating the construction of crop plants that are resistant to pathogenic disease, including diseases caused by fungal pathogens, viruses, nematodes, insects and the like. Accordingly, the present invention also relates to operably linking a polynucleotide, portion or variant of as described herein to a regulatory sequence (e.g., a promoter and a 3' non-translated region) that is function in plants to create a nucleic acid construct, designed for genetic transformation of plants.

6.3.1 Plant Promoters

Numerous promoters that are active in plant cells have been described in the literature, illustrative examples of which include the nopaline synthase (NOS) promoter, the octopine synthase (OCS) promoter (which is carried on tumour-inducing plasmids of *Agrobacterium tumefaciens*), the caulimovirus promoters such as the cauliflower mosaic virus (CaMV) 19S promoter and the CaMV 35S promoter, the figwort mosaic virus 35S-promoter, the light-inducible promoter from the small subunit of ribulose-1,5-bis-phosphate carboxylase (ssRUBISCO), the Adh promoter, the sucrose synthase promoter, the R gene complex promoter, the GST-II-27 gene promoter and the chlorophyll a/b binding protein gene promoter, etc.

For the purpose of expression in source tissues of the plant, such as the leaf, seed, root or stem, it is desirable that the promoters driving expression of the target gene have relatively high expression in these specific tissues. For this purpose, one may choose from a number of promoters for genes with tissue- or cell-specific or enhanced expression. Examples of such promoters reported in the literature include the chloroplast glutamine synthetase GS2 promoter from pea, the chloroplast fructose-1,6-biphosphatase (FBPase) promoter from wheat, the nuclear photosynthetic ST-LS1 promoter from potato, the serine/threonine kinase (PAL) promoter and the glucoamylase (CHS) promoter from *Arabidopsis thaliana*. Also reported to be active in photosynthetically active tissues are the ribulose-1,5-bisphosphate carboxylase (RbcS) promoter from eastern larch (*Larix laricina*), the promoter for the cab gene, cab6, from pine, the promoter for the Cab-1 gene from wheat, the promoter for the CAB-1 gene from spinach, the promoter for the cab1R gene from rice, the pyruvate, orthophosphate dikinase (PPDK) promoter from corn, the promoter for the tobacco Lhcb1*2 gene, the *Arabidopsis thaliana* SUC2 sucrose-H+ symporter and the promoter for the thylakoid membrane proteins from spinach (psaD, psaF, psaE, PC, FNR, atpC, atpD, cab, rbcS). Other promoters for the chlorophyll a/b-binding proteins may also be utilised in the invention, such as the promoters for LhcB gene and PsbP gene from white mustard.

For the purpose of expression in sink tissues of the plant, such as the tuber of the potato plant, the fruit of tomato, or the seed of corn, wheat, rice and barley, it is desirable that the promoters driving expression of the target gene have relatively high expression in these specific tissues. A number of promoters for genes with tuber-specific or tuber-enhanced expression are known, including the class I patatin promoter, the promoter for the potato tuber ADPGPP genes, both the large and small subunits, the sucrose synthase promoter, the promoter for the major tuber proteins including the 22 kd protein complexes and protease inhibitors, the promoter for the granule-bound starch synthase gene (GBSS) and other class I and II patatins promoters.

Other promoters can also be used to express a target gene in specific tissues, such as seeds or fruits. Examples of such promoters include the 5' regulatory regions from such genes as napin, phaseolin, soybean trypsin inhibitor, ACP, stearoyl-ACP desaturase, soybean α' subunit of β-conglycinin (soy 7s), and oleosin. Further examples include the promoter for β-conglycinin. Also included are the zeins, which are a group of storage proteins found in corn endosperm. Genomic clones for zein genes have been isolated and the promoters from these clones, including the 15 kD, 16 kD, 19 kD, 22 kD, 27 kD and genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. Examples of promoters suitable for expression in wheat include those promoters for the ADPglucose pyrosynthase (ADPGPP) subunits, the granule bound and other starch synthase, the branching and debranching enzymes, the embryogenesis-abundant proteins, the gliadins and the glutenins. Examples of such promoters in rice include those promoters for the ADPGPP subunits, the granule bound and other starch synthase, the branching enzymes, the debranching enzymes, sucrose synthases and the glutelins. Examples of such promoters for barley include those for the ADPGPP subunits, the granule bound and other starch synthase, the branching enzymes, the debranching enzymes, sucrose synthases, the hordeins, the embryo globulins and the aleurone specific proteins.

Root specific promoters may also be used. An example of such a promoter is the promoter for the acid chitinase gene. Expression in root tissue could also be accomplished using the root specific subdomains of the CaMV35S promoter that have been identified.

Desirable promoters for expression in cultured cells are strong constitutive promoters, or promoters that respond to a specific inducer (Gatz and Lenk, 1998, *Trends Plant Science*

3: 352-8). In certain embodiments, nucleic acid constructs expressing R polynucleotides of the present invention are introduced into banana plants that are susceptible Exemplary constitutive promoters for expression in intact banana plants are described in International Publication No. WO 02/053744 and in co-pending PCT Application No. PCT/AU03/00919.

6.3.2 3' Non-Translated Region

The constructs of the present invention can comprise a 3' non-translated sequence. A 3' non-translated sequence refers to that portion of a gene comprising a DNA segment that contains a polyadenylation signal and any other regulatory signals capable of effecting mRNA processing or gene expression. The polyadenylation signal is characterised by effecting the addition of polyadenylic acid tracts to the 3' end of the mRNA precursor. Polyadenylation signals are commonly recognised by identity with the canonical form 5' AATAAA-3' although variations are not uncommon.

The 3' non-translated regulatory DNA sequence preferably includes from about 50 to 1,000 nucleotide base pairs and may contain plant transcriptional and translational termination sequences in addition to a polyadenylation signal and any other regulatory signals capable of effecting mRNA processing or gene expression. Examples of suitable 3' non-translated sequences are the 3' transcribed non-translated regions containing a polyadenylation signal from the nopaline synthase (nos) gene of *Agrobacterium tumefaciens* (Bevan et al., 1983, *Nucl. Acid Res.*, 11:369) and the terminator for the T7 transcript from the octopine synthase gene of *Agrobacterium tumefaciens*. Alternatively, suitable 3' non-translated sequences may be derived from plant genes such as the 3' end of the protease inhibitor I or II genes from potato or tomato, the soybean storage protein genes and the pea E9 small subunit of the ribulose-1,5-bisphosphate carboxylase (ss-RUBISCO) gene, although other 3' elements known to those of skill in the art can also be employed. Alternatively, 3' non-translated regulatory sequences can be obtained de novo as, for example, described by An (1987, *Methods in Enzymology*, 153:292).

6.3.3 Optional Sequences

The nucleic acid construct of the present invention can further include enhancers, either translation or transcription enhancers, as may be required. These enhancer regions are well known to persons skilled in the art, and can include the ATG initiation codon and adjacent sequences. The initiation codon must be in phase with the reading frame of the coding sequence relating to the foreign or endogenous DNA sequence to ensure translation of the entire sequence. The translation control signals and initiation codons can be of a variety of origins, both natural and synthetic. Translational initiation regions may be provided from the source of the transcriptional initiation region, or from the foreign or endogenous DNA sequence. The sequence can also be derived from the source of the promoter selected to drive transcription, and can be specifically modified so as to increase translation of the mRNA.

Examples of transcriptional enhancers include, but are not restricted to, elements from the CaMV 35S promoter and octopine synthase genes as for example described by Last et al. (U.S. Pat. No. 5,290,924). It is proposed that the use of an enhancer element such as the ocs element, and particularly multiple copies of the element, will act to increase the level of transcription from adjacent promoters when applied in the context of plant transformation. Alternatively, the omega sequence derived from the coat protein gene of the tobacco mosaic virus (Gallie et al., 1987, *Nucleic Acids Res.* 15(8): 3257-73) may be used to enhance translation of the mRNA transcribed from a polynucleotide according to the invention.

As the DNA sequence inserted between the transcription initiation site and the start of the coding sequence, i.e., the untranslated leader sequence, can influence gene expression, one can also employ a particular leader sequence. Preferred leader sequences include those that comprise sequences selected to direct optimum expression of the R polypeptide gene. For example, such leader sequences include a preferred consensus sequence which can increase or maintain mRNA stability and prevent inappropriate initiation of translation as for example described by Joshi (1987, *Nucl. Acid Res.*, 15:6643). However, other leader sequences, e.g., the leader sequence of RTBV, have a high degree of 5 secondary structure that is expected to decrease mRNA stability and/or decrease translation of the mRNA. Thus, leader sequences (i) that do not have a high degree of secondary structure, (ii) that have a high degree of secondary structure where the secondary structure does not inhibit mRNA stability and/or decrease translation, or (iii) that are derived from genes that are highly expressed in plants, will be most preferred.

Regulatory elements such as the sucrose synthase intron as, for example, described by Vasil et al. (1989, *Plant Physiol.*, 91:5175), the Adh intron I as, for example, described by Callis et al. (1987, *Genes Develop.*, II), or the TMV omega element as, for example, described by Gallie et al. (1989, *The Plant Cell*, 1:301) can also be included where desired. Other such regulatory elements useful in the practice of the invention are known to those of skill in the art.

Additionally, targeting sequences may be employed to target R polypeptide to an intracellular compartment within plant cells or to the extracellular environment. For example, a DNA sequence encoding a transit or signal peptide sequence may be operably linked to a sequence encoding the R polypeptide or biologically active portion thereof such that, when translated, the transit or signal peptide can transport the polypeptide or portion to a particular intracellular or extracellular destination, and can then be post-translationally removed. Transit or signal peptides act by facilitating the transport of proteins through intracellular membranes, e.g., endoplasmic reticulum, vacuole, vesicle, plastid, mitochondrial and plasmalemma membranes. For example, the targeting sequence can direct a desired protein to a particular organelle such as a vacuole or a plastid (e.g., a chloroplast), rather than to the cytosol. Thus, the nucleic acid construct can further comprise a plastid transit peptide encoding DNA sequence operably linked between a promoter region or promoter variant according to the invention and the foreign or endogenous DNA sequence. For example, reference may be made to Heijne et al. (1989, *Eur. J. Biochem.*, 180:535) and Keegstra et al. (1989, *Ann. Rev. Plant Physiol. Plant Mol. Biol.*, 40:471).

The nucleic acid construct is typically introduced into a vector, such as a plasmid. Plasmid vectors include additional DNA sequences that provide for easy selection, amplification, and transformation of the expression cassette in prokaryotic and eukaryotic cells, e.g., pUC-derived vectors, pSK-derived vectors, pGEM-derived vectors, pSP-derived vectors, or pBS-derived vectors. Additional DNA sequences include origins of replication to provide for autonomous replication of the vector, selectable marker genes, preferably encoding antibiotic or herbicide resistance, unique multiple cloning sites providing for multiple sites to insert DNA sequences or genes encoded in the nucleic acid construct, and sequences that enhance transformation of prokaryotic and eukaryotic cells.

The vector desirably contains an element(s) that permits either stable integration of the vector into the host cell genome or autonomous replication of the vector in the cell independent of the genome of the cell. The vector may be integrated into the host cell genome when introduced into a host cell. For integration, the vector may rely on a foreign or endogenous DNA sequence present therein or any other element of the vector for stable integration of the vector into the genome by homologous recombination. Alternatively, the vector may contain additional nucleic acid sequences for directing integration by homologous recombination into the genome of the host cell. The additional nucleic acid sequences enable the vector to be integrated into the host cell genome at a precise location in the chromosome. To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences.

For cloning and subcloning purposes, the vector may further comprise an origin of replication enabling the vector to replicate autonomously in a host cell such as a bacterial cell. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. The origin of replication may be one having a mutation to make its function temperature-sensitive in a *Bacillus* cell (see, e.g., Ehrlich, 1978, *Proc. Natl. Acad. Sci. USA* 75:1433).

6.3.4 Marker Genes

To facilitate identification of transformants, the nucleic acid construct desirably comprises a selectable or screenable marker gene as, or in addition to, a polynucleotide sequence according to the invention. The actual choice of a marker is not crucial as long as it is functional (i.e., selective) in combination with the plant cells of choice. The marker gene and the R polynucleotide sequence of interest do not have to be linked, since co-transformation of unlinked genes as, for example, described in U.S. Pat. No. 4,399,216 is also an efficient process in plant transformation.

Included within the terms selectable or screenable marker genes are genes that encode a "secretable marker" whose secretion can be detected as a means of identifying or selecting for transformed cells. Examples include markers that encode a secretable antigen that can be identified by antibody interaction, or secretable enzymes that can be detected by their catalytic activity. Secretable proteins include, but are not restricted to, proteins that are inserted or trapped in the cell wall (e.g., proteins that include a leader sequence such as that found in the expression unit of extensin or tobacco PR-S); small, diffusible proteins detectable, e.g., by ELISA; and small active enzymes detectable in extracellular solution (e.g., α-amylase, β-lactamase, phosphinothricin acetyltransferase).

6.3.5 Selectable Markers

Examples of bacterial selectable markers are the dal genes from *Bacillus subtilis* or *Bacillus licheniformis*, or markers that confer antibiotic resistance such as ampicillin, kanamycin, erythromycin, chloramphenicol or tetracycline resistance. Exemplary selectable markers for selection of plant transformants include, but are not limited to, a hygiene which encodes hygromycin B resistance; a neomycin phosphotransferase (neo) gene conferring resistance to kanamycin, paromomycin, G418 and the like as, for example, described by Potrykus et al. (1985, *Mol. Gen. Genet.* 199:183); a glutathione-5-transferase gene from rat liver conferring resistance to glutathione derived herbicides as, for example, described in EP-A 256 223; a glutamine synthetase gene conferring, upon overexpression, resistance to glutamine synthetase inhibitors such as phosphinothricin as, for example, described WO87/05327, an acetyl transferase gene from *Streptomyces viridochromogenes* conferring resistance to the selective agent phosphinothricin as, for example, described in EP-A 275 957, a gene encoding a 5-enolshikimate-3-phosphate synthase (EPSPS) conferring tolerance to N-phosphonomethylglycine as, for example, described by Hinchee et al. (1988, *Biotech.*, 6:915), a bar gene conferring resistance against bialaphos as, for example, described in WO91/02071; a nitrilase gene such as bxn from *Klebsiella ozaenae* which confers resistance to bromoxynil (Stalker et al., 1988, *Science,* 242:419); a dihydrofolate reductase (DHFR) gene conferring resistance to methotrexate (Thillet et al., 1988, *J. Biol. Chem.*, 263:12500); a mutant acetolactate synthase gene (ALS), which confers resistance to imidazolinone, sulfonylurea or other ALS-inhibiting chemicals (EP-A-154 204); a mutated anthralate synthase gene that confers resistance to 5-methyl tryptophan; or a dalapon dehalogenase gene that confers resistance to the herbicide.

6.3.6 Screenable Markers

Preferred screenable markers include, but are not limited to, a uidA gene encoding a β-glucuronidase (GUS) enzyme for which various chromogenic substrates are known; a β-galactosidase gene encoding an enzyme for which chromogenic substrates are known; an aequorin gene (Prasher et al., 1985, *Biochem. Biophys. Res. Comm.*, 126:1259), which may be employed in calcium-sensitive bioluminescence detection; a green fluorescent protein gene (Niedz et al., 1995 *Plant Cell Reports,* 14:403); a luciferase (luc) gene (Ow et al., 1986, *Science,* 234:856), which allows for bioluminescence detection; a β-lactamase gene (Sutcliffe, 1978, *Proc. Natl. Acad. Sci. USA* 75:3737), which encodes an enzyme for which various chromogenic substrates are known (e.g., PADAC, a chromogenic cephalosporin); an R-locus gene, encoding a product that regulates the production of anthocyanin pigments (red colour) in plant tissues (Delaporta et al., 1988, in *Chromosome Structure and Function*, pp. 263-282); an α-amylase gene (Ikuta et al., 1990, *Biotech.*, 8:241); a tyrosinase gene (Katz et al., 1983, *J. Gen. Microbiol.*, 129:2703) which encodes an enzyme capable of oxidising tyrosine to dopa and dopaquinone which in turn condenses to form the easily detectable compound melanin; or a xylE gene (Zukowsky et al., 1983, *Proc. Natl. Acad. Sci. USA* 80:1101), which encodes a catechol dioxygenase that can convert chromogenic catechols.

7. Introduction of the Nucleic Acid Construct into Plant Cells

The sequences of the present invention can be used to transform or transfect any plant. In this manner, genetically modified plants, plant cells, plant tissue, seed, and the like can be obtained. Transformation protocols as well as protocols for introducing nucleotide sequences into plants may vary depending on the type of plant or plant cell, i.e. monocot or dicot, targeted for transformation. It is recognised that the transformation protocols may be used for transfection or introduction of the oligonucleotide sequences to disrupt R gene function. Suitable methods of introducing nucleotide sequences into plant cells and subsequent insertion into the plant genome include microinjection (Crossway et al., 1986, *Biotechniques* 4:320-334), electroporation (Riggs et al., 1986, *Proc. Natl. Acad. Sci. USA* 83:5602-5606), *Agrobacterium*-mediated transformation (Townsend et al., U.S. Pat.

No. 5,563,055; Zhao et al., U.S. Pat. No. 5,981,840), direct gene transfer (Paszkowski et al., 1984, *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); and McCabe et al., (1988, *Biotechnology* 6:923-926). Also see Weissinger et al. (1988 *Ann. Rev. Genet.* 22:421-477), Sanford et al., (1987, *Particulate Science and Technology* 5:27-37; onion), Christou et al., (1988, *Plant Physiol.* 87:671-674; soybean); Datta et al., (1990, *Biotechnology* 8:736-740; rice), Klein et al. (1988, *Proc. Natl. Acad. Sci. USA* 85:4305-4309, maize), Hooykaas-Van Slogteren et al. (1984, *Nature* (London) 311:763-764; cereals), Bowen et al., (U.S. Pat. No. 5,736,369; cereals), Bytebier et al., (1987, *Proc. Natl. Acad. Sci. USA* 84:5345-5349; Liliaceae), De Wet et al. (1985, in The Experimental Manipulation of Ovule Tissues, ed. Chapman et al. (Longman, N.Y.), pp. 197-209; pollen), Kaeppler et al., (1990, *Plant Cell Reports* 9:415-418; 1992, *Theor. Appl. Genet.* 84:560-566; whisker-mediated transformation), D'Halluin et al. (1992, *Plant Cell* 4:1495-1505; electroporation); Li et al., (1993, *Plant Cell Reports* 12:250-255; rice), Christou ad Ford (1995, *Annals of Botany* 75:407-413; rice) and Osjoda et al. (1996, *Nature Biotechnology* 14:745-750; maize via *Agrobacterium tumefaciens*). Guidance in the practical implementation of transformation systems for plant improvement is provided by Birch (1997, *Annu. Rev. Plant Physiol. Plant Molec. Biol.* 48: 297-326).

In certain embodiments, the present invention is concerned with transforming monocotyledonous plants, including graminaceous and non-graminaceous monocotyledonous plants. Illustrative examples of non-graminaceous monocotyledonous plants include, but are not limited to, *Musaceae* (*Musa* and *Ensete*), taro, ginger, onions, garlic, pineapple, bromeliaeds, palms, orchids, lilies, irises and the like. There are a variety of methods known currently for transformation of monocotyledonous plants. Presently, preferred methods for transformation of monocots are microprojectile bombardment of explants or suspension cells, and direct DNA uptake or electroporation as, for example, described by Shimamoto et al. (1989, supra). Transgenic maize plants have been obtained by introducing the *Streptomyces hygroscopicus* bar gene into embryogenic cells of a maize suspension culture by microprojectile bombardment (Gordon-Kamm, 1990, *Plant Cell*, 2:603-618). The introduction of genetic material into aleurone protoplasts of other monocotyledonous crops such as wheat and barley has been reported (Lee, 1989, *Plant Mol. Biol.* 13:21-30). Wheat plants have been regenerated from embryogenic suspension culture by selecting only the aged compact and nodular embryogenic callus tissues for the establishment of the embryogenic suspension cultures (Vasil, 1990, *Bio/Technol.* 8:429-434). The combination with transformation systems for these crops enables the application of the present invention to monocots. These methods may also be applied for the transformation and regeneration of dicots. Transgenic sugarcane plants have been regenerated from embryogenic callus as, for example, described by Bower et al. (1996, *Molecular Breeding* 2:239-249).

8. Production and Characterisation of Differentiated Transgenic Plants 8.1 Regeneration The methods used to regenerate transformed cells into differentiated plants are not critical to this invention, and any method suitable for a target plant can be employed. Normally, a plant cell is regenerated to obtain a whole plant following a transformation process.

Regeneration from protoplasts varies from species to species of plants, but generally a suspension of protoplasts is made first. In certain species, embryo formation can then be induced from the protoplast suspension, to the stage of ripening and germination as natural embryos. The culture media will generally contain various amino acids and hormones, necessary for growth and regeneration. Examples of hormones utilised include auxins and cytokinins. It is sometimes advantageous to add glutamic acid and proline to the medium, especially for such species as corn and alfalfa. Efficient regeneration will depend on the medium, on the genotype, and on the history of the culture. If these variables are controlled, regeneration is reproducible. Regeneration also occurs from plant callus, explants, organs or parts. Transformation can be performed in the context of organ or plant part regeneration as, for example, described in *Methods in Enzymology*, Vol. 118 and Klee et al. (1987, *Annual Review of Plant Physiology*, 38:467), which are incorporated herein by reference. Utilising the leaf disk-transformation-regeneration method of Horsch et al. (1985, *Science*, 227:1229, incorporated herein by reference), disks are cultured on selective media, followed by shoot formation in about 24 weeks. Shoots that develop are excised from calli and transplanted to appropriate root-inducing selective medium Rooted plantlets are transplanted to soil as soon as possible after roots appear. The plantlets can be repotted as required, until reaching maturity.

In vegetatively propagated crops, the mature transgenic plants are propagated by the talking of cuttings or by tissue culture techniques to produce multiple identical plants. Selection of desirable transgenotes is made and new varieties are obtained and propagated vegetatively for commercial use.

In seed propagated crops, the mature transgenic plants can be self-crossed to produce a homozygous inbred plant. The inbred plant produces seed containing the newly introduced foreign gene(s). These seeds can be grown to produce plants that would produce the selected phenotype, e.g., early flowering.

Parts obtained from the regenerated plant, such as flowers, seeds, leaves, branches, fruit, and the like are included in the invention, provided that these parts comprise cells that have been transformed as described. Progeny and variants, and mutants of the regenerated plants are also included within the scope of the invention, provided that these parts comprise the introduced nucleic acid sequences.

The literature describes numerous techniques for regenerating specific plant types and more are continually becoming known. Those of ordinary skill in the art can refer to the literature for details and select suitable techniques without undue experimentation.

8.2 Characterisation

To confirm the presence of a R polynucleotide of the invention in the regenerating plants, a variety of assays may be performed. Such assays include, for example, "molecular biological" assays well known to those of skill in the art, such as Southern and Northern blotting and PCR; an R protein expressed by the polynucleotide of the invention may be assayed using antigen-binding molecules as for example described herein.

In order that the invention may be readily understood and put into practical effect, particular preferred embodiments will now be described by way of the following non-limiting example.

EXAMPLES

Example 1

Identification of R Genes from *M. acuminata*

CTAB total DNA Purification

Genomic DNA was extracted using the CTAB protocol of Stewart & Via (1993). Briefly, leaf tissue was frozen in liquid $N_2$ and ground in a mortar and pestle. Powdered tissue was resuspended in CTAB Buffer (1% Sarcosine, 0.8 M NaCl, 0.022 M EDTA pH8.0, 0.22 M Tris-HCl pH 7.8, 0.8% CTAB, 0.14 M Mannitol) at 65° C. An equal volume of chloroform:isoamylalcohol (24:1) was immediately added, mixed by inversion and incubated at 65° C. for 10 min with occasional inversion. Samples were centrifuged for 5 min at 14000 rpm in a microfuge to separate phases. The aqueous layer was collected and an equal volume of isopropanol added. DNA was spooled out, washed in 70% ethanol, and allowed to dry before resuspending in 100 μL $dH_2O$ containing RNaseA (1 mg/mL).

Purification of Total RNA

Total RNA extractions were performed using the method of Chang et al. (1993). Tissue was frozen in liquid $N_2$ and ground to a powder in a mortar and pestle. Powdered tissue was added to preheated (65° C.) extraction buffer (2% CTAB, 2% PVP, 100 mM Tris HCl pH8, 25 mM EDTA, 2 M NaCl, 0.05% spermidine, 2% beta-mercaptoethanol). Chloroform:isoamylalcohol (24:1) was added, the suspension vortexed, and samples centrifuged at top speed in a microfuge for 5 min. The aqueous phase was collected and an equal volume of DEPC-treated 4M LiCl added. RNA was precipitated overnight 4° C. and then centrifuged at 4° C. for 30 min at top speed. Pelleted RNA was resuspended in 10×SSTE and extracted once more with chloroform:isoamylalcohol (24:1). The RNA was reprecipitated at −20° C. overnight following the addition of 1/10 volume DEPC-treated 2.5 M NaOAc pH6.0 and 2 1/2 volumes of 100% ethanol. Tubes were centrifuged 20 min, the pellets washed with 70% ethanol and resuspended in DEPC-treated $dH_2O$.

Reverse-Transcriptase PCR of Banana R-Genes

Sequences of R-genes from plant species were aligned and degenerate primers designed to conserved motifs in the NBS regions. The degenerate primers were used to generate single-stranded cDNAs from total RNA using reverse transcriptase and then to subsequently amplify the NBS region of the banana R-genes. To generate the region 5' of the NBS domain, RNA primers were ligated to the 5' end of the mRNA after removal of the 5'-cap structure. Ligated mRNA was reverse transcribed using reverse transcriptase to generate single-stranded cDNA. Primer complementary to the ligated RNA primer and a specific primer to the known NBS sequence was added and PCR undertaken to generate the 5' region of the R-gene using the parameters of: initial denaturation step of 94° C. for 2 min followed by 5 cycles of 94° C. for 30 sees, 55-65° C. for 30 secs, 72° C. for 3-5 min, then 25 cycles of 94° C. for 30 secs, 45-60° C. for 30 secs, 72° C. for 3-5 min, followed by a final annealing step 72° C. for 10 min. N-terminal and C-terminal primers were subsequently used to amplify complete R-gene sequences from genomic DNA using PCR with the following conditions: initial denaturation step of 94° C. for 2 min, followed by 25 cycles of 94° C. for 30 secs, 55° C. for 30 secs, 72° C. for 1-5 min, followed by a final annealing step 72° C. for 10 min. All PCR products were cloned and sequenced to verify identity. The full-length nucleotide sequences for two R genes, one isolated from *Musa acuminata* (Calcutta 4) designated RGA5 and the other from *Musa acuminata* spp *malaccensis* designated RGA2, are presented in SEQ ID NO: 1 and 3, respectively.

Figure 3:
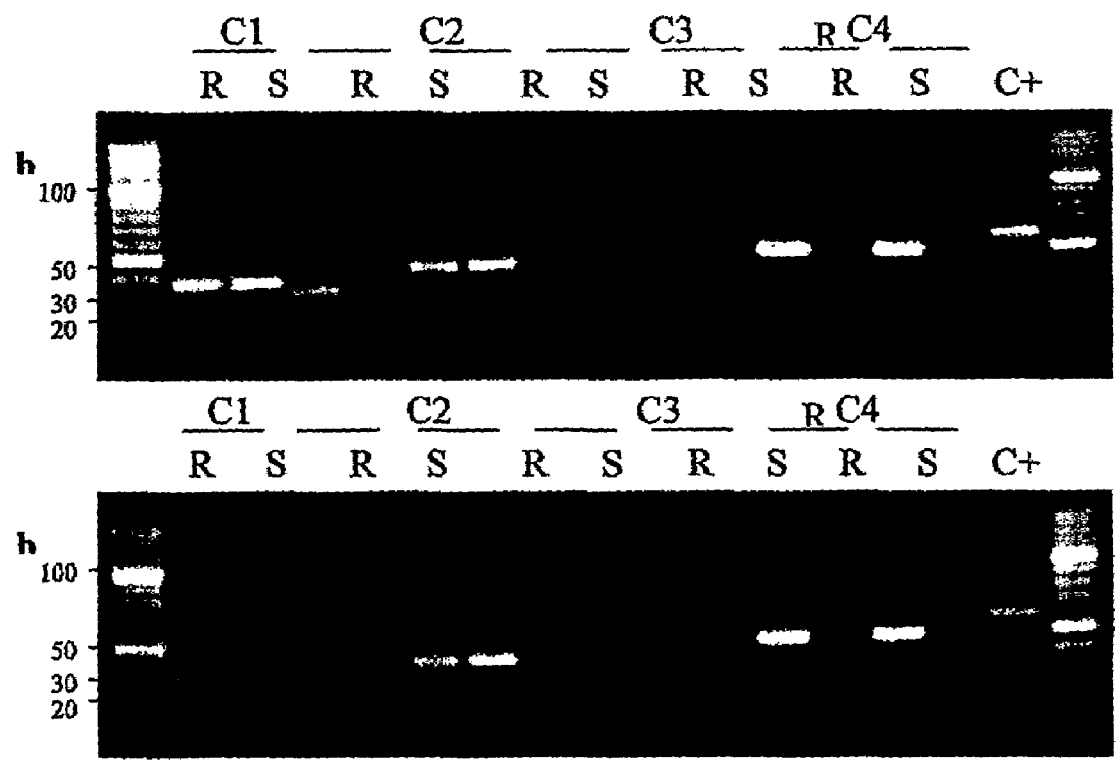
FIG. 3 is a photographic representation showing the migration of amplification products on an agarose gel following an RT-PCR using primers specific for each banana NBS class using template RNA from *M. acuminata* ssp. *malaccensis* resistant (R) or susceptible (S) plants. Total RNA was extracted from leaf or root tissue and treated with DNAase. C+ lanes, expected ~480 bp actin 1 cDNA fragment; C- lanes, no reverse transcriptase; AD, expected ~580 bp actin 1 genomic DNA fragment with ~100 bp intron included.

RT-PCR was then used to compare the expression of the R genes between *M. acuminata* spp *malaccensis* plants that were susceptible or resistant to *Fusarium oxysporum* fsp *cubense* (FOC). The results presented in FIG. 3 show that the RGA2 gene (see lanes C2) is transcribed in FOC resistant plants but not in FOC sensitive plants. This suggests that RGA2 may be an attractive candidate for conferring disease resistance to susceptible plants. The inventors propose to transform Cavendish, which is resistant to race I but susceptible to race 4, (i) with RGA2 only; (ii) with RGA5 and (iii) with both RGA2 and RGA5, under the control of a heterologous promoter (e.g., Ubi) or the native RGA2 promoter.

The disclosure of every patent, patent application, and publication cited herein is hereby incorporated herein by reference in its entirety.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

BIBLIOGRAPHY

Aarts N, Metz M, Holub E, Staskawic B, Daniels M and Parker J (1998). Different requirements for EDS1 and NDR1 by disease resistance genes define at least two R gene-mediated signalling pathways in *Arabidopsis*. Proc. Natl. Acad. Sci. USA. 95, 10306-10311.

Aarts M, Lintel G, Hekkert B, Holub E, Beynon J, Stiekema W and Pereira A (1998). Identification of R-gene homologous DNA fragments genetically linked to disease resistance loci in *Arabidopsis thaliana*. Mol. Plant-Microbe Interact. 11: 251-258.

Anderson P, Lawrence G, Morrish B, Finnegan E and Ellis J (1997). Inactivation of the flax rust resistance gene M associated with loss of a repeated unit within the leucine-rich repeat coding region. Plant cell. 9: 641-651.

Aravind L, Dixit V and Koonin E (1999). The domains of the death: evolution of the apoptosis machinery. Trends in biochemical science. 24: 47-53.

Asai T, Tena G, Plotnikova J, Willmann M, Chiu W, Gomez-Gomez L, Boiler T, Ausubel M and Sheen J (2002). MAP kinase signalling cascade in *Arabidopsis* innate immunity. Nature. 415. 977-983.

Baker B, Zambryski P, Staskawicz B and Dinesh-Kumar S (1997). Signaling in plant-microbe interactions. Science. 276, 726-733.

Ballvora A, Ercolano M, Weib J, Meksem K, Bormann C, Oberhagemann P, Salamini F and Gebhardt C (2002). The R1 gene for potato resistance to late blight (*Phytophtora infestans*) belongs to the leucine zipper/NBS/LRR class of plant resistance gene. The Plant Journal. 30, 361-371.

Becker D, Dugdale B, Smith M, Harding R and Dale J (2000). Genetic transformation of Cavendish banana (*Musa* spp. AAA group) cv 'Grand Nain' via microprojectile bombardment. Plant Cell Reports. 19, 229-234.

Bendahmane A, Kanyuka K and Baulcombe D (1999). The Rx gene from tomato controls separate virus resistance and cell death responses. Plant Cell. 11: 781-791.

Bentley S, Pegg K, Moore N, Davis R and Buddenhagen W (1998). Genetic variation among vegetative compatibility groups of *Fusarium oxysporum* f. sp. *cubense* analysed by DNA fingerprinting. Phytopathology 88: 1283-1293.

Bittner-Eddy P, Crute I, Holub E and Beynon J (2000). RPP13 is a simple locus in *Arabidopsis thaliana* for alleles that specify downy mildew resistance to different avirulence determinants in *peronospora parasitica*. The Plant Journal. 21, 177-188.

Bonas U and Lahaye T (2002). Plant disease resistance triggered by pathogen-derived molecules: refined models of specific recognition. Current opinion in microbiology. 5: 44-50.

Botella M, Pareker J, Frost L, Bittner-Eddy, Beynon J et al. (1998). Three genes of the *Arabidopsis* RPP1 complex resistance locus recognize distinct *Peronospora parasitica* avirulence deteminants. Plant cell 10: 1847-1860.

Brominonschenkel S, Fray A and Tanksley S (2000). The broad-spectrum tospovirus resistance gene Sw-5 of tomato is a homolog of the root-knot nematode resistance gene Mi. Molecular Plant Microbe Interactioin. 13, 1130-1138.

Brueggeman R, Rostoks N, Kudrna D, Killian A, Han F, Chen J, Druka A, Steffenson B and Kleinhofs A (2002). The barley steam rust-resistance gene Rpg1 is a novel disease-resistance gene with homology to receptor kinases. PNAS. 1-6.

Bryan G, Wu K, Farall L, Jia Y, Hershey H, McAdams S, Faulk K, Donaldson G, Tarchini R and Valent B (2000). A single amino acid difference distinguishes resistant and susceptible alleles of the rice blast resistance gene Pi-ta. Plant Cell. 12: 2033-2045.

Cai D, KIeine M, Kiffle S, Harloff H, Sanda N, Marcker K, Kein-Lankhorts R, Salentjn E, Lange W, Stiekema W, Wyss W, Grundler F and Jung C (1997). Positional cloning of a gene for nematode resistance in sugar beet. Science. 275, 832-834.

Cao H, Glazebrook J, Clarke J, Volko S and Dong X (1997). The *Arabidopsis* NPR1 gene that controls systemic acquired resistance encodes a novel protein containing ankyrin repeats. Cell. 88, 57-63.

FAO, 2001http://apps.fao.org/lim500/nph-wrap.pl!production.crops.primary&Domain=SUA&

Cao E H, Li X and Dong X (1998). Generation of broad-spectrum disease resistance by overexpression of an essential regulator gene in systemic acquired resistance. Proc Natl Acad Sci USA. 95, 6531-6536.

Century K, Shapiro A, Repetti P, Dahlbeck D, Holub E and Staskawicz J (1997). NDR1, a pathogen-induced component required for *Arabidopsis* disease resistance. Science. 278: 1963-1965.

Chern M, Fitzgerald H, Yadav R, Canlas P, Dong X and Ronald P (2001). Evidence for a disease-resistance pathway in rice similar to the NPR1—mediated signalling pathway in *Arabidopsis*. The plant Journal. 27, 101-113.

Cohn J, Sessa G and Martin G (2001). Innate immunity in plants. Current Opinion in Immunology. 13, 55-62.

Collins N, Drake J, Ayliffe M, Sun Q, Ellis J, Hulbert S, and Pryor T (1999). Molecular characterization of the Maize Rp1-D Rust resistance haplotype and its mutants. The Plant Cell. 11, 1365-1376.

Despres C, DeLong C, Glaze S, Liu E and Fobert P (2000). The *Arabidopsis* NPR1/NIM1 protein enhances the DNA binding activity of a subgroup of the TGA family of bZIP transcription factors. The Plant Cell. 12, 279-290.

Dixon M, Hatzixanthis K, Jones D, Harrison K, Jones J (1998). The tomato Cf-5 disease resistance gene and six homologs show pronounced allelic variation in leucine-rich repeat copy number. Plant Cell. 10, 1915-1925.

Dodds P, Lawrence G and Ellis J (2000). Six amino acid changes confined to the Leucine-Rich repeat B-strand/B-turn motif determine the difference between the P and P2 rust resistance specificities in flax. Plant Cell 13: 163-178.

Ellis J, Dodds P and Pryor T (2000). The generation of plant disease resistance gene specificities. Trends in Plant Science. 5, 373-379.

Ellis J and Jones D (1998). Structure and function of proteins controlling strain-specific pathogen resistance in plants. Current opinion in plant biology. 1, 288-293.

Endo T, Ikeo K and Gojobori T (1996). Large-scale search for genes on which positive selection may operate. Molecular Biology Evolution. 13, 685-690.

Ernst K, Kumar A, Kriseleit D, Kloos D, Phillips M and Ganal M (2002). The broad-spectrum potato cys nematode resistance gene (Hero) from tomato is the only member of a large gene family of NBS-LRR genes with and unusual amino acid repeat in the LRR region. Plant Journal. 31: 127-136.

Falk A, Feys B, Frost L, Jones J, Daniels M and Parker J (1999). EDS1, an essential component of R gene-mediated disease resistance in *Arabidopsis* has homology to eukaryotic lipases. Proc. Natl. Acad. Sci. USA. 96: 3292-3297.

Glazebrook J (2001). Genes controlling expression of defense responses in *Arabidopsis*. 4, 301-308.

Graham M, Mareck L, Lohnes D, Cregan P and Shoemaker R (2000). Expression and genome organization of resistance gene analogues in soybean. Genome. 43, 86-93.

Grant M, Godard L, Straube E, Ashfield T, Leward J, Sattler A, Innes R and Dangl J (1995). Structure of the *Arabidopsis* RPM1 enabling dual specifity disease resistance. Science. 269, 843-846.

Gassmann W, Rinsch M and Staskawicz B (1999). The *Arabidopsis* RPS4 bacterial-resistance gene is a member of the TIR-NBS-LRR family of disease resistance genes. Plant Journal. 20: 265-277.

Gomez-Gomez L and Boiler T (2000). FLS2: An LRR receptor-like kinase involved in the perception of the bacterial elicitor flagellin in *Arabidopsis*. Moll Cell. 5, 1003-1011.

Hammond-Kosack K and Jones J (1997). Plant resistance genes. Annu. Rev. Plant Physiol. Plant Mol. Biol. 48, 575-607.

Hughes L and Nei M (1988). Pattern of nucleotide substitution at major histocompatibility complex class I loci reveals overdominant selection. Nature. 335, 167-170.

Hulbert S, Webb C, Smith S and Sun Q (2001). Resistance gene complexes: evolution and utilization. Annu. Rev. Phytopathol. 39: 285-312.

Jia Y, McAdams S, Bryan G, Hershey P and Valent B (2000). Direct interaction of resistance gene and avirulence gene products confers rice blast resistance. EMBO J. 19, 4004-4014.

Johal G, and Briggs S (1992). Reductase activity encoded by the HM1 disease resistance gene in maize. Science. 258, 985-987.

Kanazin V, Mareck L and Shoemaker R (1996). Resistance gene analogs are conserved and clustered in soybean. Proc Natl Acad Sci USA. 93, 11746-11750.

Kawchuk L, Hachey J, Lynch D, Kulcsar F, Rooijen G, Waterer D, Robertson A, Kokko E, Byers R, Howard R, Fischer R and Prufer D (2001). Tomato Ve disease resistance genes encode cell surface-like receptors. PNAS. 98, 6511-6515.

Kimura M (1983). The neutral theory of molecular evolution. Cambridge University Press.

Kinkema M, Fan W and Dong X (2000). Nuclear localization of NPR1 is required for activation of PR gene expression. The plant cell. 12, 2339-2350.

Lagudah E, Moullet 0 and Appels R (1997). Map-based cloning of a resistance gene sequence encoding a nucleotide-binding domain and leucine rich region at the Cre3 nematode resistance locus of wheat. Genome. 40, 659-665.

Lawrence G J, Finnegan E J, Ayliffe M and Eliis J (1995). The L6 gene for flax rust resistance is related to the *Arabidopsis* bacterial resistance gene RPS2 and the tobacco viral resistance gene N. Plant Cell. 7: 1195-1206.

Leister D, Ballvora A, Salamini F and Gebhardt C (1996). A PCR-based approach for isolating pathogen resistance genes from potato with potential for wide application in plants. Nature Genetics: 14, 421-429.

Leister D, Kurth J, Laurie D, Yano M, Sasaki T, Devos K, Graner A and Schulze-Lefert P (1998). Rapid organization of resistance gene homologues in cereal genomes. Proc Natl Acad Sci USA. 95, 370-375.

May G, Afza R, Mason, Wiecko A, Novak F and Arntzen C (1995). Generation of transgenic banana (Musa acuminata) plants via *Agrobacterium*-mediated transformation. Bio/Technology. 13, 486-492.

Mes J, Van Doorn A, Wijbrandi J, Simons G, Cornelissen B and Haring M (2000). Expression of the *Fusarium* resistance gene I-2 colocalizes with the site of fungal containment. The plant journal. 23, 183-193.

Meyers B, Shen K, Rohani P, Gaut B and Michelmore R (1998). Receptor-like genes in the mayor resistance locus in lettuce are subject of divergent selection. Plant Cell. 11, 1833-1846.

Meyers B, Dickerman A, Michelmore R, Sivaramakrishnan S, Sobral B and Young N (1999). Plant disease resistance genes encode members of an ancient and diverse protein family within the nucleotide-binding superfamily. The Plant Journal. 20, 317-332.

Milligan S, Bodeau J. Yaghoobi J, Kaloshian I, Zabel P and Williamson V (1998). The root knot resistance gene Mi from tomato is a member of the leucine zipper, nucleotide binding site, leucine-rich repeat family of plant genes. The plant cell. 10, 1307-1319.

Mindrinos M, Katagiri F, Yu G and Ausubel F (1994). The *A. thaliana* disease resistance gene RPS2 encodes a protein containing a nucleotide-binding site and leucine-rich repeats. Cell. 78: 1089-1099.

Muskett P, Kahn K, Austin M, Moisan L, Sadanandom A, Shirasu K, Jones J and Parker J (2002). *Arabidopsis* RAR1 exerts rate-limiting control of R genes-mediated defenses against multiple pathogens. The plant cell. 14. 979-992.

Ortiz R, Ferris R and Vuylsteke D (1995). Banana and plantain breeding. In banana and plantains. Gowen, S. Ed. Chapman and Hall London. pp, 110-146.

Pan Q, Wendel J and Fluhr R (2000). Divergent evolution of plant NBS-LRR resistance gene homologues in dicot and cereal genomes. Journal of molecular evolution. 50: 203-213.

Parker J, Coleman M, Szabo V, Frost V, Schmidt R, Van der Biezen E, Moores T, Dean C, Daniels M and Jones J (1997) The *Arabidopsis* downy mildew resistance gene RPP5 shares similarity to the toll interleukine-1 receptors with N and L6. The Plant Cell. 9, 879-894.

Parniske M, Hammond-Kosack K, Golstein C, Thomas C, Jones D, Harrison K, Wulff B B, Jones J (1997) Novel disease resistance specificities result from sequence exchange between tandemly repeated genes at the Cf-4/9 locus of tomato. Cell. 91, 821-832

Ploetz R (2000). Panama disease: a classical and destructive disease of banana. Online. Plant Health Progress doi: 10.1094/PHP-2000-1240-01-HM.

Ploetz R and Pegg K (2000). Fungal disease of the root, corm and pseudosteam. In Diseases of banana, abaca and ensete. Jones, D. Ed. CABI.

Richter T and Ronald P (2000). The evolution of disease resistance genes. Plant Molecular Biology. 42, 195-204.

Rommens C and Kishore G (2000). Exploiting the full potential of disease-resistance genes for agricultural use. Curren opinion in biotechnology. 11, 120-125.

Ryals J, Weymann K, Lawton K, Friedrich L, Ellis D, Steiner H, Johnson J, Delaney T, Jesse T, Vos P and Uknes S (1997). The *Arabidopsis* NIM1 protein shows homology to the mammalian transcription factor inhibitor IkB. The Plant Cell. 9, 425-439.

Sagi L, Panis B, Remy S, Schoofs H, De Smet K, Swennen R and Cammue P (1995). Genetic transformation of banana and plantain (*Musa* spp) via particle bombardment. Bio/Techniques. 13, 481-485.

Salmeron J, Oldroyd E, Rommens C, Scofield S, Kim H, Lavelle D, Dahlbeck D and Staskawicz B (1996). Tomato Prf is a member of a leucine-rich repeat class of plant disease resistance gene and lies embedded within the Pto kinase gene cluster. Cell. 86, 123-133.

Shen K, Meyers B, Islam-Faridi M, Chin D, Stelly D and Michelmore R (1998). Resistance gene candidates identified by PCR with degenerate oligonucleotide primers Map to clusters of resistance genes in lettuce. Molecular Plant Pathogen Interaction. 11, 815-823.

Shirasu K, Lahaye T, Tan M, Zhou F, Azevedo C and Schulze-Lefert P (1999). A novel class of eukaryotic zinc-binding proteins is required for disease resistance signalling in barley and the development in *C. elegans*. Cell. 99: 355-366.

Simons G, Groenendijk J, Wijbrandi J, Reijans M, Groenen J, Diergaarde P, Van der Lee T, Bleeker M, Onstenk J, Both M, Raring M, Mes J, Cornelisse B, Zabeau M and Vos P (1998). Dissection of the *Fusarium* I2 gene cluster in tomato reveals six homologs and one active gene copy. The Plant Cell. 10, 1055-1068.

Song W, Wang G, Gardner J, Hoisten T, Ronald P (1997). Evolution of the rice Xa21 disease resistance gene family. Plant Cell 9: 1279-1287.

Song W, Wang G, Chen L et al. (1998). A receptor kinase-like protein encoded by the rice disease Xa21. Science. 270, 1804-1806.

Striver M and Custers J (2002). Engineering disease resistance in plants. Nature. 411: 865-868.

Tai T, Dahlbeck D, Clarck E, Gajiwala P, Pasion R, Whalen M, Stall R and Staskawicz J (1999). Expression of the Bs2 pepper gene confers resistance to bacteria spot disease in tomato. Proc Natl Acad Sci USA. 96, 14153-14158.

The *Arabidopsis* genome initiative (2000). Analysis of the genome sequence of the flowering plant, *Arabidopsis thaliana*. Nature. 408, 796-815.

Thomas C, Jones D, Parniske M, Harrison K, Balint-Kurti P et al. (1997). Characterization of the tomato Cf-4 gene for resistance to *Cladosporium fulvum* identifies sequences that determine recognitional specificity in Cf-4 and Cf-9. Plant Cell. 9, 2209-2224.

Tornero P, Merritt P, Sadanandom A, Shirasu K, Innes R, and Dangl J (2002). RAR1 and NDR1 contribute quantitatively to disease resistance in *Arabidopsis*, and their relative contributions are dependent on the R gene assayed. The plant cell. 14: 1005-1015

Van Der Biezein E and Jones D (1998). Plant disease-resistance proteins and the gene-for-gene concept. Trend in Biochemestry Science. 23, 454-456.

Van der Hoorri R, De Wit P and Joosten M (2002). Balancing selection favors guarding resistance proteins. Trends in plant science. 7: 67-71

Van der Vossen E, Rouppe van der Voort J, Kanyuka K, Bendahmane A, Sandbrink H et al. (2000). Homologue of a single resistance-gene cluster in potato confer resistance to distinct pathogens: a virus and a nematode. Plant Journal. 23: 567-576.

Wang G, Ruan D, Song W, Sideris S, Chen L, Pi L, Zhang S, Zhang Z, Fauquet C, Gaut B, Ronald P (1998). Xa21D encodes a receptor-like molecule with a leucine-rich repeat domain that determines race specific recognition and is subject to adaptive evolution. Plant Cell. 10, 1-15

Warren R, Hlenk A, Mowery P, Holub E, Inues R (1998). A mutation within the leucine-rich repeat domain of the *Arabidopsis* disease resistance gene RPS5 partially suppresses multiple bacterial and downy mildew resistance genes. Plant Cell. 10, 1439-1452.

Wees S, Swart E, Pelt J, Loon L and Pieterse C (2000). Enhancement of induced disease resistance by simultaneous activation of salycilate- and jasmonate-dependent defense pathways in *Arabidopsis thaliana*. Proc Natl Acad Sci USA. 97, 8711-8716.

Whitham S (1996). The N gene of tobacco confers resistance to tobacco mosaic virus in transgenic tomato. Proc Nafi Acad Sci USA. 93, 8776-8781.

Yoshimura S, Yamanouchi U, Katayose Y, Told S, Z X et al. (1998). Expression of Xa1, a bacterial blight-resistance gene in rice, is induced by bacterial inoculation. PNAS. 95, 1663-1668.

Yu D, Chen C and Chen Z (2001). Evidence for an important role of WRKY DNA binding proteins in the regulation of NPR1 gene expression. Plant Cell. 13: 1527-1540.

Yu Y, Buss G and Maroof M (1996). Isolation of a superfamily of candidate disease-resistance genes in soybean based on a conserved nucleotide-binding site. Proc Natl Acad Sci USA. 93, 11751-11756.

Zhang Y, Fan W, Kinkema M, Li X and Dong X (1999). Interaction of NPR1 with basic leucine zipper protein transcription factors that bind sequences required for salicylic acid and induction of PR-1 gene. Proc Natl Acad Sci USA. 96, 6523-6528.

Zou H, Henzel W, Liu X, Lutschg A and Wang X (1997). Apaf-1, a human protein homologous to *C. elegans* CED-4, participates in Cytochrome c-dependent activation of caspase-3. Cell. 90: 405-413.

Zhou J. Trifa Y, Silva, Pontier D, Lam E, Shah J, Klessig D (2000). NPR1 differentially interacts with members of the TGA/OBF family of transcription factors that bind an element of the PR-1 gene required for induction by salicylic acid. Mol Plant Microbe Interact. 13, 191-202.

What is claimed is:

1. An isolated polynucleotide comprising a nucleotide sequence selected from the group consisting of:
   (a) a nucleotide sequence that encodes a polypeptide conferring *fusarium* resistance to a plant, or a full length complement of the nucleotide sequence, wherein the nucleotide sequence is selected from the sequence set forth in SEQ ID NO: 1 or 3;
   (b) a nucleotide sequence that encodes a polypeptide conferring *fusarium* resistance to a plant and comprising the amino acid sequence set forth in SEQ ID NO: 2 or 4, or a full length complement of the nucleotide sequence; and
   (c) a nucleotide sequence that encodes a polypeptide that confers *fusarium* resistance to a plant, or a full length complement of the nucleotide sequence, wherein the nucleotide sequence hybridizes to a full length complement of a nucleotide sequence selected from the group consisting of the sequence set forth in SEQ ID NO: 1 or 3 and a nucleotide sequence that encodes the amino acid sequence set forth in SEQ ID NO: 2 or 4, under high stringency conditions, wherein the conditions comprise hybridization at 65° C. in 1% BSA, 1 mM EDTA, 0.5 M NaHPO$_4$ (pH 7.2), 7% SDS, and washing at 65° C. in 0.2×SSC, 0.1% SDS.

2. A nucleic acid construct, comprising the polynucleotide according to claim 1 operably connected to a regulatory element, which is operable in the plant.

3. The nucleic acid construct according to claim 2, wherein the construct is a vector.

4. An isolated host cell containing the nucleic acid construct according to claim 2.

5. The host cell according to claim 4, wherein the host cell is a plant cell.

6. The host cell according to claim 5, wherein the plant cell has the nucleic acid construct incorporated into its nucleome.

7. The host cell according to claim 5, wherein the plant cell has the nucleic acid construct stably incorporated into its genome.

8. A plant containing a cell comprising the nucleic acid construct according to claim 2.

9. The plant according to claim 8, wherein the plant cell has the nucleic acid construct stably incorporated into its genome.

10. A method for modulating disease resistance in a plant, the method comprising introducing a construct into the genome of the plant and regenerating a stably transformed plant, the construct comprising a regulatory element operably connected to a nucleotide sequence selected from the group consisting of: (a) a nucleotide sequence that encodes a polypeptide conferring *fusarium* resistance to a plant, wherein the nucleotide sequence is selected from the sequence set forth in SEQ ID NO:1 or 3; (b) a nucleotide sequence that encodes a polypeptide conferring *fusarium* resistance to a plant and comprising the amino acid sequence set forth in SEQ ID NO: 2 or 4; and (c) a nucleotide sequence that hybridizes to the full length complement of (a) or (b) under high stringency conditions, wherein the conditions comprise hybridization at 65° C. in 1% BSA, 1 mM EDTA, 0.5 M NaHPO$_4$ (pH 7.2), 7% SDS, and washing at 65° C. in 0.2×SSC, 0.1% SDS.

11. The method according to claim 10, wherein the construct is introduced into regenerable plant cells so as to yield transformed plant cells.

12. The method according to claim 11, wherein the regenerable cells are regenerable dicotyledonous plant cells.

13. The method according to claim 11, wherein the regenerable cells are regenerable monocotyledonous plant cells.

14. The method according to claim 11, wherein regenerable cells are regenerable graminaceous plant cells.

15. The method according to claim 11, wherein regenerable cells are regenerable non-graminaceous monocotyledonous plant cells.

16. The method according to claim 11, wherein regenerable cells are regenerable banana cells.

17. The method according to claim 11, wherein the expression of the polynucleotide confers the transgenic plant with enhanced resistance to disease.

18. The method according to claim 17, wherein disease is caused by a fungal pathogen.

19. The method according to claim 17, wherein disease is caused by soil borne fungi.

20. The method according to claim 17, wherein disease is caused by *Fusarium* species.

21. The method of claim 17, further comprising the step of growing the transformed plant to produce a transformed progeny, wherein the progeny is selected from seed, a plant part, and tissue.

22. A method of breeding a plant for *fusarium* resistance, the method comprising identifying a plant that is resistant to *fusarium* wilt by detecting expression in the plant of a polynucleotide; and transferring from the plant genetic material corresponding to the polynucleotide via crossing and backcrossing to another plant of the same species, wherein the polynucleotide comprises a nucleotide sequence that is selected from the group consisting of: (a) a nucleotide sequence that encodes a polypeptide conferring *fusarium* resistance to a plant, or the full length complement of the nucleotide sequence, wherein the nucleotide sequence is SEQ ID NO: 1 or 3, (b) a nucleotide sequence that encodes a polypeptide conferring *fusarium* resistance to a plant and comprising the amino acid sequence set forth in SEQ ID NO: 2 or 4 or the full length complement of the nucleotide sequence; and (c) a nucleotide sequence that hybridizes to the full length complement of (a) or (b) under high stringency conditions, wherein the conditions comprise hybridization at 65° C. in 1% BSA, 1 mM EDTA, 0.5 M NaHPO4 (pH 7.2), 7% SDS, and washing at 65° C. in 0.2×SSC, 0.1% SDS.

23. The method according to claim 22, wherein the other plant is susceptible to *fusarium* wilt.

24. A method according to claim 22, wherein the genetic material comprises naturally-occurring DNA.

25. An isolated polynucleotide comprising a nucleotide sequence encoding an amino acid sequence selected from the group consisting of:
   (i) an amino acid sequence which confers *fusarium* resistance to a plant, wherein the amino acid sequence is set forth in SEQ ID NO: 2 or 4;
   (ii) an amino acid sequence which confers *fusarium* resistance to a plant and which is encoded by the nucleotide sequence set forth in SEQ ID NO: 1 or 3; and
   (iii) an amino acid sequence which confers *fusarium* resistance to a plant and which is encoded by a nucleotide sequence that hybridizes under high stringency conditions to the full length complement of the sequence set forth in SEQ ID NO: 1 or 3, wherein the conditions comprise hybridization at 65° C. in 1% BSA, 1 mM EDTA, 0.5 M NaHPO4 (pH 7.2), 7% SDS and washing at 65° C. in 0.2×SSC, 0.1% SDS.

* * * * *

SEQUENCE LISTING

```
<160> NUMBER OF SEQ ID NOS: 7

<210> SEQ ID NO 1
<211> LENGTH: 4380
<212> TYPE: DNA
<213> ORGANISM: Musa acuminata
<220> FEATURE:
<221> NAME/KEY: CDS
<222> LOCATION: (1)..(4323)

<400> SEQUENCE: 1 atg tcg acg gcg cta gta atc gga gga tgg ttc gcg caa agc ttc atc      48
Met Ser Thr Ala Leu Val Ile Gly Gly Trp Phe Ala Gln Ser Phe Ile
1               5                   10                  15 cag acg ttg ctc gac aag gcc agc aac tgc gcg atc caa caa ctc gcg      96
Gln Thr Leu Leu Asp Lys Ala Ser Asn Cys Ala Ile Gln Gln Leu Ala
            20                  25                  30 cgg cgc cgc ggc ctt cac gat gac ctg agg cgg ctg cgg acg tct ctg     144
Arg Arg Arg Gly Leu His Asp Asp Leu Arg Arg Leu Arg Thr Ser Leu
        35                  40                  45 ctc cgg atc cat gcc atc ctc gac aag gca gag acg agg tgg aac cat     192
Leu Arg Ile His Ala Ile Leu Asp Lys Ala Glu Thr Arg Trp Asn His
    50                  55                  60 aaa aac acg agc ttg gtg gag ctg gtg agg cag ctc aag gat gct gcc     240
Lys Asn Thr Ser Leu Val Glu Leu Val Arg Gln Leu Lys Asp Ala Ala
65                  70                  75                  80
```

-continued

| | |
|---|---|
| tat gac gcc gag gac tta ctg gag gag ttg gag tac caa gcc gcg aag<br>Tyr Asp Ala Glu Asp Leu Leu Glu Glu Leu Glu Tyr Gln Ala Ala Lys<br>  85                  90                  95 | 288 |
| caa aag gtc gag cac cgg gga gac cag ata agc gac ctc ttt tct ttt<br>Gln Lys Val Glu His Arg Gly Asp Gln Ile Ser Asp Leu Phe Ser Phe<br>           100                 105                 110 | 336 |
| tcc ctt agt act gcg agc gag tgg ttg ggt gcc gat ggt gat gat gct<br>Ser Leu Ser Thr Ala Ser Glu Trp Leu Gly Ala Asp Gly Asp Asp Ala<br>        115                 120                 125 | 384 |
| ggg act cga ttg agg gag atc cag ggg aag ctg tgc aac att gct gcc<br>Gly Thr Arg Leu Arg Glu Ile Gln Gly Lys Leu Cys Asn Ile Ala Ala<br>   130                 135                 140 | 432 |
| gat atg atg gat gtc atg cag cta ttg gca ccc gat gat ggg gga aga<br>Asp Met Met Asp Val Met Gln Leu Leu Ala Pro Asp Asp Gly Gly Arg<br>145                 150                 155                 160 | 480 |
| caa ttc gac tgg aag gtg gtg aga aga gaa acg agc tct ttc ttg acc<br>Gln Phe Asp Trp Lys Val Val Arg Arg Glu Thr Ser Ser Phe Leu Thr<br>                165                 170                 175 | 528 |
| gaa acc gtc gtg ttt ggt cgg gac caa gaa agg gag aaa gta gta gaa<br>Glu Thr Val Val Phe Gly Arg Asp Gln Glu Arg Glu Lys Val Val Glu<br>            180                 185                 190 | 576 |
| ttg ctg ttg gat tca gga tct ggt aac agt agc ttc tct gtc tta ccc<br>Leu Leu Leu Asp Ser Gly Ser Gly Asn Ser Ser Phe Ser Val Leu Pro<br>        195                 200                 205 | 624 |
| ctc gtc gga atc gga ggg gtt ggg aag acg act ctg gct cag ctc gtg<br>Leu Val Gly Ile Gly Gly Val Gly Lys Thr Thr Leu Ala Gln Leu Val<br>   210                 215                 220 | 672 |
| tac aac gac aat cgt gtc ggc aac tat ttc cac ctc aag gtt tgg gtc<br>Tyr Asn Asp Asn Arg Val Gly Asn Tyr Phe His Leu Lys Val Trp Val<br>225                 230                 235                 240 | 720 |
| tgt gta tcc gac aat ttc aat gtg aag aga ctg acc aaa gag ata atc<br>Cys Val Ser Asp Asn Phe Asn Val Lys Arg Leu Thr Lys Glu Ile Ile<br>                245                 250                 255 | 768 |
| gag tct gct acc aag gtg gaa caa tct gac aaa ttg aac ttg gac acc<br>Glu Ser Ala Thr Lys Val Glu Gln Ser Asp Lys Leu Asn Leu Asp Thr<br>            260                 265                 270 | 816 |
| ctg caa cag atc ctc aag gag aag att gct tca gag agg ttt ctg cta<br>Leu Gln Gln Ile Leu Lys Glu Lys Ile Ala Ser Glu Arg Phe Leu Leu<br>        275                 280                 285 | 864 |
| gtc ctc gat gat gtg tgg agc gaa aac agg gat gac tgg gaa agg ctg<br>Val Leu Asp Asp Val Trp Ser Glu Asn Arg Asp Asp Trp Glu Arg Leu<br>   290                 295                 300 | 912 |
| tgc gca cca cta agg ttt gca gca aga ggc agc aag gtt ata gtc aca<br>Cys Ala Pro Leu Arg Phe Ala Ala Arg Gly Ser Lys Val Ile Val Thr<br>305                 310                 315                 320 | 960 |
| act cga gac aca aag att gcc agc atc att ggc aca atg aag gaa att<br>Thr Arg Asp Thr Lys Ile Ala Ser Ile Ile Gly Thr Met Lys Glu Ile<br>                325                 330                 335 | 1008 |
| tcg ctc gat ggt ctc cag gat gat gct tac tgg gag ctg ttc aag aaa<br>Ser Leu Asp Gly Leu Gln Asp Asp Ala Tyr Trp Glu Leu Phe Lys Lys<br>            340                 345                 350 | 1056 |
| tgt gca ttt ggt tct gtg aac ccc cag gag cat cta gag ctc gag gtt<br>Cys Ala Phe Gly Ser Val Asn Pro Gln Glu His Leu Glu Leu Glu Val<br>        355                 360                 365 | 1104 |
| atc ggt aga aag att gct ggt aag ttg aag ggc tca ccg cta gca gca<br>Ile Gly Arg Lys Ile Ala Gly Lys Leu Lys Gly Ser Pro Leu Ala Ala<br>   370                 375                 380 | 1152 |
| aaa aca cta gga agc ttg ttg cgg ttg gat gtc agc caa gaa cac tgg<br>Lys Thr Leu Gly Ser Leu Leu Arg Leu Asp Val Ser Gln Glu His Trp<br>385                 390                 395                 400 | 1200 |

-continued

```
aga act ata atg gaa agt gag gta tgg caa ctg cca caa gct gaa aat    1248
Arg Thr Ile Met Glu Ser Glu Val Trp Gln Leu Pro Gln Ala Glu Asn
            405                 410                 415 gaa ata ttg cct gtt cta tgg ctg agc tat caa cac ctt ccc gga cat    1296
Glu Ile Leu Pro Val Leu Trp Leu Ser Tyr Gln His Leu Pro Gly His
        420                 425                 430 ctt aga cag tgt ttc gct ttt tgc gct gtg ttt cac aaa gat tat tta    1344
Leu Arg Gln Cys Phe Ala Phe Cys Ala Val Phe His Lys Asp Tyr Leu
    435                 440                 445 ttc tat aaa cat gag ttg atc cag act tgg att gca gaa ggc ttc att    1392
Phe Tyr Lys His Glu Leu Ile Gln Thr Trp Ile Ala Glu Gly Phe Ile
450                 455                 460 gca cat caa gga aac aag agg atg gaa gat gtc gga agc agc tac ttc    1440
Ala His Gln Gly Asn Lys Arg Met Glu Asp Val Gly Ser Ser Tyr Phe
465                 470                 475                 480 cat gag ctt gtt aat agg tct ttc ttt cag gaa tct cgg tgg aga ggg    1488
His Glu Leu Val Asn Arg Ser Phe Phe Gln Glu Ser Arg Trp Arg Gly
                485                 490                 495 cga tat gtg atg cat gac ctc ata cac gat ctt gcc caa ttt ata tca    1536
Arg Tyr Val Met His Asp Leu Ile His Asp Leu Ala Gln Phe Ile Ser
            500                 505                 510 gtg gga gag tgt cat agg ata gat gat gac aag tcc aaa gag acc cct    1584
Val Gly Glu Cys His Arg Ile Asp Asp Asp Lys Ser Lys Glu Thr Pro
        515                 520                 525 agt acg act cgt cat cta tca gta gca tta act gag caa atg aag ttg    1632
Ser Thr Thr Arg His Leu Ser Val Ala Leu Thr Glu Gln Met Lys Leu
    530                 535                 540 gtg gat ttt tca ggt tac aat aaa ttg cgg acc ctt atg atc aac aat    1680
Val Asp Phe Ser Gly Tyr Asn Lys Leu Arg Thr Leu Met Ile Asn Asn
545                 550                 555                 560 cag aga aat cag tat cca tat atg act aaa gtc aac agc tgc ttg ttg    1728
Gln Arg Asn Gln Tyr Pro Tyr Met Thr Lys Val Asn Ser Cys Leu Leu
                565                 570                 575 cct cat agc ttg ttc aaa aga ctg aaa aga atc cat gtt tta gtt ttg    1776
Pro His Ser Leu Phe Lys Arg Leu Lys Arg Ile His Val Leu Val Leu
            580                 585                 590 cag aag tgt ggc atg aaa gag ttg cct gat att atc ggt gac ttg ata    1824
Gln Lys Cys Gly Met Lys Glu Leu Pro Asp Ile Ile Gly Asp Leu Ile
        595                 600                 605 caa ctt cgg tac ctt gac ata tcc tac aat gct tgc att cag agg ttg    1872
Gln Leu Arg Tyr Leu Asp Ile Ser Tyr Asn Ala Cys Ile Gln Arg Leu
    610                 615                 620 ccc gag tca ttg tgc gac ctt tac aat ctg caa gca ctg agg cta tgg    1920
Pro Glu Ser Leu Cys Asp Leu Tyr Asn Leu Gln Ala Leu Arg Leu Trp
625                 630                 635                 640 ggc tgt caa tta cgg agt ttc cca caa ggc atg agc aag ctg atc aac    1968
Gly Cys Gln Leu Arg Ser Phe Pro Gln Gly Met Ser Lys Leu Ile Asn
                645                 650                 655 ttg agg caa ctt cgt gta gaa gat gag ata att tcc aag ata tat gag    2016
Leu Arg Gln Leu Arg Val Glu Asp Glu Ile Ile Ser Lys Ile Tyr Glu
            660                 665                 670 gtt ggg aag ctg att tct ctg caa gaa ttg tct gca ttc aaa gtg cta    2064
Val Gly Lys Leu Ile Ser Leu Gln Glu Leu Ser Ala Phe Lys Val Leu
        675                 680                 685 aat aat cat gga aac aaa ctt gca gaa cta agt ggt ttg aca caa ctc    2112
Asn Asn His Gly Asn Lys Leu Ala Glu Leu Ser Gly Leu Thr Gln Leu
    690                 695                 700 cgc agc act cta cga att aca aat ctt gaa aat gta ggg agt aaa gaa    2160
Arg Ser Thr Leu Arg Ile Thr Asn Leu Glu Asn Val Gly Ser Lys Glu
705                 710                 715                 720
```

```
gaa gca agc aag gct aaa ctg cac agg aaa cag tat ctt gaa gca tta     2208
Glu Ala Ser Lys Ala Lys Leu His Arg Lys Gln Tyr Leu Glu Ala Leu
            725                 730                 735 gag tta gag tgg gca gct ggc cag gtt tcc agc ttg gag cat gag tta     2256
Glu Leu Glu Trp Ala Ala Gly Gln Val Ser Ser Leu Glu His Glu Leu
            740                 745                 750 ctt gtc tcg gag gaa gta ctt tta ggt ctc caa cca cat cac ttc ctc     2304
Leu Val Ser Glu Glu Val Leu Leu Gly Leu Gln Pro His His Phe Leu
            755                 760                 765 aaa agt ttg aca atc aga ggg tac agt ggt gca aca gta ccc agt tgg     2352
Lys Ser Leu Thr Ile Arg Gly Tyr Ser Gly Ala Thr Val Pro Ser Trp
            770                 775                 780 ctg gat gtg aaa atg cta ccg aac ttg gga act ttt aaa cta gag aac     2400
Leu Asp Val Lys Met Leu Pro Asn Leu Gly Thr Leu Lys Leu Glu Asn
785                 790                 795                 800 tgt aca aga ctg gag ggt ctt tca tat att gga caa ctg cca cat ctc     2448
Cys Thr Arg Leu Glu Gly Leu Ser Tyr Ile Gly Gln Leu Pro His Leu
            805                 810                 815 aag gtc ctt cat atg aag aga atg cct gtg gtg aaa caa atg agt cat     2496
Lys Val Leu His Met Lys Arg Met Pro Val Val Lys Gln Met Ser His
            820                 825                 830 gaa tta tgt ggc tgt acg aaa agc aag ttg ttc cct agg cta gaa gag     2544
Glu Leu Cys Gly Cys Thr Lys Ser Lys Leu Phe Pro Arg Leu Glu Glu
            835                 840                 845 tta gta ctg gag gat atg cca aca ttg aaa gaa ttc ccg aat ctt gca     2592
Leu Val Leu Glu Asp Met Pro Thr Leu Lys Glu Phe Pro Asn Leu Ala
850                 855                 860 caa ctt cct tgt ctc aag att att cac atg aag aac atg ttt gca gta     2640
Gln Leu Pro Cys Leu Lys Ile Ile His Met Lys Asn Met Phe Ala Val
865                 870                 875                 880 aaa cat ata ggt cgt gaa tta tat ggt gat ata gag agc aat tgt ttt     2688
Lys His Ile Gly Arg Glu Leu Tyr Gly Asp Ile Glu Ser Asn Cys Phe
            885                 890                 895 cta tca tta gaa gag ctt gtg ctg cag gac atg ctg aca ttg gag gaa     2736
Leu Ser Leu Glu Glu Leu Val Leu Gln Asp Met Leu Thr Leu Glu Glu
            900                 905                 910 ctc cca aat ctt gga caa ctt cca cat ctt aag gtt att cac atg aag     2784
Leu Pro Asn Leu Gly Gln Leu Pro His Leu Lys Val Ile His Met Lys
            915                 920                 925 aac atg tct gca ctg aaa ctt ata ggt cgt gaa tta tgt gat tct aga     2832
Asn Met Ser Ala Leu Lys Leu Ile Gly Arg Glu Leu Cys Asp Ser Arg
930                 935                 940 gag aaa att tgg ttt cct agg cta gaa gtg cta gtg ctg aag aac atg     2880
Glu Lys Ile Trp Phe Pro Arg Leu Glu Val Leu Val Leu Lys Asn Met
945                 950                 955                 960 ctg gca ctg gag gaa ctc cca agc ttg gac aac ttc cgt gtc tca aga     2928
Leu Ala Leu Glu Glu Leu Pro Ser Leu Asp Asn Phe Arg Val Ser Arg
            965                 970                 975 ttc ttc gca tcc agt gtc gaa gta ggc cat gga ctc ttt agt gct acg     2976
Phe Phe Ala Ser Ser Val Glu Val Gly His Gly Leu Phe Ser Ala Thr
            980                 985                 990 agg aat aaa tgg ttt cca agg ctg gaa gag cta gaa atc aag ggc atg     3024
Arg Asn Lys Trp Phe Pro Arg Leu Glu Glu Leu Glu Ile Lys Gly Met
            995                 1000                1005 ctg aca ttt gag gaa ctc cat tct ctt gaa aaa ctg cca tgt ctc         3069
Leu Thr Phe Glu Glu Leu His Ser Leu Glu Lys Leu Pro Cys Leu
            1010                1015                1020 aag gtt ttc cgc atc aag gga ttg cca gca gtg aaa aag ata ggc         3114
Lys Val Phe Arg Ile Lys Gly Leu Pro Ala Val Lys Lys Ile Gly
            1025                1030                1035
```

-continued

| | | | | | | | | | | | | |
|---|---|---|---|---|---|---|---|---|---|---|---|---|
| cat | gga | tta | ttt | gat | tct | acc | tgt | cag | aga | gag | tgt | ttt | cca | agg | 3159 |
| His | Gly | Leu | Phe | Asp | Ser | Thr | Cys | Gln | Arg | Glu | Cys | Phe | Pro | Arg | |
| | 1040 | | | | | 1045 | | | | | 1050 | | | | |

| ttg | gaa | gat | ctc | gta | tta | agc | gac | atg | cca | gca | tgg | gaa | gag | tgg | 3204 |
| Leu | Glu | Asp | Leu | Val | Leu | Ser | Asp | Met | Pro | Ala | Trp | Glu | Glu | Trp | |
| 1055 | | | | | 1060 | | | | | 1065 | | | | | |

| tcg | tgg | gct | gaa | agg | gag | gag | tta | ttt | tcc | tgc | ttg | tgt | aga | ctt | 3249 |
| Ser | Trp | Ala | Glu | Arg | Glu | Glu | Leu | Phe | Ser | Cys | Leu | Cys | Arg | Leu | |
| | 1070 | | | | | 1075 | | | | | 1080 | | | | |

| aaa | att | gaa | caa | tgc | ccc | aaa | ctt | aaa | tgc | ttg | ctt | ccc | atc | cct | 3294 |
| Lys | Ile | Glu | Gln | Cys | Pro | Lys | Leu | Lys | Cys | Leu | Leu | Pro | Ile | Pro | |
| 1085 | | | | | 1090 | | | | | 1095 | | | | | |

| cat | tct | ctc | ata | aaa | ctt | gaa | tta | tgg | caa | gtt | ggg | ctg | aca | gga | 3339 |
| His | Ser | Leu | Ile | Lys | Leu | Glu | Leu | Trp | Gln | Val | Gly | Leu | Thr | Gly | |
| | 1100 | | | | | 1105 | | | | | 1110 | | | | |

| ctt | cca | gga | tta | tgc | aaa | gga | att | ggt | gga | ggt | agc | agc | act | aga | 3384 |
| Leu | Pro | Gly | Leu | Cys | Lys | Gly | Ile | Gly | Gly | Gly | Ser | Ser | Thr | Arg | |
| 1115 | | | | | 1120 | | | | | 1125 | | | | | |

| act | gct | tct | ctc | tca | ctc | ttg | cac | att | att | aaa | tgt | cca | aat | ctg | 3429 |
| Thr | Ala | Ser | Leu | Ser | Leu | Leu | His | Ile | Ile | Lys | Cys | Pro | Asn | Leu | |
| | 1130 | | | | | 1135 | | | | | 1140 | | | | |

| aga | aat | ctg | gga | gaa | ggg | ttg | cta | tca | aac | cac | ctg | cca | cat | atc | 3474 |
| Arg | Asn | Leu | Gly | Glu | Gly | Leu | Leu | Ser | Asn | His | Leu | Pro | His | Ile | |
| 1145 | | | | | 1150 | | | | | 1155 | | | | | |

| aat | gct | att | cgg | ata | tgg | gaa | tgt | gct | gaa | ctg | ttg | tgg | ctg | cct | 3519 |
| Asn | Ala | Ile | Arg | Ile | Trp | Glu | Cys | Ala | Glu | Leu | Leu | Trp | Leu | Pro | |
| | 1160 | | | | | 1165 | | | | | 1170 | | | | |

| gtc | aag | agg | ttt | aga | gaa | ttc | acc | acc | ctt | gag | aac | ttg | tca | ata | 3564 |
| Val | Lys | Arg | Phe | Arg | Glu | Phe | Thr | Thr | Leu | Glu | Asn | Leu | Ser | Ile | |
| 1175 | | | | | 1180 | | | | | 1185 | | | | | |

| agg | aac | tgc | ccc | aag | ctc | atg | agc | atg | aca | cag | tgt | gag | gag | aat | 3609 |
| Arg | Asn | Cys | Pro | Lys | Leu | Met | Ser | Met | Thr | Gln | Cys | Glu | Glu | Asn | |
| | 1190 | | | | | 1195 | | | | | 1200 | | | | |

| gac | ctc | ctc | ctc | ccg | ccg | tta | atc | aag | gca | cta | gaa | ttg | ggt | gac | 3654 |
| Asp | Leu | Leu | Leu | Pro | Pro | Leu | Ile | Lys | Ala | Leu | Glu | Leu | Gly | Asp | |
| 1205 | | | | | 1210 | | | | | 1215 | | | | | |

| tgt | gga | aat | ctt | ggg | aaa | tcg | ctg | cct | gga | tgc | cta | cac | aac | ctc | 3699 |
| Cys | Gly | Asn | Leu | Gly | Lys | Ser | Leu | Pro | Gly | Cys | Leu | His | Asn | Leu | |
| | 1220 | | | | | 1225 | | | | | 1230 | | | | |

| agc | tca | ctt | act | cag | ttg | gcg | ata | tcc | aat | tgt | cca | tac | atg | gta | 3744 |
| Ser | Ser | Leu | Thr | Gln | Leu | Ala | Ile | Ser | Asn | Cys | Pro | Tyr | Met | Val | |
| 1235 | | | | | 1240 | | | | | 1245 | | | | | |

| tcc | ctt | cca | agg | gaa | gta | atg | ctt | cac | ttg | aag | gaa | ctt | gga | act | 3789 |
| Ser | Leu | Pro | Arg | Glu | Val | Met | Leu | His | Leu | Lys | Glu | Leu | Gly | Thr | |
| | 1250 | | | | | 1255 | | | | | 1260 | | | | |

| gta | agg | atc | gag | aat | tgt | gat | ggg | ctg | gga | tca | ata | gag | ggt | tta | 3834 |
| Val | Arg | Ile | Glu | Asn | Cys | Asp | Gly | Leu | Gly | Ser | Ile | Glu | Gly | Leu | |
| 1265 | | | | | 1270 | | | | | 1275 | | | | | |

| caa | gtt | ctc | aaa | tca | ctc | aag | aga | ttg | gca | atc | ata | gga | tgt | ccc | 3879 |
| Gln | Val | Leu | Lys | Ser | Leu | Lys | Arg | Leu | Ala | Ile | Ile | Gly | Cys | Pro | |
| | 1280 | | | | | 1285 | | | | | 1290 | | | | |

| agg | ctt | ttg | cta | aat | gaa | ggg | gat | gag | caa | ggg | gag | gtc | ttg | tca | 3924 |
| Arg | Leu | Leu | Leu | Asn | Glu | Gly | Asp | Glu | Gln | Gly | Glu | Val | Leu | Ser | |
| 1295 | | | | | 1300 | | | | | 1305 | | | | | |

| ctg | ctt | gaa | tta | tca | gta | gat | aaa | aca | gcc | cta | ctt | aaa | ctc | tca | 3969 |
| Leu | Leu | Glu | Leu | Ser | Val | Asp | Lys | Thr | Ala | Leu | Leu | Lys | Leu | Ser | |
| | 1310 | | | | | 1315 | | | | | 1320 | | | | |

| ctt | ata | aaa | aat | aca | cta | cca | ttc | atc | cat | tct | ctc | aga | atc | atc | 4014 |
| Leu | Ile | Lys | Asn | Thr | Leu | Pro | Phe | Ile | His | Ser | Leu | Arg | Ile | Ile | |
| 1325 | | | | | 1330 | | | | | 1335 | | | | | |

-continued

```
tgg tct cct cag aaa gtg atg ttt gac ttg gag gag cag gaa ttg        4059
Trp Ser Pro Gln Lys Val Met Phe Asp Leu Glu Glu Gln Glu Leu
    1340            1345                1350 gtg cac agc ctc aca gct ctc agg cgc ctt gaa ttc ttc aga tgc        4104
Val His Ser Leu Thr Ala Leu Arg Arg Leu Glu Phe Phe Arg Cys
1355                1360                1365 aag aat ctc cag tcc ttg cca aca gag ttg cat acc ctt cct tcc        4149
Lys Asn Leu Gln Ser Leu Pro Thr Glu Leu His Thr Leu Pro Ser
    1370                1375                1380 ctc cat gct ttg gtt gta agt gac tgc cca cag atc caa tca ctg        4194
Leu His Ala Leu Val Val Ser Asp Cys Pro Gln Ile Gln Ser Leu
    1385                1390                1395 ccg gag aag gga ctc ccg aca ctc ctc aca gat tta gga ttt gac        4239
Pro Glu Lys Gly Leu Pro Thr Leu Leu Thr Asp Leu Gly Phe Asp
    1400                1405                1410 cat tgc cac cca gtg ctg act gcg caa ctg gaa aag cac ctg gca        4284
His Cys His Pro Val Leu Thr Ala Gln Leu Glu Lys His Leu Ala
    1415                1420                1425 gag atg aag agc tca ggt cga ttt cac cca gtt tat gca taggcaacat     4333
Glu Met Lys Ser Ser Gly Arg Phe His Pro Val Tyr Ala
    1430                1435                1440 gagtgaggat ggagaaaggg gagtggaaga gaaagatttc gattgcc                4380

<210> SEQ ID NO 2
<211> LENGTH: 1441
<212> TYPE: PRT
<213> ORGANISM: Musa acuminata

<400> SEQUENCE: 2

Met Ser Thr Ala Leu Val Ile Gly Gly Trp Phe Ala Gln Ser Phe Ile
1               5                   10                  15

Gln Thr Leu Leu Asp Lys Ala Ser Asn Cys Ala Ile Gln Gln Leu Ala
            20                  25                  30

Arg Arg Arg Gly Leu His Asp Asp Leu Arg Arg Leu Thr Ser Leu
        35                  40                  45

Leu Arg Ile His Ala Ile Leu Asp Lys Ala Glu Thr Arg Trp Asn His
    50                  55                  60

Lys Asn Thr Ser Leu Val Glu Leu Val Arg Gln Leu Lys Asp Ala Ala
65                  70                  75                  80

Tyr Asp Ala Glu Asp Leu Leu Glu Glu Leu Glu Tyr Gln Ala Ala Lys
                85                  90                  95

Gln Lys Val Glu His Arg Gly Asp Gln Ile Ser Asp Leu Phe Ser Phe
            100                 105                 110

Ser Leu Ser Thr Ala Ser Glu Trp Leu Gly Ala Asp Gly Asp Asp Ala
        115                 120                 125

Gly Thr Arg Leu Arg Glu Ile Gln Gly Lys Leu Cys Asn Ile Ala Ala
    130                 135                 140

Asp Met Met Asp Val Met Gln Leu Leu Ala Pro Asp Asp Gly Gly Arg
145                 150                 155                 160

Gln Phe Asp Trp Lys Val Val Arg Arg Glu Thr Ser Ser Phe Leu Thr
                165                 170                 175

Glu Thr Val Val Phe Gly Arg Asp Gln Glu Arg Glu Lys Val Val Glu
            180                 185                 190

Leu Leu Leu Asp Ser Gly Ser Gly Asn Ser Ser Phe Ser Val Leu Pro
        195                 200                 205

Leu Val Gly Ile Gly Gly Val Gly Lys Thr Thr Leu Ala Gln Leu Val
    210                 215                 220
```

```
Tyr Asn Asp Asn Arg Val Gly Asn Tyr Phe His Leu Lys Val Trp Val
225                 230                 235                 240

Cys Val Ser Asp Asn Phe Asn Val Lys Arg Leu Thr Lys Glu Ile Ile
            245                 250                 255

Glu Ser Ala Thr Lys Val Glu Gln Ser Asp Lys Leu Asn Leu Asp Thr
        260                 265                 270

Leu Gln Gln Ile Leu Lys Glu Lys Ile Ala Ser Glu Arg Phe Leu Leu
    275                 280                 285

Val Leu Asp Asp Val Trp Ser Glu Asn Arg Asp Asp Trp Glu Arg Leu
    290                 295                 300

Cys Ala Pro Leu Arg Phe Ala Ala Arg Gly Ser Lys Val Ile Val Thr
305                 310                 315                 320

Thr Arg Asp Thr Lys Ile Ala Ser Ile Ile Gly Thr Met Lys Glu Ile
                325                 330                 335

Ser Leu Asp Gly Leu Gln Asp Asp Ala Tyr Trp Glu Leu Phe Lys Lys
            340                 345                 350

Cys Ala Phe Gly Ser Val Asn Pro Gln Glu His Leu Glu Leu Glu Val
            355                 360                 365

Ile Gly Arg Lys Ile Ala Gly Lys Leu Lys Gly Ser Pro Leu Ala Ala
370                 375                 380

Lys Thr Leu Gly Ser Leu Leu Arg Leu Asp Val Ser Gln Glu His Trp
385                 390                 395                 400

Arg Thr Ile Met Glu Ser Glu Val Trp Gln Leu Pro Gln Ala Glu Asn
                405                 410                 415

Glu Ile Leu Pro Val Leu Trp Leu Ser Tyr Gln His Leu Pro Gly His
            420                 425                 430

Leu Arg Gln Cys Phe Ala Phe Cys Ala Val Phe His Lys Asp Tyr Leu
        435                 440                 445

Phe Tyr Lys His Glu Leu Ile Gln Thr Trp Ile Ala Glu Gly Phe Ile
    450                 455                 460

Ala His Gln Gly Asn Lys Arg Met Glu Asp Val Gly Ser Ser Tyr Phe
465                 470                 475                 480

His Glu Leu Val Asn Arg Ser Phe Phe Gln Glu Ser Arg Trp Arg Gly
                485                 490                 495

Arg Tyr Val Met His Asp Leu Ile His Asp Leu Ala Gln Phe Ile Ser
            500                 505                 510

Val Gly Glu Cys His Arg Ile Asp Asp Asp Lys Ser Lys Glu Thr Pro
        515                 520                 525

Ser Thr Thr Arg His Leu Ser Val Ala Leu Thr Glu Gln Met Lys Leu
    530                 535                 540

Val Asp Phe Ser Gly Tyr Asn Lys Leu Arg Thr Leu Met Ile Asn Asn
545                 550                 555                 560

Gln Arg Asn Gln Tyr Pro Tyr Met Thr Lys Val Asn Ser Cys Leu Leu
                565                 570                 575

Pro His Ser Leu Phe Lys Arg Leu Lys Arg Ile His Val Leu Val Leu
            580                 585                 590

Gln Lys Cys Gly Met Lys Glu Leu Pro Asp Ile Ile Gly Asp Leu Ile
        595                 600                 605

Gln Leu Arg Tyr Leu Asp Ile Ser Tyr Asn Ala Cys Ile Gln Arg Leu
    610                 615                 620

Pro Glu Ser Leu Cys Asp Leu Tyr Asn Leu Gln Ala Leu Arg Leu Trp
625                 630                 635                 640
```

-continued

```
Gly Cys Gln Leu Arg Ser Phe Pro Gln Gly Met Ser Lys Leu Ile Asn
                645                 650                 655

Leu Arg Gln Leu Arg Val Glu Asp Glu Ile Ile Ser Lys Ile Tyr Glu
            660                 665                 670

Val Gly Lys Leu Ile Ser Leu Gln Glu Leu Ser Ala Phe Lys Val Leu
        675                 680                 685

Asn Asn His Gly Asn Lys Leu Ala Glu Leu Ser Gly Leu Thr Gln Leu
    690                 695                 700

Arg Ser Thr Leu Arg Ile Thr Asn Leu Glu Asn Val Gly Ser Lys Glu
705                 710                 715                 720

Glu Ala Ser Lys Ala Lys Leu His Arg Lys Gln Tyr Leu Glu Ala Leu
                725                 730                 735

Glu Leu Glu Trp Ala Ala Gly Gln Val Ser Ser Leu Glu His Glu Leu
            740                 745                 750

Leu Val Ser Glu Glu Val Leu Gly Leu Gln Pro His His Phe Leu
        755                 760                 765

Lys Ser Leu Thr Ile Arg Gly Tyr Ser Gly Ala Thr Val Pro Ser Trp
    770                 775                 780

Leu Asp Val Lys Met Leu Pro Asn Leu Gly Thr Leu Lys Leu Glu Asn
785                 790                 795                 800

Cys Thr Arg Leu Glu Gly Leu Ser Tyr Ile Gly Gln Leu Pro His Leu
                805                 810                 815

Lys Val Leu His Met Lys Arg Met Pro Val Val Lys Gln Met Ser His
            820                 825                 830

Glu Leu Cys Gly Cys Thr Lys Ser Lys Leu Phe Pro Arg Leu Glu Glu
        835                 840                 845

Leu Val Leu Glu Asp Met Pro Thr Leu Lys Glu Phe Pro Asn Leu Ala
    850                 855                 860

Gln Leu Pro Cys Leu Lys Ile Ile His Met Lys Asn Met Phe Ala Val
865                 870                 875                 880

Lys His Ile Gly Arg Glu Leu Tyr Gly Asp Ile Glu Ser Asn Cys Phe
                885                 890                 895

Leu Ser Leu Glu Glu Leu Val Leu Gln Asp Met Leu Thr Leu Glu Glu
            900                 905                 910

Leu Pro Asn Leu Gly Gln Leu Pro His Leu Lys Val Ile His Met Lys
        915                 920                 925

Asn Met Ser Ala Leu Lys Leu Ile Gly Arg Glu Leu Cys Asp Ser Arg
    930                 935                 940

Glu Lys Ile Trp Phe Pro Arg Leu Glu Val Leu Val Leu Lys Asn Met
945                 950                 955                 960

Leu Ala Leu Glu Glu Leu Pro Ser Leu Asp Asn Phe Arg Val Ser Arg
                965                 970                 975

Phe Phe Ala Ser Ser Val Glu Val Gly His Gly Leu Phe Ser Ala Thr
            980                 985                 990

Arg Asn Lys Trp Phe Pro Arg Leu Glu Glu Leu Glu Ile Lys Gly Met
        995                 1000                1005

Leu Thr Phe Glu Glu Leu His Ser Leu Glu Lys Leu Pro Cys Leu Lys
    1010                1015                1020

Val Phe Arg Ile Lys Gly Leu Pro Ala Val Lys Lys Ile Gly His Gly
1025                1030                1035                1040

Leu Phe Asp Ser Thr Cys Gln Arg Glu Cys Phe Pro Arg Leu Glu Asp
                1045                1050                1055
```

Leu Val Leu Ser Asp Met Pro Ala Trp Glu Trp Ser Trp Ala Glu
            1060                1065                1070

Arg Glu Glu Leu Phe Ser Cys Leu Cys Arg Leu Lys Ile Glu Gln Cys
        1075                1080                1085

Pro Lys Leu Lys Cys Leu Leu Pro Ile Pro His Ser Leu Ile Lys Leu
    1090                1095                1100

Glu Leu Trp Gln Val Gly Leu Thr Gly Leu Pro Gly Leu Cys Lys Gly
1105                1110                1115                1120

Ile Gly Gly Ser Ser Thr Arg Thr Ala Ser Leu Ser Leu Leu His
            1125                1130                1135

Ile Ile Lys Cys Pro Asn Leu Arg Asn Leu Gly Glu Gly Leu Leu Ser
            1140                1145                1150

Asn His Leu Pro His Ile Asn Ala Ile Arg Ile Trp Glu Cys Ala Glu
            1155                1160                1165

Leu Leu Trp Leu Pro Val Lys Arg Phe Arg Glu Phe Thr Thr Leu Glu
        1170                1175                1180

Asn Leu Ser Ile Arg Asn Cys Pro Lys Leu Met Ser Met Thr Gln Cys
1185                1190                1195                1200

Glu Glu Asn Asp Leu Leu Leu Pro Pro Leu Ile Lys Ala Leu Glu Leu
            1205                1210                1215

Gly Asp Cys Gly Asn Leu Gly Lys Ser Leu Pro Gly Cys Leu His Asn
            1220                1225                1230

Leu Ser Ser Leu Thr Gln Leu Ala Ile Ser Asn Cys Pro Tyr Met Val
            1235                1240                1245

Ser Leu Pro Arg Glu Val Met Leu His Leu Lys Glu Leu Gly Thr Val
        1250                1255                1260

Arg Ile Glu Asn Cys Asp Gly Leu Gly Ser Ile Glu Gly Leu Gln Val
1265                1270                1275                1280

Leu Lys Ser Leu Lys Arg Leu Ala Ile Ile Gly Cys Pro Arg Leu Leu
            1285                1290                1295

Leu Asn Glu Gly Asp Glu Gln Gly Glu Val Leu Ser Leu Leu Glu Leu
            1300                1305                1310

Ser Val Asp Lys Thr Ala Leu Leu Lys Leu Ser Leu Ile Lys Asn Thr
            1315                1320                1325

Leu Pro Phe Ile His Ser Leu Arg Ile Ile Trp Ser Pro Gln Lys Val
            1330                1335                1340

Met Phe Asp Leu Glu Glu Gln Glu Leu Val His Ser Leu Thr Ala Leu
1345                1350                1355                1360

Arg Arg Leu Glu Phe Phe Arg Cys Lys Asn Leu Gln Ser Leu Pro Thr
            1365                1370                1375

Glu Leu His Thr Leu Pro Ser Leu His Ala Leu Val Val Ser Asp Cys
            1380                1385                1390

Pro Gln Ile Gln Ser Leu Pro Glu Lys Gly Leu Pro Thr Leu Leu Thr
            1395                1400                1405

Asp Leu Gly Phe Asp His Cys His Pro Val Leu Thr Ala Gln Leu Glu
            1410                1415                1420

Lys His Leu Ala Glu Met Lys Ser Ser Gly Arg Phe His Pro Val Tyr
1425                1430                1435                1440

Ala

<210> SEQ ID NO 3
<211> LENGTH: 3699
<212> TYPE: DNA
<213> ORGANISM: Musa acuminata

<220> FEATURE:
<221> NAME/KEY: CDS
<222> LOCATION: (1)..(3696)

<400> SEQUENCE: 3

```
atg gct gat gtc aca cca cag gca gcg gcg gtg ttc tcc ctg gtg aat       48
Met Ala Asp Val Thr Pro Gln Ala Ala Ala Val Phe Ser Leu Val Asn
1               5                   10                  15 gaa atc ttt aac cgg tcc atc aat ttg atc gtc gcg gaa ctc cgg ttg       96
Glu Ile Phe Asn Arg Ser Ile Asn Leu Ile Val Ala Glu Leu Arg Leu
            20                  25                  30 cag ttg aat gcg aga gcc gag ctg aac aat ctg cag aga aca cta ttg      144
Gln Leu Asn Ala Arg Ala Glu Leu Asn Asn Leu Gln Arg Thr Leu Leu
        35                  40                  45 agg act cac tct ctg ctc gag gag gca aag gcg agg cgg atg act gac      192
Arg Thr His Ser Leu Leu Glu Glu Ala Lys Ala Arg Arg Met Thr Asp
    50                  55                  60 aag tct ctc gtg ctg tgg ctg atg gag ctc aag gaa tgg gcc tac gac      240
Lys Ser Leu Val Leu Trp Leu Met Glu Leu Lys Glu Trp Ala Tyr Asp
65                  70                  75                  80 gcc gac gac atc ctc gac gag tac gag gcc gca gca atc cga ctg aag      288
Ala Asp Asp Ile Leu Asp Glu Tyr Glu Ala Ala Ala Ile Arg Leu Lys
                85                  90                  95 gta aca cgc tcg acc ttc aaa cgt ctt atc gat cat gtg att ata aat      336
Val Thr Arg Ser Thr Phe Lys Arg Leu Ile Asp His Val Ile Ile Asn
            100                 105                 110 gtt cca tta gcg cac aaa gta gca gac atc agg aaa agg ttg aac ggg      384
Val Pro Leu Ala His Lys Val Ala Asp Ile Arg Lys Arg Leu Asn Gly
        115                 120                 125 gtc act ctt gag agg gag cta aat ctg ggt gcg ctg gaa ggg tcg cag      432
Val Thr Leu Glu Arg Glu Leu Asn Leu Gly Ala Leu Glu Gly Ser Gln
    130                 135                 140 ccg ctt gat tcc acg aaa aga ggt gtg acc act tct ctt ctg act gaa      480
Pro Leu Asp Ser Thr Lys Arg Gly Val Thr Thr Ser Leu Leu Thr Glu
145                 150                 155                 160 tct tgt att gtc ggg cga gct caa gat aag gag aat ttg att cgg ttg      528
Ser Cys Ile Val Gly Arg Ala Gln Asp Lys Glu Asn Leu Ile Arg Leu
                165                 170                 175 ctg ttg gag ccc agc gat ggg gcg gtt cct gtt gtt cct ata gtt gga      576
Leu Leu Glu Pro Ser Asp Gly Ala Val Pro Val Val Pro Ile Val Gly
            180                 185                 190 tta gga ggg gca ggg aag acg act ctg tct cag ctt atc ttt aat gac      624
Leu Gly Gly Ala Gly Lys Thr Thr Leu Ser Gln Leu Ile Phe Asn Asp
        195                 200                 205 aag aga gtg gag gag cat ttc cca ttg aga atg tgg gtg tgt gtg tct      672
Lys Arg Val Glu Glu His Phe Pro Leu Arg Met Trp Val Cys Val Ser
    210                 215                 220 gac gat ttt gat gtg aag aga att act aga gag atc aca gag tac gcc      720
Asp Asp Phe Asp Val Lys Arg Ile Thr Arg Glu Ile Thr Glu Tyr Ala
225                 230                 235                 240 acc aac gga agg ttc atg gat ctc acc aac ttg aat atg ctt caa gtt      768
Thr Asn Gly Arg Phe Met Asp Leu Thr Asn Leu Asn Met Leu Gln Val
                245                 250                 255 aat ctg aaa gag gag ata agg ggg acg aca ttt ttg ctt gtg ctg gat      816
Asn Leu Lys Glu Glu Ile Arg Gly Thr Thr Phe Leu Leu Val Leu Asp
            260                 265                 270 gat gtg tgg aac gaa gac ccc gtg aag tgg gaa agc ctg tta gcc cca      864
Asp Val Trp Asn Glu Asp Pro Val Lys Trp Glu Ser Leu Leu Ala Pro
        275                 280                 285
```

| | | | | | | | | | | | | | | | |
|---|---|---|---|---|---|---|---|---|---|---|---|---|---|---|---|
| tta | gat | gcc | gga | gga | cgg | gga | agc | gtg | gtc | att | gtg | acg | aca | cag | agc | 912 |
| Leu | Asp | Ala | Gly | Gly | Arg | Gly | Ser | Val | Val | Ile | Val | Thr | Thr | Gln | Ser | |
| | 290 | | | | 295 | | | | | 300 | | | | | | | aaa aag gtc gcc gat gtc acc ggc acg atg gag cca tac gtt ctc gag    960
Lys Lys Val Ala Asp Val Thr Gly Thr Met Glu Pro Tyr Val Leu Glu
305             310                 315                 320 gag tta acg gag gat gac agt tgg tca ctc atc gag agt cac tcc ttc   1008
Glu Leu Thr Glu Asp Asp Ser Trp Ser Leu Ile Glu Ser His Ser Phe
            325                 330                 335 agg gag gcg agc tgc tct agt aca aat cct aga atg gaa gag atc ggg   1056
Arg Glu Ala Ser Cys Ser Ser Thr Asn Pro Arg Met Glu Glu Ile Gly
340                 345                 350 agg aag ata gcc aag aag atc agt ggc cta cct tac gga gca aca gca   1104
Arg Lys Ile Ala Lys Lys Ile Ser Gly Leu Pro Tyr Gly Ala Thr Ala
    355                 360                 365 atg ggg aga tat cta aga tct aag cac gga gaa agc agc tgg aga gaa   1152
Met Gly Arg Tyr Leu Arg Ser Lys His Gly Glu Ser Ser Trp Arg Glu
370                 375                 380 gtc ttg gaa act gag act tgg gag atg cca ccg gct gca agt gat gtg   1200
Val Leu Glu Thr Glu Thr Trp Glu Met Pro Pro Ala Ala Ser Asp Val
385                 390                 395                 400 tta tcc gct cta agg aga agt tac gac aat cta ccc cct cag ctg aag   1248
Leu Ser Ala Leu Arg Arg Ser Tyr Asp Asn Leu Pro Pro Gln Leu Lys
                405                 410                 415 ctc tgt ttt gcc ttc tgt gct ctg ttt aca aag ggc tac agg ttt cga   1296
Leu Cys Phe Ala Phe Cys Ala Leu Phe Thr Lys Gly Tyr Arg Phe Arg
            420                 425                 430 aag gat aca ctg atc cac atg tgg ata gct caa aat ttg att caa tca   1344
Lys Asp Thr Leu Ile His Met Trp Ile Ala Gln Asn Leu Ile Gln Ser
        435                 440                 445 aca gag tcg aaa aga tcg gag gac atg gca gaa gaa tgc ttt gat gat   1392
Thr Glu Ser Lys Arg Ser Glu Asp Met Ala Glu Glu Cys Phe Asp Asp
    450                 455                 460 ttg gtg tgc aga ttc ttc ttt cgg tac tcc tgg ggc aac tat gtg atg   1440
Leu Val Cys Arg Phe Phe Phe Arg Tyr Ser Trp Gly Asn Tyr Val Met
465                 470                 475                 480 aat gac tca gtc cat gac ctc gct cga tgg gtt tca ttg gat gaa tat   1488
Asn Asp Ser Val His Asp Leu Ala Arg Trp Val Ser Leu Asp Glu Tyr
                485                 490                 495 ttt cga gca gat gaa gac tca cca ttg cat att tca aag cca att cgt   1536
Phe Arg Ala Asp Glu Asp Ser Pro Leu His Ile Ser Lys Pro Ile Arg
            500                 505                 510 cat ttg tca tgg tgc agt gaa aga ata acc aat gtt ctt gag gat aat   1584
His Leu Ser Trp Cys Ser Glu Arg Ile Thr Asn Val Leu Glu Asp Asn
        515                 520                 525 aac act ggt gga gat gct gtc aat ccg ctc agc agt ttg cgc act ctc   1632
Asn Thr Gly Gly Asp Ala Val Asn Pro Leu Ser Ser Leu Arg Thr Leu
    530                 535                 540 ctt ttc tta ggc caa tct gag ttc cgg tcg tat cat ctt ctt gat aga   1680
Leu Phe Leu Gly Gln Ser Glu Phe Arg Ser Tyr His Leu Leu Asp Arg
545                 550                 555                 560 atg ttc agg atg ttg agc cga atc cgt gtt ttg gat ttc agc aac tgc   1728
Met Phe Arg Met Leu Ser Arg Ile Arg Val Leu Asp Phe Ser Asn Cys
                565                 570                 575 gtc ata aga aat ttg cct tct tcg gtt gga aat ctg aaa cat ctg cgt   1776
Val Ile Arg Asn Leu Pro Ser Ser Val Gly Asn Leu Lys His Leu Arg
            580                 585                 590 tac ctg ggc ctg tct aat acg aga att caa agg ttg ccg gag tct gta   1824
Tyr Leu Gly Leu Ser Asn Thr Arg Ile Gln Arg Leu Pro Glu Ser Val
        595                 600                 605

```
aca cgt ctt tgc ctc ctt cag aca ttg cta cta gag ggc tgt gaa ctg      1872
Thr Arg Leu Cys Leu Leu Gln Thr Leu Leu Leu Glu Gly Cys Glu Leu
    610                 615                 620 tgc agg tta cca aga agc atg agc agg ctc gtc aaa ctg agg cag ctc      1920
Cys Arg Leu Pro Arg Ser Met Ser Arg Leu Val Lys Leu Arg Gln Leu
625                 630                 635                 640 aaa gca aat cca gat gta att gcc gac ata gcc aaa gtc ggg aga ttg      1968
Lys Ala Asn Pro Asp Val Ile Ala Asp Ile Ala Lys Val Gly Arg Leu
                645                 650                 655 atc gaa ctt caa gag ctg aaa gcc tat aat gtt gac aag aaa aaa gga      2016
Ile Glu Leu Gln Glu Leu Lys Ala Tyr Asn Val Asp Lys Lys Lys Gly
            660                 665                 670 cat ggg att gca gag cta agt gca atg aat cag ctt cac ggt gat ctt      2064
His Gly Ile Ala Glu Leu Ser Ala Met Asn Gln Leu His Gly Asp Leu
        675                 680                 685 tcc att aga aac ctt caa aat gta gag aaa acg cga gag tct cgg aag      2112
Ser Ile Arg Asn Leu Gln Asn Val Glu Lys Thr Arg Glu Ser Arg Lys
    690                 695                 700 gcg agg ttg gac gag aaa cag aag ctt aag ctc ttg gat ctg cga tgg      2160
Ala Arg Leu Asp Glu Lys Gln Lys Leu Lys Leu Leu Asp Leu Arg Trp
705                 710                 715                 720 gct gac ggt agg ggt gcc gga gaa tgt gat cgt gac agg aaa gtt ctt      2208
Ala Asp Gly Arg Gly Ala Gly Glu Cys Asp Arg Asp Arg Lys Val Leu
                725                 730                 735 aaa ggc ctc cga cca cat cca aac ctg aga gaa ttg agt atc aaa tac      2256
Lys Gly Leu Arg Pro His Pro Asn Leu Arg Glu Leu Ser Ile Lys Tyr
            740                 745                 750 tac gga ggc act tca tct ccg agt tgg atg acg gat cag tat ctg ccc      2304
Tyr Gly Gly Thr Ser Ser Pro Ser Trp Met Thr Asp Gln Tyr Leu Pro
        755                 760                 765 aac atg gaa acg att cgc ctg cgt agc tgc gca agg ttg acg gaa ctc      2352
Asn Met Glu Thr Ile Arg Leu Arg Ser Cys Ala Arg Leu Thr Glu Leu
    770                 775                 780 cca tgt ctc ggt cag ctg cat atc ctt aga cat ttg cac atc gat ggg      2400
Pro Cys Leu Gly Gln Leu His Ile Leu Arg His Leu His Ile Asp Gly
785                 790                 795                 800 atg tcc caa gtg aga caa att aat ctg caa ttt tat ggc acc gga gaa      2448
Met Ser Gln Val Arg Gln Ile Asn Leu Gln Phe Tyr Gly Thr Gly Glu
                805                 810                 815 gtt tca ggt ttt cca ttg ctg gag ctc ctg aac ata cgt cgc atg ccc      2496
Val Ser Gly Phe Pro Leu Leu Glu Leu Leu Asn Ile Arg Arg Met Pro
            820                 825                 830 agt ctg gag gaa tgg tcg gaa cca cgg aga aac tgt tgc tac ttc cct      2544
Ser Leu Glu Glu Trp Ser Glu Pro Arg Arg Asn Cys Cys Tyr Phe Pro
        835                 840                 845 cgc ctc cat aaa ctg ctg atc gag gat tgt ccc agg ctc agg aat ctg      2592
Arg Leu His Lys Leu Leu Ile Glu Asp Cys Pro Arg Leu Arg Asn Leu
    850                 855                 860 ccc tcc ctc cca cca aca ctg gaa gaa cta agg ata tca aga aca gga      2640
Pro Ser Leu Pro Pro Thr Leu Glu Glu Leu Arg Ile Ser Arg Thr Gly
865                 870                 875                 880 cta gtt gat ctt cca gga ttc cat gga aac ggt gat gtg acg acg aat      2688
Leu Val Asp Leu Pro Gly Phe His Gly Asn Gly Asp Val Thr Thr Asn
                885                 890                 895 gtt tcc ctt tct tct ttg cat gtt tcg gag tgt cga gaa ctg aga tcc      2736
Val Ser Leu Ser Ser Leu His Val Ser Glu Cys Arg Glu Leu Arg Ser
            900                 905                 910 cta agc gaa gga ttg ttg cag cac aac ctc gtc gcc ctc aag aca gcg      2784
Leu Ser Glu Gly Leu Leu Gln His Asn Leu Val Ala Leu Lys Thr Ala
        915                 920                 925
```

-continued

| | | |
|---|---|---|
| gca ttt acc gat tgt gat tct ctt gag ttt ttg ccg gcg gaa gga ttc<br>Ala Phe Thr Asp Cys Asp Ser Leu Glu Phe Leu Pro Ala Glu Gly Phe<br>930              935                 940 | 2832 |
| aga aca gcc att tca ctt gaa tca ttg ata atg act aat tgt cca ctg<br>Arg Thr Ala Ile Ser Leu Glu Ser Leu Ile Met Thr Asn Cys Pro Leu<br>945                 950                 955                 960 | 2880 |
| cct tgc agt ttt ctt ttg cct tcc tct ctc gag cat cta aag ttg cag<br>Pro Cys Ser Phe Leu Leu Pro Ser Ser Leu Glu His Leu Lys Leu Gln<br>                965                 970                 975 | 2928 |
| cca tgc ctc tat cca aac aac aat gag gat tca ctg tca aca tgc ttc<br>Pro Cys Leu Tyr Pro Asn Asn Asn Glu Asp Ser Leu Ser Thr Cys Phe<br>            980                 985                 990 | 2976 |
| gag aac ctc aca tct ctt tcc ttc ttg gac atc aaa gat tgt cca aat<br>Glu Asn Leu Thr Ser Leu Ser Phe Leu Asp Ile Lys Asp Cys Pro Asn<br>        995                 1000                1005 | 3024 |
| ctg tca tca ttt cca ccg ggt cct cta tgt cag cta tca gca ctc<br>Leu Ser Ser Phe Pro Pro Gly Pro Leu Cys Gln Leu Ser Ala Leu<br>1010                1015                1020 | 3069 |
| caa cat ttg tcc ctc gtc aat tgc cag agg cta caa tct att ggc<br>Gln His Leu Ser Leu Val Asn Cys Gln Arg Leu Gln Ser Ile Gly<br>1025                1030                1035 | 3114 |
| ttc cag gca ctc acc tcc ctc gaa agc ttg aca att cag aac tgc<br>Phe Gln Ala Leu Thr Ser Leu Glu Ser Leu Thr Ile Gln Asn Cys<br>1040                1045                1050 | 3159 |
| cct cgc ctc acc atg tca cac agt ttg gtt gag gtg aat aac tct<br>Pro Arg Leu Thr Met Ser His Ser Leu Val Glu Val Asn Asn Ser<br>1055                1060                1065 | 3204 |
| tcc gat aca ggg ctc gcg ttt aat atc act cga tgg atg cgc aga<br>Ser Asp Thr Gly Leu Ala Phe Asn Ile Thr Arg Trp Met Arg Arg<br>1070                1075                1080 | 3249 |
| cga aca ggt gac gac ggc ttg atg ctc aga cac cga gca caa aat<br>Arg Thr Gly Asp Asp Gly Leu Met Leu Arg His Arg Ala Gln Asn<br>1085                1090                1095 | 3294 |
| gat tca ttt ttc ggg gga ctt ctg caa cac ctc acc ttc ctc cag<br>Asp Ser Phe Phe Gly Gly Leu Leu Gln His Leu Thr Phe Leu Gln<br>1100                1105                1110 | 3339 |
| ttt cta aag atc tgc cag tgt cca caa ctc gta acc ttc acc ggc<br>Phe Leu Lys Ile Cys Gln Cys Pro Gln Leu Val Thr Phe Thr Gly<br>1115                1120                1125 | 3384 |
| gaa gag gaa gag aag tgg aga aac ctt act tct ctt caa att ctg<br>Glu Glu Glu Glu Lys Trp Arg Asn Leu Thr Ser Leu Gln Ile Leu<br>1130                1135                1140 | 3429 |
| cac atc gtt gat tgt cca aac ctg gag gta ctg cct gca aac ttg<br>His Ile Val Asp Cys Pro Asn Leu Glu Val Leu Pro Ala Asn Leu<br>1145                1150                1155 | 3474 |
| caa agc ctc tgc tcc ctc agc acc ttg tac atc gtc aga tgc cca<br>Gln Ser Leu Cys Ser Leu Ser Thr Leu Tyr Ile Val Arg Cys Pro<br>1160                1165                1170 | 3519 |
| aga atc cat gcg ttt cct ccc gga ggt gtc agc atg tcc ctg gca<br>Arg Ile His Ala Phe Pro Pro Gly Gly Val Ser Met Ser Leu Ala<br>1175                1180                1185 | 3564 |
| cat ttg gtc atc cat gaa tgc cct cag ctg tgt cag cga tgt gat<br>His Leu Val Ile His Glu Cys Pro Gln Leu Cys Gln Arg Cys Asp<br>1190                1195                1200 | 3609 |
| cca ccg gga ggt gat gat tgg ccc tta ata gct aat gta cca aga<br>Pro Pro Gly Gly Asp Asp Trp Pro Leu Ile Ala Asn Val Pro Arg<br>1205                1210                1215 | 3654 |
| ata tgt ctt gga agg act cat cca tgt cgc tgt agc acc acc tga<br>Ile Cys Leu Gly Arg Thr His Pro Cys Arg Cys Ser Thr Thr<br>1220                1225                1230 | 3699 |

<210> SEQ ID NO 4
<211> LENGTH: 1232
<212> TYPE: PRT
<213> ORGANISM: Musa acuminata

<400> SEQUENCE: 4

```
Met Ala Asp Val Thr Pro Gln Ala Ala Val Phe Ser Leu Val Asn
 1               5                  10                  15

Glu Ile Phe Asn Arg Ser Ile Asn Leu Ile Val Ala Glu Leu Arg Leu
                20                  25                  30

Gln Leu Asn Ala Arg Ala Glu Leu Asn Asn Leu Gln Arg Thr Leu Leu
            35                  40                  45

Arg Thr His Ser Leu Leu Glu Glu Ala Lys Ala Arg Arg Met Thr Asp
        50                  55                  60

Lys Ser Leu Val Leu Trp Leu Met Glu Leu Lys Glu Trp Ala Tyr Asp
 65                  70                  75                  80

Ala Asp Asp Ile Leu Asp Glu Tyr Glu Ala Ala Ile Arg Leu Lys
                85                  90                  95

Val Thr Arg Ser Thr Phe Lys Arg Leu Ile Asp His Val Ile Ile Asn
                100                 105                 110

Val Pro Leu Ala His Lys Val Ala Asp Ile Arg Lys Arg Leu Asn Gly
            115                 120                 125

Val Thr Leu Glu Arg Glu Leu Asn Leu Gly Ala Leu Glu Gly Ser Gln
        130                 135                 140

Pro Leu Asp Ser Thr Lys Arg Gly Val Thr Thr Ser Leu Leu Thr Glu
145                 150                 155                 160

Ser Cys Ile Val Gly Arg Ala Gln Asp Lys Glu Asn Leu Ile Arg Leu
                165                 170                 175

Leu Leu Glu Pro Ser Asp Gly Ala Val Pro Val Val Pro Ile Val Gly
            180                 185                 190

Leu Gly Gly Ala Gly Lys Thr Thr Leu Ser Gln Leu Ile Phe Asn Asp
        195                 200                 205

Lys Arg Val Glu Glu His Phe Pro Leu Arg Met Trp Val Cys Val Ser
    210                 215                 220

Asp Asp Phe Asp Val Lys Arg Ile Thr Arg Glu Ile Thr Glu Tyr Ala
225                 230                 235                 240

Thr Asn Gly Arg Phe Met Asp Leu Thr Asn Leu Asn Met Leu Gln Val
                245                 250                 255

Asn Leu Lys Glu Glu Ile Arg Gly Thr Thr Phe Leu Leu Val Leu Asp
            260                 265                 270

Asp Val Trp Asn Glu Asp Pro Val Lys Trp Glu Ser Leu Leu Ala Pro
        275                 280                 285

Leu Asp Ala Gly Gly Arg Gly Ser Val Val Ile Val Thr Thr Gln Ser
    290                 295                 300

Lys Lys Val Ala Asp Val Thr Gly Thr Met Glu Pro Tyr Val Leu Glu
305                 310                 315                 320

Glu Leu Thr Glu Asp Asp Ser Trp Ser Leu Ile Glu Ser His Ser Phe
                325                 330                 335

Arg Glu Ala Ser Cys Ser Ser Thr Asn Pro Arg Met Glu Glu Ile Gly
            340                 345                 350

Arg Lys Ile Ala Lys Lys Ile Ser Gly Leu Pro Tyr Gly Ala Thr Ala
        355                 360                 365

Met Gly Arg Tyr Leu Arg Ser Lys His Gly Glu Ser Ser Trp Arg Glu
    370                 375                 380
```

-continued

```
Val Leu Glu Thr Glu Thr Trp Glu Met Pro Ala Ala Ser Asp Val
385                 390                 395                 400

Leu Ser Ala Leu Arg Arg Ser Tyr Asp Asn Leu Pro Gln Leu Lys
        405                 410                 415

Leu Cys Phe Ala Phe Cys Ala Leu Phe Thr Lys Gly Tyr Arg Phe Arg
            420                 425                 430

Lys Asp Thr Leu Ile His Met Trp Ile Ala Gln Asn Leu Ile Gln Ser
        435                 440                 445

Thr Glu Ser Lys Arg Ser Glu Asp Met Ala Glu Glu Cys Phe Asp Asp
    450                 455                 460

Leu Val Cys Arg Phe Phe Phe Arg Tyr Ser Trp Gly Asn Tyr Val Met
465                 470                 475                 480

Asn Asp Ser Val His Asp Leu Ala Arg Trp Val Ser Leu Asp Glu Tyr
            485                 490                 495

Phe Arg Ala Asp Glu Asp Ser Pro Leu His Ile Ser Lys Pro Ile Arg
            500                 505                 510

His Leu Ser Trp Cys Ser Glu Arg Ile Thr Asn Val Leu Glu Asp Asn
        515                 520                 525

Asn Thr Gly Gly Asp Ala Val Asn Pro Leu Ser Ser Leu Arg Thr Leu
    530                 535                 540

Leu Phe Leu Gly Gln Ser Glu Phe Arg Ser Tyr His Leu Leu Asp Arg
545                 550                 555                 560

Met Phe Arg Met Leu Ser Arg Ile Arg Val Leu Asp Phe Ser Asn Cys
            565                 570                 575

Val Ile Arg Asn Leu Pro Ser Ser Val Gly Asn Leu Lys His Leu Arg
            580                 585                 590

Tyr Leu Gly Leu Ser Asn Thr Arg Ile Gln Arg Leu Pro Glu Ser Val
        595                 600                 605

Thr Arg Leu Cys Leu Leu Gln Thr Leu Leu Glu Gly Cys Glu Leu
    610                 615                 620

Cys Arg Leu Pro Arg Ser Met Ser Arg Leu Val Lys Leu Arg Gln Leu
625                 630                 635                 640

Lys Ala Asn Pro Asp Val Ile Ala Asp Ile Ala Lys Val Gly Arg Leu
            645                 650                 655

Ile Glu Leu Gln Glu Leu Lys Ala Tyr Asn Val Asp Lys Lys Lys Gly
        660                 665                 670

His Gly Ile Ala Glu Leu Ser Ala Met Asn Gln Leu His Gly Asp Leu
    675                 680                 685

Ser Ile Arg Asn Leu Gln Asn Val Glu Lys Thr Arg Glu Ser Arg Lys
690                 695                 700

Ala Arg Leu Asp Glu Lys Gln Lys Leu Lys Leu Asp Leu Arg Trp
705                 710                 715                 720

Ala Asp Gly Arg Gly Ala Gly Glu Cys Asp Arg Asp Arg Lys Val Leu
            725                 730                 735

Lys Gly Leu Arg Pro His Pro Asn Leu Arg Glu Leu Ser Ile Lys Tyr
            740                 745                 750

Tyr Gly Gly Thr Ser Ser Pro Ser Trp Met Thr Asp Gln Tyr Leu Pro
        755                 760                 765

Asn Met Glu Thr Ile Arg Leu Arg Ser Cys Ala Arg Leu Thr Glu Leu
    770                 775                 780

Pro Cys Leu Gly Gln Leu His Ile Leu Arg His Leu His Ile Asp Gly
785                 790                 795                 800
```

-continued

```
Met Ser Gln Val Arg Gln Ile Asn Leu Gln Phe Tyr Gly Thr Gly Glu
            805                 810                 815

Val Ser Gly Phe Pro Leu Leu Glu Leu Leu Asn Ile Arg Arg Met Pro
            820                 825                 830

Ser Leu Glu Glu Trp Ser Glu Pro Arg Arg Asn Cys Cys Tyr Phe Pro
            835                 840                 845

Arg Leu His Lys Leu Leu Ile Glu Asp Cys Pro Arg Leu Arg Asn Leu
        850                 855                 860

Pro Ser Leu Pro Pro Thr Leu Glu Glu Leu Arg Ile Ser Arg Thr Gly
865                 870                 875                 880

Leu Val Asp Leu Pro Gly Phe His Gly Asn Gly Asp Val Thr Thr Asn
                885                 890                 895

Val Ser Leu Ser Ser Leu His Val Ser Glu Cys Arg Glu Leu Arg Ser
            900                 905                 910

Leu Ser Glu Gly Leu Leu Gln His Asn Leu Val Ala Leu Lys Thr Ala
            915                 920                 925

Ala Phe Thr Asp Cys Asp Ser Leu Glu Phe Leu Pro Ala Glu Gly Phe
        930                 935                 940

Arg Thr Ala Ile Ser Leu Glu Ser Leu Ile Met Thr Asn Cys Pro Leu
945                 950                 955                 960

Pro Cys Ser Phe Leu Leu Pro Ser Ser Leu Glu His Leu Lys Leu Gln
                965                 970                 975

Pro Cys Leu Tyr Pro Asn Asn Asn Glu Asp Ser Leu Ser Thr Cys Phe
            980                 985                 990

Glu Asn Leu Thr Ser Leu Ser Phe Leu Asp Ile Lys Asp Cys Pro Asn
            995                 1000                1005

Leu Ser Ser Phe Pro Pro Gly Pro Leu Cys Gln Leu Ser Ala Leu Gln
        1010                1015                1020

His Leu Ser Leu Val Asn Cys Gln Arg Leu Gln Ser Ile Gly Phe Gln
1025                1030                1035                1040

Ala Leu Thr Ser Leu Glu Ser Leu Thr Ile Gln Asn Cys Pro Arg Leu
            1045                1050                1055

Thr Met Ser His Ser Leu Val Glu Val Asn Asn Ser Ser Asp Thr Gly
            1060                1065                1070

Leu Ala Phe Asn Ile Thr Arg Trp Met Arg Arg Thr Gly Asp Asp
        1075                1080                1085

Gly Leu Met Leu Arg His Arg Ala Gln Asn Asp Ser Phe Phe Gly Gly
    1090                1095                1100

Leu Leu Gln His Leu Thr Phe Leu Gln Phe Leu Lys Ile Cys Gln Cys
1105                1110                1115                1120

Pro Gln Leu Val Thr Phe Thr Gly Glu Glu Glu Glu Lys Trp Arg Asn
            1125                1130                1135

Leu Thr Ser Leu Gln Ile Leu His Ile Val Asp Cys Pro Asn Leu Glu
            1140                1145                1150

Val Leu Pro Ala Asn Leu Gln Ser Leu Cys Ser Leu Ser Thr Leu Tyr
            1155                1160                1165

Ile Val Arg Cys Pro Arg Ile His Ala Phe Pro Pro Gly Gly Val Ser
        1170                1175                1180

Met Ser Leu Ala His Leu Val Ile His Glu Cys Pro Gln Leu Cys Gln
1185                1190                1195                1200
```

```
Arg Cys Asp Pro Pro Gly Gly Asp Asp Trp Pro Leu Ile Ala Asn Val
            1205                1210                1215

Pro Arg Ile Cys Leu Gly Arg Thr His Pro Cys Arg Cys Ser Thr Thr
        1220                1225                1230

<210> SEQ ID NO 5
<211> LENGTH: 87
<212> TYPE: PRT
<213> ORGANISM: Artificial Sequence
<220> FEATURE:
<223> OTHER INFORMATION: Consensus sequence between RGA5 and RGA2 for a
      domain
<220> FEATURE:
<221> NAME/KEY: VARIANT
<222> LOCATION: (2)...(3)
<223> OTHER INFORMATION: Xaa = Tyr, Val, Ile, Leu, Met, Phe, Trp
<220> FEATURE:
<221> NAME/KEY: VARIANT
<222> LOCATION: (4)...(4)
<223> OTHER INFORMATION: Xaa = Asn, His, Gln, Cys, Ser, Thr
<220> FEATURE:
<221> NAME/KEY: VARIANT
<222> LOCATION: (5)...(5)
<223> OTHER INFORMATION: Xaa = any amino acid residue
<220> FEATURE:
<221> NAME/KEY: VARIANT
<222> LOCATION: (6)...(7)
<223> OTHER INFORMATION: Xaa = Tyr, Val, Ile, Leu, Met, Phe, Trp
<220> FEATURE:
<221> NAME/KEY: VARIANT
<222> LOCATION: (8)...(8)
<223> OTHER INFORMATION: Xaa = any amino acid residue
<220> FEATURE:
<221> NAME/KEY: VARIANT
<222> LOCATION: (9)...(9)
<223> OTHER INFORMATION: Xaa = Arg, Lys, His
<220> FEATURE:
<221> NAME/KEY: VARIANT
<222> LOCATION: (10)...(10)
<223> OTHER INFORMATION: Xaa = Gly, Ser, Ala, Thr, Pro
<220> FEATURE:
<221> NAME/KEY: VARIANT
<222> LOCATION: (11)...(11)
<223> OTHER INFORMATION: Xaa = any amino acid residue
<220> FEATURE:
<221> NAME/KEY: VARIANT
<222> LOCATION: (13)...(14)
<223> OTHER INFORMATION: Xaa = any amino acid residue
<220> FEATURE:
<221> NAME/KEY: VARIANT
<222> LOCATION: (15)...(15)
<223> OTHER INFORMATION: Xaa = Tyr, Val, Ile, Leu, Met, Phe, Trp
<220> FEATURE:
<221> NAME/KEY: VARIANT
<222> LOCATION: (16)...(17)
<223> OTHER INFORMATION: Xaa = any amino acid residue
<220> FEATURE:
<221> NAME/KEY: VARIANT
<222> LOCATION: (19)...(24)
<223> OTHER INFORMATION: Xaa = any amino acid residue
<220> FEATURE:
<221> NAME/KEY: VARIANT
<222> LOCATION: (25)...(25)
<223> OTHER INFORMATION: Xaa = Arg, Lys, His
<220> FEATURE:
<221> NAME/KEY: VARIANT
<222> LOCATION: (26)...(26)
<223> OTHER INFORMATION: Xaa = any amino acid residue
<220> FEATURE:
<221> NAME/KEY: VARIANT
<222> LOCATION: (27)...(27)
<223> OTHER INFORMATION: Xaa = Asp, Glu
<220> FEATURE:
<221> NAME/KEY: VARIANT
<222> LOCATION: (29)...(30)
<223> OTHER INFORMATION: Xaa = any amino acid residue
```

```
<220> FEATURE:
<221> NAME/KEY: VARIANT
<222> LOCATION: (32)...(33)
<223> OTHER INFORMATION: Xaa = any amino acid residue
<220> FEATURE:
<221> NAME/KEY: VARIANT
<222> LOCATION: (34)...(34)
<223> OTHER INFORMATION: Xaa = Gly, Ser, Ala, Thr, Pro
<220> FEATURE:
<221> NAME/KEY: VARIANT
<222> LOCATION: (38)...(38)
<223> OTHER INFORMATION: Xaa = any amino acid residue
<220> FEATURE:
<221> NAME/KEY: VARIANT
<222> LOCATION: (40)...(40)
<223> OTHER INFORMATION: Xaa = Gly, Ser, Ala, Thr, Pro
<220> FEATURE:
<221> NAME/KEY: VARIANT
<222> LOCATION: (41)...(41)
<223> OTHER INFORMATION: Xaa = Tyr, Val, Ile, Leu, Met, Phe, Trp
<220> FEATURE:
<221> NAME/KEY: VARIANT
<222> LOCATION: (43)...(43)
<223> OTHER INFORMATION: Xaa = Asp, Glu
<220> FEATURE:
<221> NAME/KEY: VARIANT
<222> LOCATION: (44)...(44)
<223> OTHER INFORMATION: Xaa = Asp, Glu, Arg, Lys, His
<220> FEATURE:
<221> NAME/KEY: VARIANT
<222> LOCATION: (46)...(46)
<223> OTHER INFORMATION: Xaa = Asp, Glu, Arg, Lys, His
<220> FEATURE:
<221> NAME/KEY: VARIANT
<222> LOCATION: (47)...(47)
<223> OTHER INFORMATION: Xaa = Gly, Ser, Ala, Thr, Pro
<220> FEATURE:
<221> NAME/KEY: VARIANT
<222> LOCATION: (49)...(55)
<223> OTHER INFORMATION: Xaa = any amino acid residue
<220> FEATURE:
<221> NAME/KEY: VARIANT
<222> LOCATION: (59)...(59)
<223> OTHER INFORMATION: Xaa = any amino acid residue
<220> FEATURE:
<221> NAME/KEY: VARIANT
<222> LOCATION: (60)...(61)
<223> OTHER INFORMATION: Xaa = Tyr, Val, Ile, Leu, Met, Phe, Trp
<220> FEATURE:
<221> NAME/KEY: VARIANT
<222> LOCATION: (62)...(63)
<223> OTHER INFORMATION: Xaa = any amino acid residue
<220> FEATURE:
<221> NAME/KEY: VARIANT
<222> LOCATION: (66)...(66)
<223> OTHER INFORMATION: Xaa = Asp, Glu
<220> FEATURE:
<221> NAME/KEY: VARIANT
<222> LOCATION: (67)...(67)
<223> OTHER INFORMATION: Xaa = any amino acid residue
<220> FEATURE:
<221> NAME/KEY: VARIANT
<222> LOCATION: (72)...(72)
<223> OTHER INFORMATION: Xaa = Asp, Glu
<220> FEATURE:
<221> NAME/KEY: VARIANT
<222> LOCATION: (74)...(74)
<223> OTHER INFORMATION: Xaa = Tyr, Val, Ile, Leu, Met, Phe, Trp
<220> FEATURE:
<221> NAME/KEY: VARIANT
<222> LOCATION: (76)...(76)
<223> OTHER INFORMATION: Xaa = Asp, Glu
<220> FEATURE:
<221> NAME/KEY: VARIANT
<222> LOCATION: (78)...(78)
<223> OTHER INFORMATION: Xaa = Tyr, Val, Ile, Leu, Met, Phe, Trp
```

```
<220> FEATURE:
<221> NAME/KEY: VARIANT
<222> LOCATION: (80)...(81)
<223> OTHER INFORMATION: Xaa = any amino acid residue
<220> FEATURE:
<221> NAME/KEY: VARIANT
<222> LOCATION: (83)...(83)
<223> OTHER INFORMATION: Xaa = any amino acid residue
<220> FEATURE:
<221> NAME/KEY: VARIANT
<222> LOCATION: (84)...(84)
<223> OTHER INFORMATION: Xaa = Arg, Lys, His
<220> FEATURE:
<221> NAME/KEY: VARIANT
<222> LOCATION: (85)...(85)
<223> OTHER INFORMATION: Xaa = any amino acid residue

<400> SEQUENCE: 5

Ser Xaa Xaa Xaa Xaa Xaa Xaa Xaa Xaa Asn Xaa Xaa Xaa Xaa
  1               5                  10                  15

Xaa Leu Xaa Xaa Xaa Xaa Xaa Xaa Xaa Xaa Leu Xaa Xaa Leu Xaa
         20                  25                  30

Xaa Xaa Leu Leu Arg Xaa His Xaa Xaa Leu Xaa Xaa Ala Xaa Arg
     35                  40                  45

Xaa Xaa Xaa Xaa Xaa Xaa Xaa Ser Leu Val Xaa Xaa Xaa Xaa Leu
 50                  55                  60

Lys Xaa Xaa Ala Tyr Asp Ala Xaa Asp Xaa Leu Xaa Glu Xaa Glu Xaa
 65                  70                  75                  80

Xaa Ala Xaa Xaa Xaa Lys Val
             85

<210> SEQ ID NO 6
<211> LENGTH: 298
<212> TYPE: PRT
<213> ORGANISM: Artificial Sequence
<220> FEATURE:
<223> OTHER INFORMATION: Consensus sequence between RGA5 and RGA2 for a
      domain
<220> FEATURE:
<221> NAME/KEY: VARIANT
<222> LOCATION: (2)...(3)
<223> OTHER INFORMATION: Xaa = any amino acid residue
<220> FEATURE:
<221> NAME/KEY: VARIANT
<222> LOCATION: (5)...(5)
<223> OTHER INFORMATION: Xaa = Gly, Ser, Ala, Thr, Pro
<220> FEATURE:
<221> NAME/KEY: VARIANT
<222> LOCATION: (7)...(7)
<223> OTHER INFORMATION: Xaa = Tyr, Val, Ile, Leu, Met, Phe, Trp
<220> FEATURE:
<221> NAME/KEY: VARIANT
<222> LOCATION: (11)...(11)
<223> OTHER INFORMATION: Xaa = Gly, Ser, Ala, Thr, Pro
<220> FEATURE:
<221> NAME/KEY: VARIANT
<222> LOCATION: (12)...(12)
<223> OTHER INFORMATION: Xaa = any amino acid residue
<220> FEATURE:
<221> NAME/KEY: VARIANT
<222> LOCATION: (13)...(14)
<223> OTHER INFORMATION: Xaa = Tyr, Val, Ile, Leu, Met, Phe, Trp
<220> FEATURE:
<221> NAME/KEY: VARIANT
<222> LOCATION: (17)...(17)
<223> OTHER INFORMATION: Xaa = any amino acid residue
<220> FEATURE:
<221> NAME/KEY: VARIANT
<222> LOCATION: (19)...(19)
<223> OTHER INFORMATION: Xaa = Asp, Glu
```

-continued

```
<220> FEATURE:
<221> NAME/KEY: VARIANT
<222> LOCATION: (20)...(20)
<223> OTHER INFORMATION: Xaa = Arg, Lys, His
<220> FEATURE:
<221> NAME/KEY: VARIANT
<222> LOCATION: (22)...(22)
<223> OTHER INFORMATION: Xaa = any amino acid residue
<220> FEATURE:
<221> NAME/KEY: VARIANT
<222> LOCATION: (23)...(24)
<223> OTHER INFORMATION: Xaa = Tyr, Val, Ile, Leu, Met, Phe, Trp
<220> FEATURE:
<221> NAME/KEY: VARIANT
<222> LOCATION: (25)...(25)
<223> OTHER INFORMATION: Xaa = Asp, Glu, Arg, Lys, His
<220> FEATURE:
<221> NAME/KEY: VARIANT
<222> LOCATION: (29)...(29)
<223> OTHER INFORMATION: Xaa = Asp, Glu
<220> FEATURE:
<221> NAME/KEY: VARIANT
<222> LOCATION: (30)...(31)
<223> OTHER INFORMATION: Xaa = Gly, Ser, Ala, Thr, Pro
<220> FEATURE:
<221> NAME/KEY: VARIANT
<222> LOCATION: (32)...(32)
<223> OTHER INFORMATION: Xaa = any amino acid residue
<220> FEATURE:
<221> NAME/KEY: VARIANT
<222> LOCATION: (34)...(35)
<223> OTHER INFORMATION: Xaa = any amino acid residue
<220> FEATURE:
<221> NAME/KEY: VARIANT
<222> LOCATION: (36)...(36)
<223> OTHER INFORMATION: Xaa = Gly, Ser, Ala, Thr, Pro
<220> FEATURE:
<221> NAME/KEY: VARIANT
<222> LOCATION: (38)...(38)
<223> OTHER INFORMATION: Xaa = Gly, Ser, Ala, Thr, Pro
<220> FEATURE:
<221> NAME/KEY: VARIANT
<222> LOCATION: (40)...(40)
<223> OTHER INFORMATION: Xaa = Tyr, Val, Ile, Leu, Met, Phe, Trp
<220> FEATURE:
<221> NAME/KEY: VARIANT
<222> LOCATION: (42)...(42)
<223> OTHER INFORMATION: Xaa = Tyr, Val, Ile, Leu, Met, Phe, Trp
<220> FEATURE:
<221> NAME/KEY: VARIANT
<222> LOCATION: (45)...(45)
<223> OTHER INFORMATION: Xaa = Tyr, Val, Ile, Leu, Met, Phe, Trp
<220> FEATURE:
<221> NAME/KEY: VARIANT
<222> LOCATION: (48)...(48)
<223> OTHER INFORMATION: Xaa = any amino acid residue
<220> FEATURE:
<221> NAME/KEY: VARIANT
<222> LOCATION: (54)...(54)
<223> OTHER INFORMATION: Xaa = Gly, Ser, Ala, Thr, Pro
<220> FEATURE:
<221> NAME/KEY: VARIANT
<222> LOCATION: (57)...(58)
<223> OTHER INFORMATION: Xaa = Tyr, Val, Ile, Leu, Met, Phe, Trp
<220> FEATURE:
<221> NAME/KEY: VARIANT
<222> LOCATION: (61)...(61)
<223> OTHER INFORMATION: Xaa = any amino acid residue
<220> FEATURE:
<221> NAME/KEY: VARIANT
<222> LOCATION: (64)...(66)
<223> OTHER INFORMATION: Xaa = any amino acid residue
<220> FEATURE:
<221> NAME/KEY: VARIANT
<222> LOCATION: (68)...(68)
<223> OTHER INFORMATION: Xaa = any amino acid residue
```

-continued

```
<220> FEATURE:
<221> NAME/KEY: VARIANT
<222> LOCATION: (70)...(70)
<223> OTHER INFORMATION: Xaa = Arg, Lys, His
<220> FEATURE:
<221> NAME/KEY: VARIANT
<222> LOCATION: (71)...(71)
<223> OTHER INFORMATION: Xaa = Tyr, Val, Ile, Leu, Met, Phe, Trp
<220> FEATURE:
<221> NAME/KEY: VARIANT
<222> LOCATION: (78)...(78)
<223> OTHER INFORMATION: Xaa = any amino acid residue
<220> FEATURE:
<221> NAME/KEY: VARIANT
<222> LOCATION: (80)...(80)
<223> OTHER INFORMATION: Xaa = any amino acid residue
<220> FEATURE:
<221> NAME/KEY: VARIANT
<222> LOCATION: (84)...(84)
<223> OTHER INFORMATION: Xaa = Tyr, Val, Ile, Leu, Met, Phe, Trp
<220> FEATURE:
<221> NAME/KEY: VARIANT
<222> LOCATION: (86)...(86)
<223> OTHER INFORMATION: Xaa = Arg, Lys, His
<220> FEATURE:
<221> NAME/KEY: VARIANT
<222> LOCATION: (89)...(89)
<223> OTHER INFORMATION: Xaa = any amino acid residue
<220> FEATURE:
<221> NAME/KEY: VARIANT
<222> LOCATION: (91)...(91)
<223> OTHER INFORMATION: Xaa = any amino acid residue
<220> FEATURE:
<221> NAME/KEY: VARIANT
<222> LOCATION: (94)...(95)
<223> OTHER INFORMATION: Xaa = any amino acid residue
<220> FEATURE:
<221> NAME/KEY: VARIANT
<222> LOCATION: (96)...(96)
<223> OTHER INFORMATION: Xaa = Asp, Glu, Arg, Lys, His
<220> FEATURE:
<221> NAME/KEY: VARIANT
<222> LOCATION: (97)...(98)
<223> OTHER INFORMATION: Xaa = any amino acid residue
<220> FEATURE:
<221> NAME/KEY: VARIANT
<222> LOCATION: (100)...(101)
<223> OTHER INFORMATION: Xaa = any amino acid residue
<220> FEATURE:
<221> NAME/KEY: VARIANT
<222> LOCATION: (104)...(105)
<223> OTHER INFORMATION: Xaa = any amino acid residue
<220> FEATURE:
<221> NAME/KEY: VARIANT
<222> LOCATION: (108)...(109)
<223> OTHER INFORMATION: Xaa = any amino acid residue
<220> FEATURE:
<221> NAME/KEY: VARIANT
<222> LOCATION: (113)...(113)
<223> OTHER INFORMATION: Xaa = Asp, Glu, Arg, Lys, His
<220> FEATURE:
<221> NAME/KEY: VARIANT
<222> LOCATION: (115)...(115)
<223> OTHER INFORMATION: Xaa = any amino acid residue
<220> FEATURE:
<221> NAME/KEY: VARIANT
<222> LOCATION: (116)...(116)
<223> OTHER INFORMATION: Xaa = Gly, Ser, Ala, Thr, Pro
<220> FEATURE:
<221> NAME/KEY: VARIANT
<222> LOCATION: (117)...(118)
<223> OTHER INFORMATION: Xaa = any amino acid residue
<220> FEATURE:
<221> NAME/KEY: VARIANT
<222> LOCATION: (128)...(128)
<223> OTHER INFORMATION: Xaa = any amino acid residue
```

-continued

```
<220> FEATURE:
<221> NAME/KEY: VARIANT
<222> LOCATION: (130)...(132)
<223> OTHER INFORMATION: Xaa = any amino acid residue
<220> FEATURE:
<221> NAME/KEY: VARIANT
<222> LOCATION: (133)...(133)
<223> OTHER INFORMATION: Xaa = Asp, Glu, Arg, Lys, His
<220> FEATURE:
<221> NAME/KEY: VARIANT
<222> LOCATION: (136)...(136)
<223> OTHER INFORMATION: Xaa = any amino acid residue
<220> FEATURE:
<221> NAME/KEY: VARIANT
<222> LOCATION: (138)...(138)
<223> OTHER INFORMATION: Xaa = any amino acid residue
<220> FEATURE:
<221> NAME/KEY: VARIANT
<222> LOCATION: (142)...(142)
<223> OTHER INFORMATION: Xaa = Asp, Glu, Arg, Lys, His
<220> FEATURE:
<221> NAME/KEY: VARIANT
<222> LOCATION: (143)...(143)
<223> OTHER INFORMATION: Xaa = any amino acid residue
<220> FEATURE:
<221> NAME/KEY: VARIANT
<222> LOCATION: (144)...(145)
<223> OTHER INFORMATION: Xaa = Gly, Ser, Ala, Thr, Pro
<220> FEATURE:
<221> NAME/KEY: VARIANT
<222> LOCATION: (149)...(149)
<223> OTHER INFORMATION: Xaa = any amino acid residue
<220> FEATURE:
<221> NAME/KEY: VARIANT
<222> LOCATION: (155)...(157)
<223> OTHER INFORMATION: Xaa = any amino acid residue
<220> FEATURE:
<221> NAME/KEY: VARIANT
<222> LOCATION: (159)...(159)
<223> OTHER INFORMATION: Xaa = Tyr, Val, Ile, Leu, Met, Phe, Trp
<220> FEATURE:
<221> NAME/KEY: VARIANT
<222> LOCATION: (161)...(161)
<223> OTHER INFORMATION: Xaa = any amino acid residue
<220> FEATURE:
<221> NAME/KEY: VARIANT
<222> LOCATION: (162)...(162)
<223> OTHER INFORMATION: Xaa = Tyr, Val, Ile, Leu, Met, Phe, Trp
<220> FEATURE:
<221> NAME/KEY: VARIANT
<222> LOCATION: (163)...(163)
<223> OTHER INFORMATION: Xaa = any amino acid residue
<220> FEATURE:
<221> NAME/KEY: VARIANT
<222> LOCATION: (167)...(167)
<223> OTHER INFORMATION: Xaa = Asp, Glu, Arg, Lys, His
<220> FEATURE:
<221> NAME/KEY: VARIANT
<222> LOCATION: (168)...(168)
<223> OTHER INFORMATION: Xaa = any amino acid residue
<220> FEATURE:
<221> NAME/KEY: VARIANT
<222> LOCATION: (169)...(169)
<223> OTHER INFORMATION: Xaa = Tyr, Val, Ile, Leu, Met, Phe, Trp
<220> FEATURE:
<221> NAME/KEY: VARIANT
<222> LOCATION: (170)...(170)
<223> OTHER INFORMATION: Xaa = any amino acid residue
<220> FEATURE:
<221> NAME/KEY: VARIANT
<222> LOCATION: (172)...(172)
<223> OTHER INFORMATION: Xaa = Asp, Glu
<220> FEATURE:
<221> NAME/KEY: VARIANT
<222> LOCATION: (173)...(173)
<223> OTHER INFORMATION: Xaa = any amino acid residue
```

```
<220> FEATURE:
<221> NAME/KEY: VARIANT
<222> LOCATION: (175)...(175)
<223> OTHER INFORMATION: Xaa = any amino acid residue
<220> FEATURE:
<221> NAME/KEY: VARIANT
<222> LOCATION: (176)...(176)
<223> OTHER INFORMATION: Xaa = Asp, Glu
<220> FEATURE:
<221> NAME/KEY: VARIANT
<222> LOCATION: (178)...(179)
<223> OTHER INFORMATION: Xaa = any amino acid residue
<220> FEATURE:
<221> NAME/KEY: VARIANT
<222> LOCATION: (181)...(181)
<223> OTHER INFORMATION: Xaa = any amino acid residue
<220> FEATURE:
<221> NAME/KEY: VARIANT
<222> LOCATION: (183)...(183)
<223> OTHER INFORMATION: Xaa = Tyr, Val, Ile, Leu, Met, Phe, Trp
<220> FEATURE:
<221> NAME/KEY: VARIANT
<222> LOCATION: (184)...(184)
<223> OTHER INFORMATION: Xaa = Asp, Glu, Arg, Lys, His
<220> FEATURE:
<221> NAME/KEY: VARIANT
<222> LOCATION: (185)...(186)
<223> OTHER INFORMATION: Xaa = any amino acid residue
<220> FEATURE:
<221> NAME/KEY: VARIANT
<222> LOCATION: (187)...(187)
<223> OTHER INFORMATION: Xaa = Gly, Ser, Ala, Thr, Pro
<220> FEATURE:
<221> NAME/KEY: VARIANT
<222> LOCATION: (189)...(193)
<223> OTHER INFORMATION: Xaa = any amino acid residue
<220> FEATURE:
<221> NAME/KEY: VARIANT
<222> LOCATION: (194)...(194)
<223> OTHER INFORMATION: Xaa = Gly, Ser, Ala, Thr, Pro
<220> FEATURE:
<221> NAME/KEY: VARIANT
<222> LOCATION: (195)...(198)
<223> OTHER INFORMATION: Xaa = any amino acid residue
<220> FEATURE:
<221> NAME/KEY: VARIANT
<222> LOCATION: (199)...(199)
<223> OTHER INFORMATION: Xaa = Asp, Glu, Arg, Lys, His
<220> FEATURE:
<221> NAME/KEY: VARIANT
<222> LOCATION: (200)...(200)
<223> OTHER INFORMATION: Xaa = Tyr, Val, Ile, Leu, Met, Phe, Trp
<220> FEATURE:
<221> NAME/KEY: VARIANT
<222> LOCATION: (202)...(202)
<223> OTHER INFORMATION: Xaa = any amino acid residue
<220> FEATURE:
<221> NAME/KEY: VARIANT
<222> LOCATION: (209)...(209)
<223> OTHER INFORMATION: Xaa = any amino acid residue
<220> FEATURE:
<221> NAME/KEY: VARIANT
<222> LOCATION: (211)...(211)
<223> OTHER INFORMATION: Xaa = Tyr, Val, Ile, Leu, Met, Phe, Trp
<220> FEATURE:
<221> NAME/KEY: VARIANT
<222> LOCATION: (212)...(212)
<223> OTHER INFORMATION: Xaa = any amino acid residue
<220> FEATURE:
<221> NAME/KEY: VARIANT
<222> LOCATION: (214)...(214)
<223> OTHER INFORMATION: Xaa = any amino acid residue
<220> FEATURE:
<221> NAME/KEY: VARIANT
<222> LOCATION: (216)...(216)
<223> OTHER INFORMATION: Xaa = Tyr, Val, Ile, Leu, Met, Phe, Trp
```

```
<220> FEATURE:
<221> NAME/KEY: VARIANT
<222> LOCATION: (217)...(217)
<223> OTHER INFORMATION: Xaa = Gly, Ser, Ala, Thr, Pro
<220> FEATURE:
<221> NAME/KEY: VARIANT
<222> LOCATION: (219)...(219)
<223> OTHER INFORMATION: Xaa = any amino acid residue
<220> FEATURE:
<221> NAME/KEY: VARIANT
<222> LOCATION: (220)...(220)
<223> OTHER INFORMATION: Xaa = Gly, Ser, Ala, Thr, Pro
<220> FEATURE:
<221> NAME/KEY: VARIANT
<222> LOCATION: (221)...(221)
<223> OTHER INFORMATION: Xaa = Tyr, Val, Ile, Leu, Met, Phe, Trp
<220> FEATURE:
<221> NAME/KEY: VARIANT
<222> LOCATION: (223)...(223)
<223> OTHER INFORMATION: Xaa = any amino acid residue
<220> FEATURE:
<221> NAME/KEY: VARIANT
<222> LOCATION: (224)...(224)
<223> OTHER INFORMATION: Xaa = Tyr, Val, Ile, Leu, Met, Phe, Trp
<220> FEATURE:
<221> NAME/KEY: VARIANT
<222> LOCATION: (227)...(227)
<223> OTHER INFORMATION: Xaa = any amino acid residue
<220> FEATURE:
<221> NAME/KEY: VARIANT
<222> LOCATION: (228)...(228)
<223> OTHER INFORMATION: Xaa = Asp, Glu, Arg, Lys, His
<220> FEATURE:
<221> NAME/KEY: VARIANT
<222> LOCATION: (229)...(229)
<223> OTHER INFORMATION: Xaa = any amino acid residue
<220> FEATURE:
<221> NAME/KEY: VARIANT
<222> LOCATION: (230)...(230)
<223> OTHER INFORMATION: Xaa = Gly, Ser, Ala, Thr, Pro
<220> FEATURE:
<221> NAME/KEY: VARIANT
<222> LOCATION: (231)...(233)
<223> OTHER INFORMATION: Xaa = any amino acid residue
<220> FEATURE:
<221> NAME/KEY: VARIANT
<222> LOCATION: (236)...(236)
<223> OTHER INFORMATION: Xaa = any amino acid residue
<220> FEATURE:
<221> NAME/KEY: VARIANT
<222> LOCATION: (237)...(238)
<223> OTHER INFORMATION: Xaa = Tyr, Val, Ile, Leu, Met, Phe, Trp
<220> FEATURE:
<221> NAME/KEY: VARIANT
<222> LOCATION: (240)...(240)
<223> OTHER INFORMATION: Xaa = Gly, Ser, Ala, Thr, Pro
<220> FEATURE:
<221> NAME/KEY: VARIANT
<222> LOCATION: (242)...(242)
<223> OTHER INFORMATION: Xaa = any amino acid residue
<220> FEATURE:
<221> NAME/KEY: VARIANT
<222> LOCATION: (244)...(244)
<223> OTHER INFORMATION: Xaa = any amino acid residue
<220> FEATURE:
<221> NAME/KEY: VARIANT
<222> LOCATION: (245)...(245)
<223> OTHER INFORMATION: Xaa = Tyr, Val, Ile, Leu, Met, Phe, Trp
<220> FEATURE:
<221> NAME/KEY: VARIANT
<222> LOCATION: (247)...(247)
<223> OTHER INFORMATION: Xaa = any amino acid residue
<220> FEATURE:
<221> NAME/KEY: VARIANT
<222> LOCATION: (249)...(250)
<223> OTHER INFORMATION: Xaa = any amino acid residue
```

```
<220> FEATURE:
<221> NAME/KEY: VARIANT
<222> LOCATION: (251)...(251)
<223> OTHER INFORMATION: Xaa = Asp, Glu
<220> FEATURE:
<221> NAME/KEY: VARIANT
<222> LOCATION: (252)...(252)
<223> OTHER INFORMATION: Xaa = Tyr, Val, Ile, Leu, Met, Phe, Trp
<220> FEATURE:
<221> NAME/KEY: VARIANT
<222> LOCATION: (254)...(254)
<223> OTHER INFORMATION: Xaa = Gly, Ser, Ala, Thr, Pro
<220> FEATURE:
<221> NAME/KEY: VARIANT
<222> LOCATION: (255)...(255)
<223> OTHER INFORMATION: Xaa = any amino acid residue
<220> FEATURE:
<221> NAME/KEY: VARIANT
<222> LOCATION: (257)...(258)
<223> OTHER INFORMATION: Xaa = any amino acid residue
<220> FEATURE:
<221> NAME/KEY: VARIANT
<222> LOCATION: (261)...(262)
<223> OTHER INFORMATION: Xaa = any amino acid residue
<220> FEATURE:
<221> NAME/KEY: VARIANT
<222> LOCATION: (265)...(268)
<223> OTHER INFORMATION: Xaa = Gly, Ser, Ala, Thr, Pro
<220> FEATURE:
<221> NAME/KEY: VARIANT
<222> LOCATION: (269)...(269)
<223> OTHER INFORMATION: Xaa = any amino acid residue
<220> FEATURE:
<221> NAME/KEY: VARIANT
<222> LOCATION: (276)...(276)
<223> OTHER INFORMATION: Xaa = Tyr, Val, Ile, Leu, Met, Phe, Trp
<220> FEATURE:
<221> NAME/KEY: VARIANT
<222> LOCATION: (278)...(278)
<223> OTHER INFORMATION: Xaa = any amino acid residue
<220> FEATURE:
<221> NAME/KEY: VARIANT
<222> LOCATION: (280)...(280)
<223> OTHER INFORMATION: Xaa = any amino acid residue
<220> FEATURE:
<221> NAME/KEY: VARIANT
<222> LOCATION: (282)...(282)
<223> OTHER INFORMATION: Xaa = any amino acid residue
<220> FEATURE:
<221> NAME/KEY: VARIANT
<222> LOCATION: (284)...(284)
<223> OTHER INFORMATION: Xaa = any amino acid residue
<220> FEATURE:
<221> NAME/KEY: VARIANT
<222> LOCATION: (286)...(286)
<223> OTHER INFORMATION: Xaa = Asp, Glu, Arg, Lys, His
<220> FEATURE:
<221> NAME/KEY: VARIANT
<222> LOCATION: (287)...(287)
<223> OTHER INFORMATION: Xaa = any amino acid residue
<220> FEATURE:
<221> NAME/KEY: VARIANT
<222> LOCATION: (290)...(291)
<223> OTHER INFORMATION: Xaa = any amino acid residue
<220> FEATURE:
<221> NAME/KEY: VARIANT
<222> LOCATION: (295)...(296)
<223> OTHER INFORMATION: Xaa = any amino acid residue
<220> FEATURE:
<221> NAME/KEY: VARIANT
<222> LOCATION: (297)...(297)
<223> OTHER INFORMATION: Xaa = Tyr, Val, Ile, Leu, Met, Phe, Trp
```

<400> SEQUENCE: 6

```
Arg Xaa Xaa Thr Xaa Ser Xaa Leu Thr Glu Xaa Xaa Xaa Xaa Gly Arg
 1               5                  10                  15

Xaa Gln Xaa Xaa Glu Xaa Xaa Xaa Xaa Leu Leu Leu Xaa Xaa Xaa Xaa
            20                  25                  30

Gly Xaa Xaa Xaa Phe Xaa Val Xaa Pro Xaa Val Gly Xaa Gly Gly Xaa
        35                  40                  45

Gly Lys Thr Thr Leu Xaa Gln Leu Xaa Xaa Asn Asp Xaa Arg Val Xaa
    50                  55                  60

Xaa Xaa Phe Xaa Leu Xaa Xaa Trp Val Cys Val Ser Asp Xaa Phe Xaa
65                  70                  75                  80

Val Lys Arg Xaa Thr Xaa Glu Ile Xaa Glu Xaa Ala Thr Xaa Xaa Xaa
                85                  90                  95

Xaa Xaa Asp Xaa Xaa Asn Leu Xaa Xaa Leu Gln Xaa Xaa Leu Lys Glu
            100                 105                 110

Xaa Ile Xaa Xaa Xaa Xaa Phe Leu Leu Val Leu Asp Asp Val Trp Xaa
        115                 120                 125

Glu Xaa Xaa Xaa Xaa Trp Glu Xaa Leu Xaa Ala Pro Leu Xaa Xaa Xaa
    130                 135                 140

Xaa Arg Gly Ser Xaa Val Ile Val Thr Thr Xaa Xaa Xaa Lys Xaa Ala
145                 150                 155                 160

Xaa Xaa Xaa Gly Thr Met Xaa Xaa Xaa Xaa Leu Xaa Xaa Leu Xaa Xaa
                165                 170                 175

Asp Xaa Xaa Trp Xaa Leu Xaa Xaa Xaa Xaa Xaa Phe Xaa Xaa Xaa Xaa
            180                 185                 190

Xaa Xaa Xaa Xaa Xaa Xaa Xaa Xaa Glu Xaa Ile Gly Arg Lys Ile Ala
        195                 200                 205

Xaa Lys Xaa Xaa Gly Xaa Pro Xaa Xaa Ala Xaa Xaa Xaa Gly Xaa Xaa
    210                 215                 220

Leu Arg Xaa Xaa Xaa Xaa Xaa Xaa Xaa Trp Arg Xaa Xaa Xaa Glu Xaa
225                 230                 235                 240

Glu Xaa Trp Xaa Xaa Pro Xaa Ala Xaa Xaa Xaa Xaa Leu Xaa Xaa Leu
                245                 250                 255

Xaa Xaa Ser Tyr Xaa Xaa Leu Pro Xaa Xaa Leu Xaa Xaa Cys Phe Ala
            260                 265                 270

Phe Cys Ala Xaa Phe Xaa Lys Xaa Tyr Xaa Phe Xaa Lys Xaa Xaa Leu
        275                 280                 285

Ile Xaa Xaa Trp Ile Ala Xaa Xaa Xaa Ile
    290                 295
```

<210> SEQ ID NO 7
<211> LENGTH: 285
<212> TYPE: PRT
<213> ORGANISM: Artificial Sequence
<220> FEATURE:
<223> OTHER INFORMATION: Consensus sequence between RGA5 and RGA2 for a domain
<220> FEATURE:
<221> NAME/KEY: VARIANT
<222> LOCATION: (2)...(2)
<223> OTHER INFORMATION: Xaa = any amino acid residue
<220> FEATURE:
<221> NAME/KEY: VARIANT
<222> LOCATION: (3)...(3)
<223> OTHER INFORMATION: Xaa = Asp, Glu, Arg, Lys His
<220> FEATURE:
<221> NAME/KEY: VARIANT
<222> LOCATION: (4)...(4)
<223> OTHER INFORMATION: Xaa = any amino acid residue

```
<220> FEATURE:
<221> NAME/KEY: VARIANT
<222> LOCATION: (5)...(5)
<223> OTHER INFORMATION: Xaa = Tyr, Val, Ile, Leu, Met, Phe, Trp
<220> FEATURE:
<221> NAME/KEY: VARIANT
<222> LOCATION: (7)...(7)
<223> OTHER INFORMATION: Xaa = Arg, Lys, His
<220> FEATURE:
<221> NAME/KEY: VARIANT
<222> LOCATION: (8)...(8)
<223> OTHER INFORMATION: Xaa = any amino acid residue
<220> FEATURE:
<221> NAME/KEY: VARIANT
<222> LOCATION: (10)...(10)
<223> OTHER INFORMATION: Xaa = any amino acid residue
<220> FEATURE:
<221> NAME/KEY: VARIANT
<222> LOCATION: (13)...(13)
<223> OTHER INFORMATION: Xaa = Arg, Lys, His
<220> FEATURE:
<221> NAME/KEY: VARIANT
<222> LOCATION: (16)...(16)
<223> OTHER INFORMATION: Xaa = any amino acid residue
<220> FEATURE:
<221> NAME/KEY: VARIANT
<222> LOCATION: (17)...(17)
<223> OTHER INFORMATION: Xaa = Tyr, Val, Ile, Leu, Met, Phe, Trp
<220> FEATURE:
<221> NAME/KEY: VARIANT
<222> LOCATION: (18)...(19)
<223> OTHER INFORMATION: Xaa = any amino acid residue
<220> FEATURE:
<221> NAME/KEY: VARIANT
<222> LOCATION: (21)...(21)
<223> OTHER INFORMATION: Xaa = any amino acid residue
<220> FEATURE:
<221> NAME/KEY: VARIANT
<222> LOCATION: (22)...(22)
<223> OTHER INFORMATION: Xaa = Tyr, Val, Ile, Leu, Met, Phe, Trp
<220> FEATURE:
<221> NAME/KEY: VARIANT
<222> LOCATION: (23)...(23)
<223> OTHER INFORMATION: Xaa = Arg, Lys, His
<220> FEATURE:
<221> NAME/KEY: VARIANT
<222> LOCATION: (24)...(24)
<223> OTHER INFORMATION: Xaa = any amino acid residue
<220> FEATURE:
<221> NAME/KEY: VARIANT
<222> LOCATION: (27)...(28)
<223> OTHER INFORMATION: Xaa = any amino acid residue
<220> FEATURE:
<221> NAME/KEY: VARIANT
<222> LOCATION: (29)...(29)
<223> OTHER INFORMATION: Xaa = Tyr, Val, Ile, Leu, Met, Phe, Trp
<220> FEATURE:
<221> NAME/KEY: VARIANT
<222> LOCATION: (31)...(31)
<223> OTHER INFORMATION: Xaa = any amino acid residue
<220> FEATURE:
<221> NAME/KEY: VARIANT
<222> LOCATION: (33)...(34)
<223> OTHER INFORMATION: Xaa = any amino acid residue
<220> FEATURE:
<221> NAME/KEY: VARIANT
<222> LOCATION: (39)...(39)
<223> OTHER INFORMATION: Xaa = any amino acid residue
<220> FEATURE:
<221> NAME/KEY: VARIANT
<222> LOCATION: (40)...(40)
<223> OTHER INFORMATION: Xaa = Tyr, Val, Ile, Leu, Met, Phe, Trp
<220> FEATURE:
<221> NAME/KEY: VARIANT
<222> LOCATION: (42)...(42)
<223> OTHER INFORMATION: Xaa = any amino acid residue
```

```
<220> FEATURE:
<221> NAME/KEY: VARIANT
<222> LOCATION: (44)...(44)
<223> OTHER INFORMATION: Xaa = Gly, Ser, Ala, Thr, Pro
<220> FEATURE:
<221> NAME/KEY: VARIANT
<222> LOCATION: (45)...(45)
<223> OTHER INFORMATION: Xaa = any amino acid residue
<220> FEATURE:
<221> NAME/KEY: VARIANT
<222> LOCATION: (53)...(53)
<223> OTHER INFORMATION: Xaa = Tyr, Val, Ile, Leu, Met, Phe, Trp
<220> FEATURE:
<221> NAME/KEY: VARIANT
<222> LOCATION: (54)...(54)
<223> OTHER INFORMATION: Xaa = any amino acid residue
<220> FEATURE:
<221> NAME/KEY: VARIANT
<222> LOCATION: (55)...(55)
<223> OTHER INFORMATION: Xaa = Asp, Glu, Arg, Lys, His
<220> FEATURE:
<221> NAME/KEY: VARIANT
<222> LOCATION: (57)...(58)
<223> OTHER INFORMATION: Xaa = any amino acid residue
<220> FEATURE:
<221> NAME/KEY: VARIANT
<222> LOCATION: (61)...(61)
<223> OTHER INFORMATION: Xaa = Gly, Ser, Ala, Thr, Pro
<220> FEATURE:
<221> NAME/KEY: VARIANT
<222> LOCATION: (63)...(63)
<223> OTHER INFORMATION: Xaa = any amino acid residue
<220> FEATURE:
<221> NAME/KEY: VARIANT
<222> LOCATION: (65)...(65)
<223> OTHER INFORMATION: Xaa = any amino acid residue
<220> FEATURE:
<221> NAME/KEY: VARIANT
<222> LOCATION: (68)...(68)
<223> OTHER INFORMATION: Xaa = any amino acid residue
<220> FEATURE:
<221> NAME/KEY: VARIANT
<222> LOCATION: (70)...(71)
<223> OTHER INFORMATION: Xaa = any amino acid residue
<220> FEATURE:
<221> NAME/KEY: VARIANT
<222> LOCATION: (72)...(72)
<223> OTHER INFORMATION: Xaa = Tyr, Val, Ile, Leu, Met, Phe, Trp
<220> FEATURE:
<221> NAME/KEY: VARIANT
<222> LOCATION: (74)...(74)
<223> OTHER INFORMATION: Xaa = any amino acid residue
<220> FEATURE:
<221> NAME/KEY: VARIANT
<222> LOCATION: (75)...(75)
<223> OTHER INFORMATION: Xaa = Gly, Ser, Ala, Thr, Pro
<220> FEATURE:
<221> NAME/KEY: VARIANT
<222> LOCATION: (78)...(78)
<223> OTHER INFORMATION: Xaa = Arg, Lys, His
<220> FEATURE:
<221> NAME/KEY: VARIANT
<222> LOCATION: (80)...(80)
<223> OTHER INFORMATION: Xaa = Tyr, Val, Ile, Leu, Met, Phe, Trp
<220> FEATURE:
<221> NAME/KEY: VARIANT
<222> LOCATION: (81)...(81)
<223> OTHER INFORMATION: Xaa = any amino acid residue
<220> FEATURE:
<221> NAME/KEY: VARIANT
<222> LOCATION: (86)...(86)
<223> OTHER INFORMATION: Xaa = Arg, Lys, His
<220> FEATURE:
<221> NAME/KEY: VARIANT
<222> LOCATION: (87)...(89)
<223> OTHER INFORMATION: Xaa = any amino acid residue
```

```
<220> FEATURE:
<221> NAME/KEY: VARIANT
<222> LOCATION: (90)...(90)
<223> OTHER INFORMATION: Xaa = Asp, Glu
<220> FEATURE:
<221> NAME/KEY: VARIANT
<222> LOCATION: (91)...(91)
<223> OTHER INFORMATION: Xaa = Tyr, Val, Ile, Leu, Met, Phe, Trp
<220> FEATURE:
<221> NAME/KEY: VARIANT
<222> LOCATION: (93)...(93)
<223> OTHER INFORMATION: Xaa = Gly, Ser, Ala, Thr, Pro
<220> FEATURE:
<221> NAME/KEY: VARIANT
<222> LOCATION: (94)...(94)
<223> OTHER INFORMATION: Xaa = Asp, Glu, Arg, Lys, His
<220> FEATURE:
<221> NAME/KEY: VARIANT
<222> LOCATION: (96)...(96)
<223> OTHER INFORMATION: Xaa = any amino acid residue
<220> FEATURE:
<221> NAME/KEY: VARIANT
<222> LOCATION: (97)...(97)
<223> OTHER INFORMATION: Xaa = Asp, Glu, Arg, Lys, His
<220> FEATURE:
<221> NAME/KEY: VARIANT
<222> LOCATION: (100)...(100)
<223> OTHER INFORMATION: Xaa = Arg, Lys, His
<220> FEATURE:
<221> NAME/KEY: VARIANT
<222> LOCATION: (103)...(103)
<223> OTHER INFORMATION: Xaa = any amino acid residue
<220> FEATURE:
<221> NAME/KEY: VARIANT
<222> LOCATION: (108)...(108)
<223> OTHER INFORMATION: Xaa = any amino acid residue
<220> FEATURE:
<221> NAME/KEY: VARIANT
<222> LOCATION: (110)...(110)
<223> OTHER INFORMATION: Xaa = Tyr, Val, Ile, Leu, Met, Phe, Trp
<220> FEATURE:
<221> NAME/KEY: VARIANT
<222> LOCATION: (111)...(111)
<223> OTHER INFORMATION: Xaa = any amino acid residue
<220> FEATURE:
<221> NAME/KEY: VARIANT
<222> LOCATION: (113)...(114)
<223> OTHER INFORMATION: Xaa = any amino acid residue
<220> FEATURE:
<221> NAME/KEY: VARIANT
<222> LOCATION: (115)...(115)
<223> OTHER INFORMATION: Xaa = Arg, Lys, His
<220> FEATURE:
<221> NAME/KEY: VARIANT
<222> LOCATION: (116)...(116)
<223> OTHER INFORMATION: Xaa = any amino acid residue
<220> FEATURE:
<221> NAME/KEY: VARIANT
<222> LOCATION: (118)...(119)
<223> OTHER INFORMATION: Xaa = any amino acid residue
<220> FEATURE:
<221> NAME/KEY: VARIANT
<222> LOCATION: (120)...(120)
<223> OTHER INFORMATION: Xaa = Tyr, Val, Ile, Leu, Met, Phe, Trp
<220> FEATURE:
<221> NAME/KEY: VARIANT
<222> LOCATION: (125)...(125)
<223> OTHER INFORMATION: Xaa = Gly, Ser, Ala, Thr, Pro
<220> FEATURE:
<221> NAME/KEY: VARIANT
<222> LOCATION: (126)...(126)
<223> OTHER INFORMATION: Xaa = Tyr, Val, Ile, Leu, Met, Phe, Trp
<220> FEATURE:
<221> NAME/KEY: VARIANT
<222> LOCATION: (127)...(127)
<223> OTHER INFORMATION: Xaa = any amino acid residue
```

```
<220> FEATURE:
<221> NAME/KEY: VARIANT
<222> LOCATION: (130)...(130)
<223> OTHER INFORMATION: Xaa = Arg, Lys, His
<220> FEATURE:
<221> NAME/KEY: VARIANT
<222> LOCATION: (131)...(131)
<223> OTHER INFORMATION: Xaa = Gly, Ser, Ala, Thr, Pro
<220> FEATURE:
<221> NAME/KEY: VARIANT
<222> LOCATION: (132)...(132)
<223> OTHER INFORMATION: Xaa = any amino acid residue
<220> FEATURE:
<221> NAME/KEY: VARIANT
<222> LOCATION: (134)...(134)
<223> OTHER INFORMATION: Xaa = any amino acid residue
<220> FEATURE:
<221> NAME/KEY: VARIANT
<222> LOCATION: (136)...(136)
<223> OTHER INFORMATION: Xaa = any amino acid residue
<220> FEATURE:
<221> NAME/KEY: VARIANT
<222> LOCATION: (139)...(139)
<223> OTHER INFORMATION: Xaa = any amino acid residue
<220> FEATURE:
<221> NAME/KEY: VARIANT
<222> LOCATION: (142)...(144)
<223> OTHER INFORMATION: Xaa = any amino acid residue
<220> FEATURE:
<221> NAME/KEY: VARIANT
<222> LOCATION: (145)...(145)
<223> OTHER INFORMATION: Xaa = Asp, Glu, Arg, Lys, His
<220> FEATURE:
<221> NAME/KEY: VARIANT
<222> LOCATION: (147)...(147)
<223> OTHER INFORMATION: Xaa = Gly, Ser, Ala, Thr, Pro
<220> FEATURE:
<221> NAME/KEY: VARIANT
<222> LOCATION: (148)...(148)
<223> OTHER INFORMATION: Xaa = any amino acid residue
<220> FEATURE:
<221> NAME/KEY: VARIANT
<222> LOCATION: (151)...(151)
<223> OTHER INFORMATION: Xaa = Arg, Lys, His
<220> FEATURE:
<221> NAME/KEY: VARIANT
<222> LOCATION: (153)...(154)
<223> OTHER INFORMATION: Xaa = Asp, Glu, Arg, Lys, His
<220> FEATURE:
<221> NAME/KEY: VARIANT
<222> LOCATION: (157)...(157)
<223> OTHER INFORMATION: Xaa = any amino acid residue
<220> FEATURE:
<221> NAME/KEY: VARIANT
<222> LOCATION: (159)...(159)
<223> OTHER INFORMATION: Xaa = Asp, Glu, Arg, Lys, His
<220> FEATURE:
<221> NAME/KEY: VARIANT
<222> LOCATION: (160)...(160)
<223> OTHER INFORMATION: Xaa = any amino acid residue
<220> FEATURE:
<221> NAME/KEY: VARIANT
<222> LOCATION: (162)...(162)
<223> OTHER INFORMATION: Xaa = Asp, Glu
<220> FEATURE:
<221> NAME/KEY: VARIANT
<222> LOCATION: (164)...(164)
<223> OTHER INFORMATION: Xaa = Asp, Glu, Arg, Lys, His
<220> FEATURE:
<221> NAME/KEY: VARIANT
<222> LOCATION: (167)...(167)
<223> OTHER INFORMATION: Xaa = any amino acid residue
<220> FEATURE:
<221> NAME/KEY: VARIANT
<222> LOCATION: (169)...(175)
<223> OTHER INFORMATION: Xaa = any amino acid residue
```

-continued

```
<220> FEATURE:
<221> NAME/KEY: VARIANT
<222> LOCATION: (177)...(180)
<223> OTHER INFORMATION: Xaa = any amino acid residue
<220> FEATURE:
<221> NAME/KEY: VARIANT
<222> LOCATION: (181)...(182)
<223> OTHER INFORMATION: Xaa = Asp, Glu, Arg, Lys, His
<220> FEATURE:
<221> NAME/KEY: VARIANT
<222> LOCATION: (185)...(185)
<223> OTHER INFORMATION: Xaa = any amino acid residue
<220> FEATURE:
<221> NAME/KEY: VARIANT
<222> LOCATION: (188)...(188)
<223> OTHER INFORMATION: Xaa = any amino acid residue
<220> FEATURE:
<221> NAME/KEY: VARIANT
<222> LOCATION: (191)...(192)
<223> OTHER INFORMATION: Xaa = any amino acid residue
<220> FEATURE:
<221> NAME/KEY: VARIANT
<222> LOCATION: (194)...(194)
<223> OTHER INFORMATION: Xaa = Arg, Lys, His
<220> FEATURE:
<221> NAME/KEY: VARIANT
<222> LOCATION: (195)...(195)
<223> OTHER INFORMATION: Xaa = any amino acid residue
<220> FEATURE:
<221> NAME/KEY: VARIANT
<222> LOCATION: (197)...(197)
<223> OTHER INFORMATION: Xaa = Gly, Ser, Ala, Thr, Pro
<220> FEATURE:
<221> NAME/KEY: VARIANT
<222> LOCATION: (199)...(199)
<223> OTHER INFORMATION: Xaa = Arg, Lys, His
<220> FEATURE:
<221> NAME/KEY: VARIANT
<222> LOCATION: (200)...(200)
<223> OTHER INFORMATION: Xaa = any amino acid residue
<220> FEATURE:
<221> NAME/KEY: VARIANT
<222> LOCATION: (202)...(202)
<223> OTHER INFORMATION: Xaa = Gly, Ser, Ala, Thr, Pro
<220> FEATURE:
<221> NAME/KEY: VARIANT
<222> LOCATION: (204)...(205)
<223> OTHER INFORMATION: Xaa = Gly, Ser, Ala, Thr, Pro
<220> FEATURE:
<221> NAME/KEY: VARIANT
<222> LOCATION: (206)...(206)
<223> OTHER INFORMATION: Xaa = any amino acid residue
<220> FEATURE:
<221> NAME/KEY: VARIANT
<222> LOCATION: (210)...(210)
<223> OTHER INFORMATION: Xaa = Tyr, Val, Ile, Leu, Met, Phe, Trp
<220> FEATURE:
<221> NAME/KEY: VARIANT
<222> LOCATION: (211)...(213)
<223> OTHER INFORMATION: Xaa = any amino acid residue
<220> FEATURE:
<221> NAME/KEY: VARIANT
<222> LOCATION: (214)...(214)
<223> OTHER INFORMATION: Xaa = Tyr, Val, Ile, Leu, Met, Phe, Trp
<220> FEATURE:
<221> NAME/KEY: VARIANT
<222> LOCATION: (218)...(218)
<223> OTHER INFORMATION: Xaa = Tyr, Val, Ile, Leu, Met, Phe, Trp
<220> FEATURE:
<221> NAME/KEY: VARIANT
<222> LOCATION: (219)...(219)
<223> OTHER INFORMATION: Xaa = any amino acid residue
<220> FEATURE:
<221> NAME/KEY: VARIANT
<222> LOCATION: (221)...(221)
<223> OTHER INFORMATION: Xaa = Tyr, Val, Ile, Leu, Met, Phe, Trp
```

-continued

```
<220> FEATURE:
<221> NAME/KEY: VARIANT
<222> LOCATION: (222)...(222)
<223> OTHER INFORMATION: Xaa = Arg, Lys, His
<220> FEATURE:
<221> NAME/KEY: VARIANT
<222> LOCATION: (224)...(224)
<223> OTHER INFORMATION: Xaa = Asp, Glu, Arg, Lys, His
<220> FEATURE:
<221> NAME/KEY: VARIANT
<222> LOCATION: (225)...(225)
<223> OTHER INFORMATION: Xaa = any amino acid residue
<220> FEATURE:
<221> NAME/KEY: VARIANT
<222> LOCATION: (227)...(227)
<223> OTHER INFORMATION: Xaa = Gly, Ser, Ala, Thr, Pro
<220> FEATURE:
<221> NAME/KEY: VARIANT
<222> LOCATION: (230)...(231)
<223> OTHER INFORMATION: Xaa = any amino acid residue
<220> FEATURE:
<221> NAME/KEY: VARIANT
<222> LOCATION: (233)...(233)
<223> OTHER INFORMATION: Xaa = Gly, Ser, Ala, Thr, Pro
<220> FEATURE:
<221> NAME/KEY: VARIANT
<222> LOCATION: (234)...(234)
<223> OTHER INFORMATION: Xaa = any amino acid residue
<220> FEATURE:
<221> NAME/KEY: VARIANT
<222> LOCATION: (235)...(235)
<223> OTHER INFORMATION: Xaa = Tyr, Val, Ile, Leu, Met, Phe, Trp
<220> FEATURE:
<221> NAME/KEY: VARIANT
<222> LOCATION: (239)...(240)
<223> OTHER INFORMATION: Xaa = any amino acid residue
<220> FEATURE:
<221> NAME/KEY: VARIANT
<222> LOCATION: (242)...(242)
<223> OTHER INFORMATION: Xaa = Arg, Lys, His
<220> FEATURE:
<221> NAME/KEY: VARIANT
<222> LOCATION: (243)...(243)
<223> OTHER INFORMATION: Xaa = any amino acid residue
<220> FEATURE:
<221> NAME/KEY: VARIANT
<222> LOCATION: (246)...(246)
<223> OTHER INFORMATION: Xaa = Tyr, Val, Ile, Leu, Met, Phe, Trp
<220> FEATURE:
<221> NAME/KEY: VARIANT
<222> LOCATION: (247)...(247)
<223> OTHER INFORMATION: Xaa = Asp, Glu, Arg, Lys, His
<220> FEATURE:
<221> NAME/KEY: VARIANT
<222> LOCATION: (248)...(248)
<223> OTHER INFORMATION: Xaa = any amino acid residue
<220> FEATURE:
<221> NAME/KEY: VARIANT
<222> LOCATION: (250)...(250)
<223> OTHER INFORMATION: Xaa = Gly, Ser, Ala, Thr, Pro
<220> FEATURE:
<221> NAME/KEY: VARIANT
<222> LOCATION: (251)...(251)
<223> OTHER INFORMATION: Xaa = any amino acid residue
<220> FEATURE:
<221> NAME/KEY: VARIANT
<222> LOCATION: (253)...(253)
<223> OTHER INFORMATION: Xaa = Arg, Lys, His
<220> FEATURE:
<221> NAME/KEY: VARIANT
<222> LOCATION: (255)...(255)
<223> OTHER INFORMATION: Xaa = Tyr, Val, Ile, Leu, Met, Phe, Trp
<220> FEATURE:
<221> NAME/KEY: VARIANT
<222> LOCATION: (256)...(258)
<223> OTHER INFORMATION: Xaa = any amino acid residue
```

```
<220> FEATURE:
<221> NAME/KEY: VARIANT
<222> LOCATION: (259)...(259)
<223> OTHER INFORMATION: Xaa = Tyr, Val, Ile, Leu, Met, Phe, Trp
<220> FEATURE:
<221> NAME/KEY: VARIANT
<222> LOCATION: (260)...(260)
<223> OTHER INFORMATION: Xaa = any amino acid residue
<220> FEATURE:
<221> NAME/KEY: VARIANT
<222> LOCATION: (262)...(262)
<223> OTHER INFORMATION: Xaa = any amino acid residue
<220> FEATURE:
<221> NAME/KEY: VARIANT
<222> LOCATION: (263)...(263)
<223> OTHER INFORMATION: Xaa = Gly, Ser, Ala, Thr, Pro
<220> FEATURE:
<221> NAME/KEY: VARIANT
<222> LOCATION: (264)...(264)
<223> OTHER INFORMATION: Xaa = Asp, Glu, Arg, Lys, His
<220> FEATURE:
<221> NAME/KEY: VARIANT
<222> LOCATION: (265)...(267)
<223> OTHER INFORMATION: Xaa = any amino acid residue
<220> FEATURE:
<221> NAME/KEY: VARIANT
<222> LOCATION: (270)...(270)
<223> OTHER INFORMATION: Xaa = any amino acid residue
<220> FEATURE:
<221> NAME/KEY: VARIANT
<222> LOCATION: (273)...(273)
<223> OTHER INFORMATION: Xaa = any amino acid residue
<220> FEATURE:
<221> NAME/KEY: VARIANT
<222> LOCATION: (275)...(275)
<223> OTHER INFORMATION: Xaa = any amino acid residue
<220> FEATURE:
<221> NAME/KEY: VARIANT
<222> LOCATION: (276)...(276)
<223> OTHER INFORMATION: Xaa = Tyr, Val, Ile, Leu, Met, Phe, Trp
<220> FEATURE:
<221> NAME/KEY: VARIANT
<222> LOCATION: (277)...(278)
<223> OTHER INFORMATION: Xaa = Asp, Glu, Arg, Lys, His
<220> FEATURE:
<221> NAME/KEY: VARIANT
<222> LOCATION: (281)...(281)
<223> OTHER INFORMATION: Xaa = Gly, Ser, Ala, Thr, Pro
<220> FEATURE:
<221> NAME/KEY: VARIANT
<222> LOCATION: (283)...(283)
<223> OTHER INFORMATION: Xaa = Asp, Glu, Arg, Lys, His
<220> FEATURE:
<221> NAME/KEY: VARIANT
<222> LOCATION: (285)...(285)
<223> OTHER INFORMATION: Xaa = Tyr, Val, Ile, Leu, Met, Phe, Trp

<400> SEQUENCE: 7

Leu Xaa Xaa Xaa Xaa Phe Xaa Xaa Leu Xaa Arg Ile Xaa Val Leu Xaa
 1               5                  10                  15

Xaa Xaa Xaa Cys Xaa Xaa Xaa Xaa Leu Pro Xaa Xaa Xaa Gly Xaa Leu
            20                  25                  30

Xaa Xaa Leu Arg Tyr Leu Xaa Xaa Ser Xaa Asn Xaa Xaa Ile Gln Arg
        35                  40                  45

Leu Pro Glu Ser Xaa Xaa Xaa Leu Xaa Xaa Leu Gln Xaa Leu Xaa Leu
 50                  55                  60

Xaa Gly Cys Xaa Leu Xaa Xaa Xaa Pro Xaa Xaa Met Ser Xaa Leu Xaa
 65                  70                  75                  80

Xaa Leu Arg Gln Leu Xaa Xaa Xaa Xaa Xaa Ile Xaa Xaa Ile Xaa
                 85                  90                  95

Xaa Val Gly Xaa Leu Ile Xaa Leu Gln Glu Leu Xaa Ala Xaa Xaa Val
                100                 105                 110
```

```
                                                  -continued

Xaa Xaa Xaa Xaa Gly Xaa Xaa Xaa Ala Glu Leu Ser Xaa Xaa Xaa Gln
            115             120             125

Leu Xaa Xaa Xaa Leu Xaa Ile Xaa Asn Leu Xaa Asn Val Xaa Xaa Xaa
        130             135             140

Xaa Glu Xaa Xaa Lys Ala Xaa Leu Xaa Xaa Lys Gln Xaa Leu Xaa Xaa
145             150             155             160

Leu Xaa Leu Xaa Trp Ala Xaa Gly Xaa Xaa Xaa Xaa Xaa Xaa Xaa Glu
            165             170             175

Xaa Xaa Xaa Xaa Xaa Xaa Val Leu Xaa Gly Leu Xaa Pro His Xaa Xaa
            180             185             190

Leu Xaa Xaa Leu Xaa Ile Xaa Xaa Tyr Xaa Gly Xaa Xaa Xaa Pro Ser
        195             200             205

Trp Xaa Xaa Xaa Xaa Xaa Leu Pro Asn Xaa Xaa Thr Xaa Xaa Leu Xaa
        210             215             220

Xaa Cys Xaa Arg Leu Xaa Xaa Leu Xaa Xaa Xaa Gly Gln Leu Xaa Xaa
225             230             235             240

Leu Xaa Xaa Leu His Xaa Xaa Xaa Met Xaa Xaa Val Xaa Gln Xaa Xaa
            245             250             255

Xaa Xaa Xaa Xaa Gly Xaa Xaa Xaa Xaa Xaa Xaa Phe Pro Xaa Leu Glu
            260             265             270

Xaa Leu Xaa Xaa Xaa Xaa Met Pro Xaa Leu Xaa Glu Xaa
        275             280             285
```